(12) United States Patent
Coffin et al.

(10) Patent No.: US 10,647,626 B2
(45) Date of Patent: May 12, 2020

(54) DECENE OLIGOMERS

(71) Applicant: Chevron Phillips Chemical Company LP, The Woodlands, TX (US)

(72) Inventors: Robert C. Coffin, Kingwood, TX (US); Steven M. Bischof, Humble, TX (US); Lauren M. Kattchee, Houston, TX (US); Kenneth M. Lassen, Bartlesville, OK (US); Jason L. Kreider, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 233 days.

(21) Appl. No.: 15/207,712

(22) Filed: Jul. 12, 2016

(65) Prior Publication Data
US 2018/0016204 A1   Jan. 18, 2018

(51) Int. Cl.
*C07C 2/08* (2006.01)
*C10M 107/10* (2006.01)
(Continued)

(52) U.S. Cl.
CPC .................. *C07C 2/08* (2013.01); *C07C 2/06* (2013.01); *C07C 2/12* (2013.01); *C07C 2/26* (2013.01);
(Continued)

(58) Field of Classification Search
CPC ..... C07C 2/08; C07C 2/26; C07C 2527/1213; C07C 2527/125; C07C 2531/02;
(Continued)

(56) References Cited

U.S. PATENT DOCUMENTS

| 1,815,022 A | 7/1931 | Davis |
| 2,015,748 A | 10/1935 | Frolich |

(Continued)

FOREIGN PATENT DOCUMENTS

| CN | 103100419 A | 5/2013 |
| CN | 103100419 B | 4/2015 |

(Continued)

OTHER PUBLICATIONS

Foreign communication from a related counterpart application—International Search Report and Written Opinion, PCT/US2017/035980, dated Aug. 29, 2017, 12 pages.
(Continued)

*Primary Examiner* — Ali Z Fadhel
(74) *Attorney, Agent, or Firm* — Conley Rose, P.C.

(57) ABSTRACT

A composition comprising olefin oligomers of one or more olefin monomers, the olefin monomers comprising a branched $C_{10}$ olefin monomer comprising i) 3-propyl-1-heptene, ii) 4-ethyl-1-octene, iii) 5-methyl-1-nonene, or iv) any combination thereof. A composition comprising substantially hydrogenated olefin oligomers, wherein the olefin oligomers are oligomers of one or more olefin monomers, the olefin monomers comprising a branched $C_{10}$ olefin monomer comprising i) 3-propyl-1-heptene, ii) 4-ethyl-1-octene, iii) 5-methyl-1-nonene, or iv) any combination thereof. A process comprising a) contacting 1) a catalyst system and 2) a monomer feedstock comprising a branched $C_{10}$ olefin monomer comprising i) 3-propyl-1-heptene, ii) 4-ethyl-1-octene, iii) 5-methyl-1-nonene, or iv) any combination thereof in a reaction zone; and b) forming olefin oligomers.

16 Claims, 5 Drawing Sheets

(51) Int. Cl.
*C07C 2/12* (2006.01)
*C07C 2/06* (2006.01)
*C07C 2/88* (2006.01)
*C10M 105/04* (2006.01)
*C07C 2/26* (2006.01)

(52) U.S. Cl.
CPC .............. *C07C 2/88* (2013.01); *C10M 105/04* (2013.01); *C10M 107/10* (2013.01); *C07C 2527/125* (2013.01); *C07C 2527/1213* (2013.01); *C07C 2531/02* (2013.01); *C10M 2205/0285* (2013.01); *C10N 2220/028* (2013.01); *C10N 2260/02* (2013.01)

(58) Field of Classification Search
CPC ... C07C 2/06; C07C 2/12; C07C 2/88; C10M 2205/0285; C10M 105/04; C10M 107/10; C10N 2220/028; C10N 2260/02
See application file for complete search history.

(56) References Cited

U.S. PATENT DOCUMENTS

| | | |
|---|---|---|
| 2,191,498 A | 2/1940 | Reiff |
| 2,387,501 A | 10/1945 | Dietrich |
| 2,443,264 A | 6/1948 | Mikeska |
| 2,471,115 A | 5/1949 | Mikeska |
| 2,526,497 A | 10/1950 | Mikeska |
| 2,591,577 A | 4/1952 | McDermott |
| 2,655,479 A | 10/1953 | Munday et al. |
| 2,666,746 A | 1/1954 | Munday et al. |
| 2,719,125 A | 9/1955 | Roberts |
| 2,719,126 A | 9/1955 | Fields et al. |
| 2,721,877 A | 10/1955 | Popkin et al. |
| 2,721,878 A | 10/1955 | Popkin |
| 3,036,003 A | 5/1962 | Verdol |
| 3,087,932 A | 4/1963 | Little, Jr. |
| 3,087,936 A | 4/1963 | Le Suer |
| 3,172,892 A | 3/1965 | Le Suer et al. |
| 3,200,107 A | 8/1965 | Le Suer |
| 3,215,707 A | 11/1965 | Rense |
| 3,219,666 A | 11/1965 | Norman et al. |
| 3,250,715 A | 5/1966 | Wyman |
| 3,254,025 A | 5/1966 | Le Suer |
| 3,272,746 A | 9/1966 | Le Suer et al. |
| 3,275,554 A | 9/1966 | Wagenaar |
| 3,316,177 A | 4/1967 | Dorer, Jr. |
| 3,322,670 A | 5/1967 | Burt et al. |
| 3,329,658 A | 7/1967 | Fields |
| 3,341,542 A | 9/1967 | Le Suer et al. |
| 3,382,291 A | 5/1968 | Brennan |
| 3,413,347 A | 11/1968 | Worrel |
| 3,438,757 A | 4/1969 | Honnen et al. |
| 3,444,170 A | 5/1969 | Norman et al. |
| 3,449,250 A | 6/1969 | Fields |
| 3,454,555 A | 7/1969 | van der Voort et al. |
| 3,454,607 A | 7/1969 | Le Suer et al. |
| 3,519,565 A | 7/1970 | Coleman |
| 3,541,012 A | 11/1970 | Stuebe |
| 3,565,804 A | 2/1971 | Honnen et al. |
| 3,630,904 A | 12/1971 | Musser et al. |
| 3,632,511 A | 1/1972 | Liao |
| 3,652,616 A | 3/1972 | Watson et al. |
| 3,666,730 A | 5/1972 | Coleman |
| 3,687,849 A | 8/1972 | Abbott |
| 3,697,574 A | 10/1972 | Piasek et al. |
| 3,702,300 A | 11/1972 | Coleman |
| 3,703,536 A | 11/1972 | Piasek et al. |
| 3,704,308 A | 11/1972 | Piasek et al. |
| 3,725,277 A | 4/1973 | Worrel |
| 3,725,480 A | 4/1973 | Traise et al. |
| 3,726,882 A | 4/1973 | Traise et al. |
| 3,751,365 A | 8/1973 | Piasek et al. |
| 3,755,433 A | 8/1973 | Miller et al. |
| 3,756,953 A | 9/1973 | Piasek et al. |
| 3,770,854 A | 11/1973 | Morris et al. |
| 3,787,374 A | 1/1974 | Adams |
| 3,798,165 A | 3/1974 | Piasek et al. |
| 3,803,039 A | 4/1974 | Piasek et al. |
| 3,822,209 A | 7/1974 | Knapp et al. |
| 3,948,800 A | 4/1976 | Meinhardt |
| 3,957,664 A | 5/1976 | Heilman et al. |
| 4,045,507 A | 8/1977 | Cupples et al. |
| 4,045,508 A | 8/1977 | Cupples et al. |
| 4,100,082 A | 7/1978 | Clason et al. |
| 4,172,855 A | 10/1979 | Shubkin et al. |
| 4,234,435 A | 11/1980 | Meinhardt et al. |
| 4,409,415 A | 10/1983 | Morganson et al. |
| 4,426,305 A | 1/1984 | Malec |
| 4,451,684 A | 5/1984 | Pasky |
| 4,454,059 A | 6/1984 | Pindar et al. |
| 4,484,014 A | 11/1984 | Nelson et al. |
| 4,501,678 A | 2/1985 | Katayama et al. |
| 4,767,551 A | 8/1988 | Hunt et al. |
| 4,798,684 A | 1/1989 | Salomon |
| 4,827,064 A | 5/1989 | Wu |
| 4,941,984 A | 7/1990 | Chamberlin, III et al. |
| 4,962,249 A | 10/1990 | Chen et al. |
| 5,034,141 A | 7/1991 | Beltzer et al. |
| 5,034,142 A | 7/1991 | Habeeb et al. |
| 5,066,741 A | 11/1991 | Campbell, Jr. |
| 5,084,197 A | 1/1992 | Galic et al. |
| 5,113,030 A | 5/1992 | Chen et al. |
| 5,153,157 A | 10/1992 | Hlatky et al. |
| 5,198,401 A | 3/1993 | Turner et al. |
| 5,206,197 A | 4/1993 | Campbell, Jr. |
| 5,241,025 A | 8/1993 | Hlatky et al. |
| 5,278,119 A | 1/1994 | Turner et al. |
| 5,284,988 A | 2/1994 | Schaerfl, Jr. et al. |
| 5,384,299 A | 1/1995 | Turner et al. |
| 5,387,568 A | 2/1995 | Ewen et al. |
| 5,447,895 A | 9/1995 | Marks et al. |
| 5,486,632 A | 1/1996 | Devore et al. |
| 5,498,815 A | 3/1996 | Schaerfl, Jr. et al. |
| 5,502,124 A | 3/1996 | Crowther et al. |
| 5,527,929 A | 6/1996 | Timmers et al. |
| 5,573,657 A | 11/1996 | Degnan et al. |
| 5,624,878 A | 4/1997 | Devore et al. |
| 5,693,598 A | 12/1997 | Abraham et al. |
| 5,705,458 A | 1/1998 | Roby et al. |
| 6,107,230 A | 8/2000 | McDaniel et al. |
| 6,165,929 A | 12/2000 | McDaniel et al. |
| 6,294,494 B1 | 9/2001 | McDaniel et al. |
| 6,300,271 B1 | 10/2001 | McDaniel et al. |
| 6,316,553 B1 | 11/2001 | McDaniel et al. |
| 6,355,594 B1 | 3/2002 | McDaniel et al. |
| 6,376,415 B1 | 4/2002 | McDaniel et al. |
| 6,391,816 B1 | 5/2002 | McDaniel et al. |
| 6,395,666 B1 | 5/2002 | McDaniel et al. |
| 6,395,948 B1 | 5/2002 | Hope et al. |
| 6,524,987 B1 | 2/2003 | Collins et al. |
| 6,548,441 B1 | 4/2003 | McDaniel et al. |
| 6,730,818 B2 | 5/2004 | Heilman et al. |
| 6,750,302 B1 | 6/2004 | McDaniel et al. |
| 6,831,141 B2 | 12/2004 | McDaniel et al. |
| 6,936,667 B2 | 8/2005 | Jensen et al. |
| 6,992,032 B2 | 1/2006 | McDaniel et al. |
| 7,026,494 B1 | 4/2006 | Yang et al. |
| 7,041,617 B2 | 5/2006 | Jensen et al. |
| 7,148,298 B2 | 12/2006 | Jensen et al. |
| 7,199,073 B2 | 4/2007 | Martin et al. |
| 7,226,886 B2 | 6/2007 | Jayaratne et al. |
| 7,294,599 B2 | 11/2007 | Jensen et al. |
| 7,312,283 B2 | 12/2007 | Martin et al. |
| 7,470,758 B2 | 12/2008 | Jensen et al. |
| 7,501,372 B2 | 3/2009 | Thorn et al. |
| 7,517,939 B2 | 4/2009 | Yang et al. |
| 7,576,163 B2 | 8/2009 | Yang et al. |
| 7,601,665 B2 | 10/2009 | McDaniel et al. |
| 7,619,047 B2 | 11/2009 | Yang et al. |
| 7,629,284 B2 | 12/2009 | Jensen et al. |
| 7,652,186 B2 | 1/2010 | Goze et al. |
| 7,884,163 B2 | 2/2011 | McDaniel et al. |
| 7,919,639 B2 | 4/2011 | Murray et al. |

(56) References Cited

U.S. PATENT DOCUMENTS

| | | | |
|---|---|---|---|
| 8,080,681 | B2 | 12/2011 | Murray et al. |
| 8,309,485 | B2 | 11/2012 | Yang et al. |
| 8,623,973 | B1 | 1/2014 | McDaniel et al. |
| 8,703,886 | B1 | 4/2014 | Yang et al. |
| 9,023,959 | B2 | 5/2015 | McDaniel et al. |
| 9,206,095 | B2 | 12/2015 | Bagheri et al. |
| 2005/0113621 | A1* | 5/2005 | Hope ............ C07C 2/22 585/521 |
| 2006/0025643 | A1* | 2/2006 | Rath ............ C07C 2/20 585/522 |
| 2007/0081959 | A1 | 4/2007 | Schmid et al. |
| 2008/0146469 | A1 | 6/2008 | Sato et al. |
| 2009/0240012 | A1 | 9/2009 | Patil et al. |
| 2010/0076167 | A1 | 3/2010 | McDaniel et al. |
| 2010/0222618 | A1 | 9/2010 | Takagi et al. |
| 2011/0039743 | A1 | 2/2011 | Bagheri et al. |
| 2014/0128557 | A1* | 5/2014 | Giesbrecht ...... C08F 4/64189 526/127 |
| 2015/0166429 | A1 | 6/2015 | Gee et al. |

FOREIGN PATENT DOCUMENTS

| | | | |
|---|---|---|---|
| CN | 106883899 A * | 6/2017 | ............ C07C 2/10 |
| EP | 0277003 A1 | 8/1988 | |
| EP | 0277004 A1 | 8/1988 | |
| EP | 0377306 A1 | 7/1990 | |
| EP | 0426637 A2 | 5/1991 | |
| EP | 0427697 A2 | 5/1991 | |
| EP | 0495375 A2 | 7/1992 | |
| EP | 0500944 A1 | 9/1992 | |
| EP | 0520732 A1 | 12/1992 | |
| EP | 0570982 A1 | 11/1993 | |
| EP | 0573403 A2 | 12/1993 | |
| EP | 0612768 A1 | 8/1994 | |
| EP | 0500944 B1 | 10/1998 | |
| WO | 0121675 A1 | 3/2001 | |

OTHER PUBLICATIONS

Bibliographic data for patent application entitled "Supported Ionic Catalyst Composition," by John F. Walzer, filed on Aug. 3, 1994 as U.S. Appl. No. 08/285,380, now abandoned.

Chen, Eugene You-Xian, et al., "Cocatalysts for Metal-Catalyzed Olefin Polymerization: Activators, Activation Processes, and Structure-Activity Relationships," Chemical Reviews, 2000, pp. 1391-1434, vol. 100, No. 4, American Chemical Society.

Enderby, John E., "Ionic liquids: recent progress and remaining problems," J. Phys.: Condens. Matter, 1993, pp. B99-B106, vol. 5, IOP Publishing Ltd, United Kingdom.

Filing receipt and specification for International application entitled "Olefin Compositions," filed Jul. 14, 2015 as International application No. PCT/US2015/040433.

Filing receipt and specification for patent application entitled "Method for Making Polyalphaolefins Using Ionic Liquid Catalyzed Oligomerization of Olefins," by Steven M. Bischof, et al., filed Aug. 19, 2015 as U.S. Appl. No. 14/829,987.

Freemantle, Michael, "Designer Solvents: Ionic liquids may boost clean technology development," C&EN, Mar. 30, 1998, pp. 32-37.

Gee, Jeffrey C., et al., "Behavior of protonated cyclopropyl intermediates during polyalphaolefin synthesis: Mechanism and predicted product distribution," Journal of Physical Organic Chemistry, 2012, pp. 1409-1417, vol. 25, John Wiley & Sons, Ltd.

Gordon, Charles M., et al., "Ionic liquid crystals: hexafluorophosphate salts," Journal of Materials Chemistry, 1998, pp. 2627-2636, vol. 8.

"Group notation revised in periodic table," Feb. 4, 1985, pp. 26-27, C&EN.

Klamann, Dieter, et al., "Lubricants and Related Products," 1984, pp. 199-248 plus 1 cover page, Verlag Chemie.

Mang, Theo, et al., "Lubricants and Lubrication," 2001, 1 page, Wiley-VCH.

McNaught, Alan D., et al., "Compendium of Chemical Terminology," International Union of Pure and Applied Chemistry, Second edition, 1997, 5 pages of cover, publishing information, and contents, Wiley-Blackwell.

Ranney, M. W., "Lubricant Additives," Chemical Technology Review No. 2, 1973, 349 pages, Noyes Data Corporation.

Reed, Christopher A., "Carboranes: A New Class of Weakly Coordinating Anions for Strong Electrophiles, Oxidants, and Superacids," Accounts of Chemical Research, 1998, pp. 133-139, vol. 31, No. 3, American Chemical Society.

Rudnick, Leslie R., et al., "Synthetic Lubricants and High-Performance Functional Fluids," 1999, 1 page, Second Edition, CRC Press.

Seddon, Kenneth R., "Ionic Liquids for Clean Technology," J. Chem. Tech. Biotechnol., 1997, pp. 351-356, vol. 68, SCI, Great Britain.

Sequeira, Jr., Avilino, "Lubricant Base Oil and Wax Processing," Chapter 6, "Lubricant Base Oil Hydrogen Refining Processes," 1994, pp. 119-152 plus 1 page cover and publishing information, Marcel Dekker Inc.

Smalheer, C. V., et al., "Lubricant Additives," 1967, 91 pages, The Lezius-Hiles Co., The Lubrizol Corporation.

Strauss, Steven H., "The Search for Larger and More Weakly Coordinating Anions," Chemical Reviews, 1993, pp. 927-942, vol. 93, No. 3, American Chemical Society.

Totten, George E, et al., "Fuels and Lubricants Handbook: Technology, Properties, Performance, and Testing," 2003, 3 pages, ASTM International.

Welton, Thomas, "Room-Temperature Ionic Liquids. Solvents for Synthesis and Catalysis," Chemical Reviews, 1999, pp. 2071-2083, vol. 99, No. 8, American Chemical Society.

* cited by examiner

DECENE OLIGOMERS

TECHNICAL FIELD OF THE INVENTION

The present disclosure relates to compositions containing decene oligomers and methods of making same. More specifically, the present disclosure relates to compositions containing decene oligomers produced by oligomerization of branched decenes.

BACKGROUND OF THE INVENTION

Olefin oligomers, hydrogenated olefin oligomers, and their derivatives are used for the production of a wide variety of articles (e.g., synthetic lubricants or lubricant additives). The use of particular olefin oligomers and/or hydrogenated olefin oligomers in a particular application will depend on the type of physical and/or mechanical properties displayed by the olefin oligomers and/or hydrogenated olefin oligomers. Such properties can be a result of the method used for producing particular olefin oligomers and/or hydrogenated olefin oligomers, e.g., the olefins used for producing the olefin oligomers, the reaction conditions under which the olefin oligomers are produced, etc. Conventionally, $C_8$-$C_{12}$ linear alpha-olefins can be oligomerized in the presence of a Lewis acid catalyst to generate olefin oligomers which can be hydrogenated to produce polyalphaolefins used in synthetic lubricants or lubricant additives. However, with ever increasing demands on transportation and heavy industries to improve fuel efficiency and extend oil change intervals, the use of synthetic oils for lubrication has rapidly expanded, thus leading to constraints on the available supplies of linear alpha-olefin fractions typically utilized for these products. Thus, there is an ongoing need to develop olefin oligomers and polyalphaolefins produced from alternative olefin feedstocks and methods for making same.

SUMMARY OF THE INVENTION

Disclosed herein is a composition comprising olefin oligomers of one or more olefin monomers, the olefin monomers comprising a branched $C_{10}$ olefin monomer comprising i) 3-propyl-1-heptene, ii) 4-ethyl-1-octene, iii) 5-methyl-1-nonene, or iv) any combination thereof.

Also disclosed herein is a composition comprising substantially hydrogenated olefin oligomers, wherein the olefin oligomers are oligomers of one or more olefin monomers, the olefin monomers comprising a branched $C_{10}$ olefin monomer comprising i) 3-propyl-1-heptene, ii) 4-ethyl-1-octene, iii) 5-methyl-1-nonene, or iv) any combination thereof.

Further disclosed herein is a process comprising a) contacting 1) a catalyst system and 2) a monomer feedstock comprising a branched $C_{10}$ olefin monomer comprising i) 3-propyl-1-heptene, ii) 4-ethyl-1-octene, iii) 5-methyl-1-nonene, or iv) any combination thereof in a reaction zone; and b) forming olefin oligomers.

DESCRIPTION OF THE DRAWINGS

For a detailed description of the preferred embodiments of the disclosed processes and systems, reference will now be made to the accompanying drawings in which.

DETAILED DESCRIPTION OF THE INVENTION

Figure 1A:
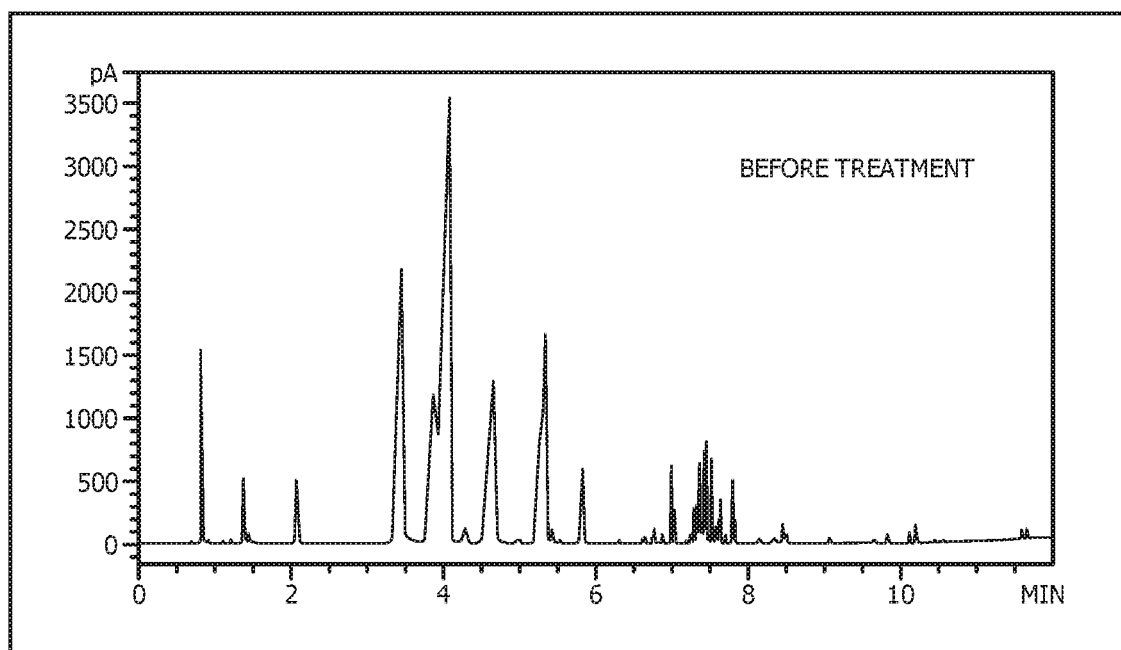
FIGS. 1A and 1B provide a comparison of gas chromatographic (GC) traces of a mixed olefin stream from a selective ethylene trimerization plant (1A, before treatment) and treated mixed olefins (1B, after treatment).

Disclosed herein are compositions comprising olefin oligomers of one or more olefin monomers, the olefin monomers comprising a branched $C_{10}$ olefin monomer. Also disclosed herein are compositions comprising substantially hydrogenated olefin oligomers, wherein the olefin oligomers are oligomers of one or more olefin monomers, the olefin monomers comprising a branched $C_{10}$ olefin monomer. In an embodiment, a process can comprise a) contacting 1) a catalyst system and 2) a monomer feedstock comprising a branched $C_{10}$ olefin monomer in a reaction zone; and b) forming olefin oligomers. In such embodiment, the process can further comprise removing a reaction zone effluent from the reaction zone and optionally contacting the reaction zone effluent with a catalyst system deactivating agent to form a deactivated reaction zone effluent. In some embodiments, the process can further comprise isolating one or more fractions comprising all or a portion of the olefin oligomers from the reaction zone effluent or deactivated reaction zone effluent. In such embodiments, the process can further comprise hydrogenating at least one of the one or more fractions comprising all or a portion of the olefin oligomers.

To define more clearly the terms used herein, the following definitions are provided. Unless otherwise indicated, the following definitions are applicable to this disclosure. If a term is used in this disclosure, but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Groups of elements of the Periodic Table are indicated using the numbering scheme indicated in the version of the Periodic Table of elements published in *Chemical and Engineering News*, 63(5), 27, 1985. In some instances, a group of elements can be indicated using a common name assigned to the group; for example, alkali metals for Group 1 elements, alkaline earth metals (or alkaline metals) for Group 2 elements, transition metals for Groups 3-12 elements, and halogens for Group 17 elements.

Regarding claim transitional terms or phrases, the transitional term "comprising", which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention.

The term "consisting essentially of" occupies a middle ground between closed terms like "consisting of" and fully open terms like "comprising." Absent an indication to the contrary, when describing a compound or composition, "consisting essentially of" is not to be construed as "comprising," but is intended to describe the recited component that includes materials which do not significantly alter the composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class to which is utilized and it is possible to have different transitional terms or phrases utilized with different features within a claim. For example, a method can comprise several recited steps (and other non-recited steps), but utilize a catalyst system preparation consisting of specific steps, or alternatively, consisting essentially of specific steps, but utilize a catalyst system comprising recited components and other non-recited components.

While compositions and methods are described in terms of "comprising" (or any other broad term) various components and/or steps, the compositions and methods can also be described using narrower terms, such as "consist essentially of" or "consist of" the various components and/or steps.

The terms "a," "an," and "the" are intended, unless specifically indicated otherwise, to include plural alternatives, e.g., at least one. For instance, the disclosure of "a trialkylaluminum compound" is meant to encompass one trialkylaluminum compound, or mixtures or combinations of more than one trialkylaluminum compound, unless otherwise specified.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers, unless explicitly indicated otherwise; e.g., a general reference to pentane includes n-pentane, 2-methyl-butane, and 2,2-dimethylpropane, while a general reference to a butyl group includes an n-butyl group, a sec-butyl group, an iso-butyl group, and a tert-butyl group. Additionally, the reference to a general structure or name encompasses all enantiomers, diastereomers, and other optical isomers, whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner. By way of example, an "alkyl group" can formally be derived by removing one hydrogen atom from an alkane, while an "alkylene group" can formally be derived by removing two hydrogen atoms from an alkane. Moreover, a more general term can be used to encompass a variety of groups that formally are derived by removing any number ("one or more") of hydrogen atoms from a parent compound, which in this example can be described as an "alkane group," and which encompasses an "alkyl group," an "alkylene group," and materials having three or more hydrogens atoms, as necessary for the situation, removed from the alkane. Throughout, the disclosure of a substituent, ligand, or other chemical moiety that can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedures, unless specified otherwise or the context requires otherwise.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from one or two carbon atoms of an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, phosphines, and so forth. An "organyl group," "organylene group," or "organic group" can be aliphatic, inclusive of being cyclic or acyclic, or can be aromatic. "Organyl groups," "organylene groups," and "organic groups" also encompass heteroatom-containing rings, heteroatom-containing ring systems, heteroaromatic rings, and heteroaromatic ring systems. "Organyl groups," "organylene groups," and "organic groups" can be linear or branched unless otherwise specified. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," respectively, as members.

For the purposes of this application, the term or variations of the term "organyl group consisting of inert functional groups" refers to an organyl group wherein the organic functional group(s) and/or atom(s) other than carbon and hydrogen present in the functional group are restricted to those functional group(s) and/or atom(s) other than carbon and hydrogen which do not complex with a metal compound and/or are inert under the process conditions defined herein. Thus, the term or variation of the term "organyl group consisting of inert functional groups" further defines the particular organyl groups that can be present within the organyl group consisting of inert functional groups. Additionally, the term "organyl group consisting of inert functional groups" can refer to the presence of one or more inert functional groups within the organyl group. The term or variation of the term "organyl group consisting of inert functional groups" definition includes the hydrocarbyl group as a member (among other groups). Similarly, an "organylene group consisting of inert functional groups" refers to an organic group formed by removing two hydrogen atoms from one or two carbon atoms of an organic compound consisting of inert functional groups and an "organic group consisting of inert functional groups" refers to a generalized organic group consisting of inert functional groups formed by removing one or more hydrogen atoms from one or more carbon atoms of an organic compound consisting of inert functional groups.

For purposes of this application, an "inert functional group" is a group which does not substantially interfere with the process described herein in which the material having an inert functional group takes part and/or does not complex with a metal compound of a metal complex. The term "does not complex with the metal compound" can include groups that could complex with a metal compound but in particular molecules described herein may not complex with a metal compound due to its positional relationship within a ligand. For example, while an ether group can complex with a metal compound, an ether group located at a para position of a substituted phenyl attached to a complexing heteroatom of a ligand can be an inert functional group because a single metal compound cannot complex with both the para ether group of the substituted phenyl group and the complexing heteroatom of the ligand to which the substituted phenyl group is attached. Thus, the inertness of a particular functional group is not only related to the functional group's inherent inability to complex the metal compound, but can also be related to the functional group's position within the metal complex. Non-limiting examples of inert functional groups which do not substantially interfere with processes described herein can include halo (fluoro, chloro, bromo, and iodo), nitro, hydrocarboxy groups (e.g., alkoxy, and/or aroxy, among others), sulfidyl groups, and/or hydrocarbyl groups, among others.

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g., halogenated alkane indicates the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl group are derived by removal of a hydrogen atom from a primary, secondary, and tertiary carbon atom, respectively, of an alkane. The n-alkyl group can be derived by removal of a hydrogen atom from a terminal carbon atom of a linear alkane.

An aliphatic compound is an acyclic or cyclic, saturated or unsaturated carbon compound, excluding aromatic compounds. Thus, an aliphatic compound is an acyclic or cyclic, saturated or unsaturated carbon compound, excluding aromatic compounds; that is, an aliphatic compound is a non-aromatic organic compound. An "aliphatic group" is a generalized group formed by removing one or more hydrogen atoms (as necessary for the particular group) from a carbon atom of an aliphatic compound. Thus, an aliphatic compound is an acyclic or cyclic, saturated or unsaturated carbon compound, excluding aromatic compounds. That is, an aliphatic compound is a non-aromatic organic compound. Aliphatic compounds and therefore aliphatic groups can contain organic functional group(s) and/or atom(s) other than carbon and hydrogen.

The term "substituted" when used to describe a compound or group, for example, when referring to a substituted analog of a particular compound or group, is intended to describe any non-hydrogen moiety that formally replaces a hydrogen in that group, and is intended to be non-limiting. A group or groups can also be referred to herein as "unsubstituted" or by equivalent terms, such as "non-substituted," which refers to the original group in which a non-hydrogen moiety does not replace a hydrogen within that group. "Substituted" is intended to be non-limiting and include inorganic substituents or organic substituents.

The term "olefin" whenever used in this specification and claims refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s).

The term "alkene" whenever used in this specification and claims refers to a linear or branched aliphatic hydrocarbon olefin that has one or more carbon-carbon double bonds. Alkenes having only one, only two, only three, etc., such multiple bonds can be identified by use of the term "mono," "di," "tri," etc., within the name. For example, alkamonoenes, alkadienes, and alkatrienes refer to linear or branched acyclic hydrocarbon olefins having only one carbon-carbon double bond (acyclic having a general formula of $C_nH_{2n}$), only two carbon-carbon double bonds (acyclic having a general formula of $C_nH_{2n-2}$), and only three carbon-carbon double bonds (acyclic having a general formula of $C_nH_{2n-4}$), respectively. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replaced with a halogen atom.

The term "alpha olefin" as used in this specification and claims refers to an olefin that has a carbon-carbon double bond between the first and second carbon atoms of the longest contiguous chain of carbon atoms. The term "alpha olefin" includes linear and branched alpha olefins unless expressly stated otherwise. In the case of branched alpha olefins, a branch can be at the 2 position (a vinylidene) and/or the 3 position or higher with respect to the olefin double bond. The term "vinylidene" whenever used in this specification and claims refers to an alpha olefin having a branch at the 2 position with respect to the olefin double bond. By itself, the term "alpha olefin" does not indicate the presence or absence of other carbon-carbon double bonds unless explicitly indicated.

The term "normal alpha olefin" whenever used in this specification and claims refers to a linear aliphatic mono-olefin having a carbon-carbon double bond between the first and second carbon atoms. It is noted that "normal alpha olefin" is not synonymous with "linear alpha olefin" as the term "linear alpha olefin" can include linear olefinic compounds having a double bond between the first and second carbon atoms.

The terms "room temperature" or "ambient temperature" are used herein to describe any temperature from 15° C. to 35° C. wherein no external heat or cooling source is directly applied to the reaction vessel. Accordingly, the terms "room temperature" and "ambient temperature" encompass the individual temperatures and any and all ranges, subranges, and combinations of subranges of temperatures from 15° C. to 35° C. wherein no external heating or cooling source is directly applied to the reaction vessel. The term "atmospheric pressure" is used herein to describe an earth air pressure wherein no external pressure modifying means is utilized. Generally, unless practiced at extreme earth altitudes, "atmospheric pressure" is about 1 atmosphere (alternatively, about 14.7 psi or about 101 kPa).

Features within this disclosure that are provided as a minimum value can be alternatively stated as "at least" or "greater than or equal to" any recited minimum value for the feature disclosed herein. Features within this disclosure that are provided as a maximum value can be alternatively stated as "less than or equal to" any recited maximum value for the feature disclosed herein.

Within this disclosure, the normal rules of organic nomenclature will prevail. For instance, when referencing substituted compounds or groups, references to substitution patterns are taken to indicate that the indicated group(s) is (are) located at the indicated position(s) and that all other non-indicated positions are hydrogen. For example, reference to a 4-substituted phenyl group indicates that there is a non-hydrogen substituent located at the 4 position and hydrogens located at the 2, 3, 5, and 6 positions. By way of another example, reference to a 3-substituted naphth-2-yl indicates that there is a non-hydrogen substituent located at the 3 position and hydrogens located at the 1, 4, 5, 6, 7, and 8 positions. References to compounds or groups having substitutions at positions in addition to the indicated position will be referenced using comprising or some other alternative language. For example, a reference to a phenyl group comprising a substituent at the 4 position refers to a phenyl group having a non-hydrogen substituent group at the 4 position and hydrogen or any non-hydrogen group at the 2, 3, 5, and 6 positions.

Use of the term "optionally" with respect to any element of a claim is intended to mean that the subject element is required, or alternatively, is not required. Both alternatives are intended to be within the scope of the claim.

Unless otherwise specified, any carbon-containing group for which the number of carbon atoms is not specified can have, according to proper chemical practice, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, or any range or combination of ranges between these values. For example, unless otherwise specified, any carbon-containing group can have from 1 to 30 carbon atoms, from 1 to 25 carbon atoms, from 1 to 20 carbon atoms, from 1 to 15 carbon atoms, from 1 to 10 carbon atoms, or from 1 to 5 carbon atoms. Moreover, other identifiers or qualifying terms can be utilized to indicate the presence or absence of a particular substituent, a particular regiochemistry and/or stereochemistry, or the presence or absence of a branched underlying structure or backbone.

Processes and/or methods described herein can utilize steps, features, and compounds which are independently described herein. Similarly, compositions described herein can have multiple features and/or compound classes that are independently described herein. The compositions, process, and methods described herein may or may not utilize identifiers (e.g., 1), 2), etc., a), b), etc., or i), ii), etc.), features (e.g., 1), 2), etc., a), b), etc., or i), ii), etc.), and/or compound identifiers (e.g., first, second, etc.). However, it should be noted that compositions, processes, and/or methods described herein can have multiple steps, features (e.g., reagent ratios, formation conditions, among other considerations), and/or multiple compounds having the same general descriptor. Consequently, it should be noted that the compositions, processes, and/or methods described herein can be modified to use an appropriate composition feature, compound class, step, or feature identifier (e.g., 1), 2), etc., a), b), etc., or i), ii), etc.) and/or compound identifier (e.g., first, second, etc.) regardless of class, step, feature, and/or compound identifier utilized in a particular aspect and/or embodiment described herein and that composition feature, compound class, step or feature identifiers can be added and/or modified to indicate individual different composition feature/compound class/step/feature/compounds utilized within the compositions, processes, and/or methods without detracting from the general disclosure.

Embodiments disclosed herein can provide the materials listed as suitable for satisfying a particular feature of the embodiment delimited by the term "or." For example, a particular feature of the disclosed subject matter can be disclosed as follows: Feature X can be A, B, or C. It is also contemplated that for each feature the statement can also be phrased as a listing of alternatives such that the statement "Feature X is A, alternatively B, or alternatively C" is also an embodiment of the present disclosure whether or not the statement is explicitly recited.

In an embodiment, the compositions described herein can comprise olefin oligomers of one or more olefin monomers, the olefin monomers comprising a branched $C_{10}$ olefin monomer. In another embodiment, the composition(s) disclosed herein can comprise substantially hydrogenated olefin oligomers, wherein the olefin oligomers can be oligomers of one or more olefin monomers, the olefin monomers comprising a branched $C_{10}$ olefin monomer. Herein the term "substantially hydrogenated olefin oligomers" refers to olefin oligomers which have been substantially hydrogenated in a step separate from the step which produced the olefin oligomers. Generally, olefin oligomers have at least two monomeric units, and the properties of olefin oligomers can vary significantly with the removal of one or a few of the monomeric units. By contrast, polymers generally have at least hundreds or thousands of monomeric units, and the properties of polymers do not vary with the removal of one or a few of the monomeric units. Further, olefin oligomers can be dimers (i.e., olefin oligomers incorporating two and only two olefin monomeric units), trimers (i.e., olefin oligomers incorporating three and only three monomeric units), tetramers (i.e., olefin oligomers incorporating four and only four monomeric units), pentamers (i.e., olefin oligomers incorporating five and only five monomeric units), and/or higher oligomers. As will be appreciated by one of skill in the art, and with the help of this disclosure, olefin oligomers can have monomeric units that are the same, or olefin oligomers can have monomeric units that are different. For example, a dimer can have two monomeric units that are the same, or a dimer can have two different monomeric units. Further, for example, a trimer can have three monomeric units that are the same; a trimer can have two monomeric units that are the same but different from the third monomeric unit; or a trimer can have three monomeric units which are all different from each other. For purposes of the disclosure herein, the term "olefin oligomers" refers to molecules that have been obtained by oligomerization of olefins (i.e., process of converting one or more olefin monomers into an olefin oligomer).

In an embodiment, the composition(s) disclosed herein can comprise olefin oligomers of one or more olefin monomers, the olefin monomers comprising a branched $C_{10}$ olefin monomer. In another embodiment, the composition(s) disclosed herein can comprise substantially hydrogenated olefin oligomers, wherein the olefin oligomers can be oligomers of one or more olefin monomers, the olefin monomers comprising a branched $C_{10}$ olefin monomer. In some embodiments, the branched $C_{10}$ olefin monomer of the olefin oligomers and/or the substantially hydrogenated olefin oligomers can comprise i) 3-propyl-1-heptene, ii) 4-ethyl-1-octene, iii) 5-methyl-1-nonene, or iv) any combination thereof. In another embodiment, the branched $C_{10}$ olefin monomer of the olefin oligomers and/or the substantially hydrogenated olefin oligomers can further comprise 2-butyl-1-hexene (i.e., the branched $C_{10}$ olefin monomer can comprise 2-butyl-1-hexene, and i) 3-propyl-1-heptene, ii) 4-ethyl-1-octene, iii) 5-methyl-1-nonene, or iv) any combination thereof). As will be appreciated by one of skill in the art, and with the help of this disclosure, the olefin monomers (branched or linear) can be distributed throughout the total of all of the oligomers of the olefin oligomers in a particular olefin oligomer composition. That is to say, while the total of all of the oligomers in such particular olefin oligomer composition will comprise each of the olefin monomers, an individual olefin oligomer can comprise a single olefin monomer or at least two different olefin monomers. For example, while the total of all of the dimers of the olefin oligomers will comprise each of the olefin monomers, an individual olefin dimer can comprise a single olefin monomer or two different olefin monomers. As another example, while the total of all of the tetramers of the olefin oligomers of the olefin oligomers will comprise each of the olefin monomers, an individual olefin tetramer can comprise one, two, three, or four different olefin monomers.

Aspects and embodiments of olefin monomers are described herein (e.g., identity and molar amounts of specific olefin monomers and molar ratios of specific olefin monomers, among other olefin monomers features). These olefin monomers embodiments can be used without limitation and in any combination to further describe any of the olefin oligomers described herein or any of the substantially hydrogenated olefin oligomers described herein.

In an embodiment, the olefin monomers can comprise, can consist essentially of, or can be, branched $C_{10}$ olefin monomers comprising i) 3-propyl-1-heptene, ii) 4-ethyl-1-octene, iii) 5-methyl-1-nonene, or iv) any combination thereof. In some embodiments, the branched $C_{10}$ olefin monomer can further comprise 2-butyl-1-hexene. In an embodiment, the olefin monomers can comprise at least 20 mol %, at least 30 mol %, at least 40 mol %, at least 50 mol %, at least 60 mol %, at least 65 mol %, at least 70 mol %, at least 75 mol %, at least 80 mol %, or at least 85 mol % of the branched $C_{10}$ olefin monomer.

In an embodiment, the branched $C_{10}$ olefin monomers can comprise, can consist essentially of, or can be, 2-butyl-1-hexene, 3-propyl-1-heptene, 4-ethyl-1-octene, and 5-methyl-1-nonene. In an embodiment, the branched $C_{10}$ olefin monomers can comprise i) at least 10 mol %, at least 11 mol %, at least 12 mol %, at least 13 mol %, or at least 14 mol % 3-propyl-1-heptene; ii) at least 7 mol %, at least 8 mol %, at least 9 mol %, at least 10 mol %, or at least 11 mol % 4-ethyl-1-octene; iii) at least 24 mol %, at least 26 mol %, at least 28 mol %, at least 30 mol %, or at least 32 mol % 5-methyl-1-nonene; and iv) at least 3 mol %, at least 4 mol %, at least 5 mol %, at least 6 mol %, or at least 7 mol % 2-butyl-1-hexene.

In an embodiment, the branched $C_{10}$ olefin monomers can comprise from 10 mol % to 32 mol %, from 11 mol % to 30 mol %, from 12 mol % to 28 mol %, from 13 mol % to 26 mol %, or from 14 mol % to 24 mol % 3-propyl-1-heptene. In an embodiment, the branched $C_{10}$ olefin monomers can comprise from 7 mol % to 25 mol %, from 8 mol % to 24 mol %, from 9 mol % to 23 mol %, from 10 mol % to 22 mol %, or from 11 mol % to 21 mol % 4-ethyl-1-octene. In an embodiment, the branched $C_{10}$ olefin monomers can comprise from 24 mol % to 52 mol %, from 26 mol % to 50 mol %, from 28 mol % to 48 mol %, from 30 mol % to 46 mol %, or from 32 mol % to 44 mol % 5-methyl-1-nonene. In an embodiment, the branched $C_{10}$ olefin monomers can comprise from 3 mol % to 20 mol %, from 4 mol % to 18 mol %, from 5 mol % to 17 mol %, from 6 mol % to 16 mol %, or from 7 mol % to 15 mol % 2-butyl-1-hexene.

In an embodiment, the branched $C_{10}$ olefin monomers can comprise i) from 10 mol % to 32 mol %, from 11 mol % to 30 mol %, from 12 mol % to 28 mol %, from 13 mol % to 26 mol %, or from 14 mol % to 24 mol % 3-propyl-1-heptene; ii) from 7 mol % to 25 mol %, from 8 mol % to 24 mol %, from 9 mol % to 23 mol %, from 10 mol % to 22 mol %, or from 11 mol % to 21 mol % 4-ethyl-1-octene; iii) from 24 mol % to 52 mol %, from 26 mol % to 50 mol %, from 28 mol % to 48 mol %, from 30 mol % to 46 mol %, or from 32 mol % to 44 mol % 5-methyl-1-nonene; and iv) from 3 mol % to 20 mol %, from 4 mol % to 18 mol %, from 5 mol % to 17 mol %, from 6 mol % to 16 mol %, or from 7 mol % to 15 mol % 2-butyl-1-hexene.

In an embodiment, the branched $C_{10}$ olefin monomers can have a molar ratio of 5-methyl-1-nonene to 3-propyl-1-heptene of at least 1.2:1, at least 1.4:1, at least 1.6:1, or at least 1.8:1. In an embodiment, the branched $C_{10}$ olefin monomers can have molar ratio of 5-methyl-1-nonene to 4-ethyl-1-octene of at least 1.6:1, at least 1.7:1, at least 1.9:1, or at least 2.1:1. In some embodiments, the branched $C_{10}$ olefin monomers can have a molar ratio of 5-methyl-1-nonene to 2-butyl-1-hexene of at least 2:1, at least 2.4:1, at least 2.6:1, or at least 2.8:1. In other embodiments, the branched $C_{10}$ olefin monomers can have a molar ratio of 5-methyl-1-nonene to 2-butyl-1-hexene of at least 2:1, at least 2.4:1, at least 2.6:1, or at least 2.8:1; a molar ratio of 5-methyl-1-nonene to 3-propyl-1-heptene of at least 1.2:1, at least 1.4:1, at least 1.6:1, or at least 1.8:1; and a molar ratio of 5-methyl-1-nonene to 4-ethyl-1-octene of at least 1.6:1, at least 1.7:1, at least 1.9:1, or at least 2.1:1.

In an embodiment, the olefin monomers can further comprise linear internal $C_{10}$ olefin monomers, linear internal $C_{14}$ olefin monomers, branched $C_{14}$ olefin monomers, $C_6$ to $C_{18}$ linear olefin monomers, or any combination thereof. In some embodiments, the olefin monomers can comprise, or can consist essentially of, $C_{10}$ branched olefins olefin, linear internal $C_{10}$ olefin monomers, linear internal $C_{14}$ olefin monomers, and branched $C_{14}$ olefin monomers; alternatively, $C_{10}$ branched olefins, linear internal $C_{10}$ olefin monomers, linear internal $C_{14}$ olefin monomers, branched $C_{14}$ olefin monomers, and $C_6$ to $C_{18}$ linear olefin monomers; or alternatively, $C_{10}$ branched olefins olefin, linear internal $C_{10}$ olefin monomers, linear internal $C_{14}$ olefin monomers, branched $C_{14}$ olefin monomers, and $C_6$ to $C_{18}$ normal alpha olefin monomers. The linear internal $C_{10}$ olefin monomers, the linear internal $C_{14}$ olefin monomers, the branched $C_{14}$ olefin monomers, the $C_6$ to $C_{18}$ linear olefin monomers, and the $C_6$ to $C_{18}$ normal alpha olefin monomers and their amount that can be contained in the olefins monomers, are independently described herein and can be used, without limitation, and in any combination with the descriptions of the branched $C_{10}$ olefin monomers described herein, to further describe the olefin monomers.

In an embodiment, the olefin monomers can further comprise linear internal $C_{10}$ olefin monomers. In an embodiment, the olefin monomers can have a molar ratio of linear internal $C_{10}$ olefin monomer to branched $C_{10}$ olefin monomer of from 0.10:1 to 0.16:1; from 0.11:1 to 0.15:1; or from 0.12:1 to 0.14:1. In an embodiment, the linear internal $C_{10}$ olefin monomers can be selected from 4-decene, 5-decene, or any combination thereof. In an embodiment, the linear internal $C_{10}$ olefin monomers can comprise, can consist essentially of, or can be, 4-decene, 5-decene, or any combination thereof; alternatively, 4-decene; or alternatively, 5-decene.

In an embodiment, the olefin monomers can further comprise linear internal $C_{14}$ olefin monomers, branched $C_{14}$ olefin monomers, or any combination thereof. In such embodiment, the olefin monomers can have a molar ratio of linear internal $C_{14}$ olefin monomers and/or branched $C_{14}$ olefin monomers to branched $C_{10}$ olefin monomers from 0.05:1 to 0.12:1; from 0.06:1 to 0.11:1; or from 0.07:1 to 0.1:1.

In an embodiment, it can be desirable to have an olefin monomer comprising a proportion of linear olefin monomer. Thus, in some embodiments, the olefin monomers can further comprise at least one $C_6$ to $C_{18}$ linear olefin monomer. In an embodiment, the olefin monomers can comprise a maximum of 75 mol %, 70 mol %, 65 mol %, 60 mol %, 50 mol %, 40 mol %, 30 mol %, 25 mol %, 20 mol %, 15 mol %, 10 mol %, or 5 mol % of the $C_6$ to $C_{18}$ linear olefin monomers. In some embodiments, the $C_6$ to $C_{18}$ linear olefin monomers can comprise any linear olefin monomer disclosed herein. In an embodiment, the $C_6$ to $C_{18}$ linear olefin monomer can comprise, can consist essentially of, or can be, a hexene, an octene, a decene, a dodecene, a tetradecene, a hexadecene, an octadecene, or any combination thereof; alternatively, an octene, a decene, a dodecene, or any combination thereof; alternatively, an octene; alternatively, a decene; or alternatively, a dodecene.

In an embodiment, it can be desirable to have an olefin monomer comprising a proportion of normal alpha olefin monomer. Thus, in some embodiments, the linear olefin monomer (e.g., $C_6$ to $C_{18}$ linear olefin monomer) can be a normal alpha olefin monomer (e.g., $C_6$ to $C_{18}$ normal alpha olefin monomer). In some embodiments, the olefin monomers can comprise at least one $C_6$ to $C_{18}$ normal alpha olefin monomer. In an embodiment, the $C_6$ to $C_{18}$ normal alpha olefin monomer can comprise, can consist essentially of, or can be, 1-hexene, 1-octene, 1-decene, 1-dodecene, 1-tetradecene, 1-hexadecene, 1-octacene, or any combination thereof; alternatively, 1-octene, 1-decene, 1-dodecene, or any combination thereof; alternatively, 1-octene; alternatively, 1-decene; or alternatively, 1-dodecene. In an embodiment, the olefin monomers can comprise a maximum of 75 mol %, 70 mol %, 65 mol %, 60 mol %, 50 mol %, 40 mol %, 30 mol %, 25 mol %, 20 mol %, 15 mol %, 10 mol %, 8 mol %, 7 mol %, 6 mol %, or 5 mol % of the $C_6$ to $C_{18}$ normal alpha olefin monomers.

A composition comprising branched $C_{10}$ olefins which can be utilized to provide all or a part of the olefin monomers for the olefin oligomers and/or the substantially hydrogenated olefin oligomers disclosed herein is described in more detail in International Application No. PCT/US2015/040433 filed on Jul. 14, 2015.

In a particular non-limiting aspect of the compositions comprising olefin oligomers (or the compositions comprising substantially hydrogenated olefin oligomers), the olefin monomers of the olefin oligomers (or the substantially hydrogenated olefin oligomers, respectively) can comprise at least 80 mol % (or at least 85 mol %) branched $C_{10}$ olefin monomer. In some embodiments of the composition comprising olefin oligomers (or the composition comprising substantially hydrogenated olefin oligomers), the olefin monomers of the olefin oligomers (or the substantially hydrogenated olefin oligomers, respectively) can comprise 1) at least 80 mol % (or at least 85 mol %) of branched $C_{10}$ olefin monomer, and 2) linear internal $C_{10}$ olefin monomer. In other embodiments of the composition comprising olefin oligomers (or the composition comprising substantially hydrogenated olefin oligomers), the olefin monomers of the olefin oligomers (or the substantially hydrogenated olefin oligomers, respectively) can comprise 1) at least 80 mol % (or at least 85 mol %) of branched $C_{10}$ olefin monomer, 2) linear internal $C_{10}$ olefin monomer, and 3) 1-decene. The branched $C_{10}$ olefin monomers, the mol % of the branched $C_{10}$ olefin monomer, the particular branched $C_{10}$ olefin monomers, the mol % of the particular branched $C_{10}$ olefin monomers, the ratios of the branched $C_{10}$ olefin monomers, and the molar ratio of linear internal $C_{10}$ olefin monomer (or 4-decene and/or 5-decene) to branched $C_{10}$ olefin monomer have been described herein and can be utilized without limitation to further describe the olefin monomers for these aspects of the compositions comprising olefin oligomers (or the compositions comprising substantially hydrogenated olefin oligomers). In an embodiment of these aspects, the olefin monomers can comprise less than or equal to 16 mol %, less than or equal to 14 mol %, less than or equal to 12 mol %, less than or equal to 10 mol %, or less than or equal to 8 mol % linear internal $C_{10}$ olefin monomers (or alternatively, 4-decene and/or 5-decene). In any appropriate embodiment of these aspects, the olefin monomers can comprise from 1 mol % to 16 mol %, from 2 mol % to 15 mol %, from 3 mol % to 14 mol %, from 4 mol % to 13 mol %, or from 6 mol % to 12 mol % linear internal $C_{10}$ olefin monomers (or alternatively, 4-decene and/or 5-decene). In any suitable embodiment of these aspects, the olefin monomers can comprise 1-decene monomer in an amount of less than or equal to 10 mol %, less than or equal to 9 mol %, less than or equal to 8 mol %, less than or equal to 7 mol %, or less than or equal to 6 mol % 1-decene; or alternatively from 0.5 mol % to 9 mol %, from 1 mol % to 8 mol %, from 1.5 mol % to 7 mol %, or from 2 mol % to 6 mol % 1-decene.

In another particular non-limiting aspect of the compositions comprising olefin oligomers (or the compositions comprising substantially hydrogenated olefin oligomers), the olefin monomers of the olefin oligomers (or the substantially hydrogenated olefin oligomers, respectively) can comprise 1) at least 70 mol % (or at least 75 mol %) branched $C_{10}$ olefin monomer, 2) linear internal $C_{10}$ olefin monomer, 3) 1-decene, and 4) linear internal $C_{14}$ olefin monomers, branched $C_{14}$ olefin monomers, or any combination thereof. In an embodiment of this aspect, the olefin monomers of these particular compositions can further comprise 1-octene monomer and/or internal $C_{12}$ monomer. The branched $C_{10}$ olefin monomers, the mol % of the branched $C_{10}$ olefin monomer, the particular branched $C_{10}$ olefin monomers, the mol % of the particular branched $C_{10}$ olefin monomers, the ratios of the branched $C_{10}$ olefin monomers, the molar ratio linear internal $C_{10}$ olefin monomer (or 4-decene and/or 5-decene) to branched $C_{10}$ olefin monomer, and the molar ratio of linear internal $C_{14}$ olefin monomers and/or branched $C_{14}$ olefin monomers to branched $C_{10}$ olefin monomers have been described herein and can be utilized without limitation to further describe the olefin monomers for these particular aspects of the compositions comprising olefin oligomers (or the compositions comprising substantially hydrogenated olefin oligomers). In these particular aspects, the olefin monomers can comprise 1-decene monomer in an amount of less than or equal to 10 mol %, less than or equal to 9 mol %, less than or equal to 8 mol %, less than or equal to 7 mol %, or less than or equal to 6 mol % 1-decene; or alternatively from 0.5 mol % to 9 mol %, from 1 mol % to 8 mol %, from 1.5 mol % to 7 mol %, or from 2 mol % to 6 mol % 1-decene. In these particular aspects, the olefin monomers can comprise 1-octene monomer in an amount from 0.1 mol % to 5 mol %, from 0.25 mol % to 4 mol %, or from 0.5 mol % to 3 mol % 1-octene. In these particular aspects, the olefin monomers can comprise internal $C_{12}$ olefin monomers in an amount from 0.1 mol % to 5 mol %, from 0.25 mol % to 4 mol %, or from 0.5 mol % to 3 mol % internal $C_{12}$ olefin monomers.

In yet another particular non-limiting aspect of the compositions comprising olefin oligomers (or the compositions comprising substantially hydrogenated olefin oligomers), the olefin monomers of the olefin oligomers (or the substantially hydrogenated olefin oligomers, respectively) can comprise 1) branched $C_{10}$ olefin monomer, and 2) linear olefin monomer (or normal alpha olefin monomer). In an embodiment of this aspect, the compositions comprising olefin oligomers (or the compositions comprising substantially hydrogenated olefin oligomers), the olefin monomers of the olefin oligomers (or the substantially hydrogenated olefin oligomers, respectively) can comprise 1) branched $C_{10}$ olefin monomer, 2) linear olefin monomer (or normal alpha olefin monomer), and 3) linear internal $C_{10}$ olefin monomer (or 4-decene, 5-decene, or any combination thereof). In another embodiment of this aspect, the compositions comprising olefin oligomers (or the compositions comprising substantially hydrogenated olefin oligomers), the olefin monomers of the olefin oligomers (or the substantially hydrogenated olefin oligomers, respectively) can comprise 1) branched $C_{10}$ olefin monomer, 2) linear olefin monomer (or normal alpha olefin monomer), 3) linear internal $C_{10}$ olefin monomer (or 4-decene, 5-decene, or any combination thereof), and 4) linear internal $C_{14}$ olefin monomers, branched $C_{14}$ olefin monomers, or any combination thereof. The branched $C_{10}$ olefin monomers, the mol % of the branched $C_{10}$ olefin monomer, the particular branched $C_{10}$ olefin monomers, the mol % of the particular branched $C_{10}$ olefin monomers, the ratios of the branched $C_{10}$ olefin monomers, the mol % of the linear olefin monomer (or normal alpha olefin monomer), the particular linear olefin monomer (or particular normal alpha olefin monomer), the molar ratio linear internal $C_{10}$ olefin monomer (or 4-decene and/or 5-decene) to branched $C_{10}$ olefin monomer, and the molar ratio of linear internal $C_{14}$ olefin monomers and/or branched $C_{14}$ olefin monomers to branched $C_{10}$ olefin monomers have been described herein and can be utilized without limitation to further describe the olefin monomers for the appropriate embodiments and/or aspects of the compositions comprising olefin oligomers (or the compositions comprising substantially hydrogenated olefin oligomers).

In an embodiment, the olefin oligomers (or any portion thereof) and/or the substantially hydrogenated olefin oligomers (or any portion thereof) disclosed herein can have a 100° C. kinematic viscosity of from 1.5 cSt to 225 cSt, from 1.5 cSt to 12 cSt, from 15 cSt to 40 cSt, or from 40 cSt to 150 cSt. In an embodiment, a composition consisting essentially of, or consisting of, the olefin oligomers (or any portion thereof) and/or the substantially hydrogenated olefin oligomers (or any portion thereof) disclosed herein can have a 100° C. kinematic viscosity of from 1.5 cSt to 225 cSt, from 1.5 cSt to 12 cSt, from 15 cSt to 40 cSt, or from 40 cSt to 150 cSt. Generally, the viscosity of a fluid (e.g., any olefin oligomers and/or any substantially hydrogenated olefin oligomers disclosed herein) is a measure of its resistance to gradual deformation (e.g., flow) by shear stress at a given temperature. Kinematic viscosity generally refers to the ratio of viscosity to density for a particular fluid at a given temperature. The 100° C. kinematic viscosity of the compositions described herein can be measured using ASTM D445-12.

In some embodiments, the olefin oligomers (or any portion thereof) and/or the substantially hydrogenated olefin oligomers (or any portion thereof) disclosed herein can have a 100° C. kinematic viscosity of from 1.8 cSt to 2.2 cSt, from 2.3 cSt to 2.7 cSt, from 2.6 cSt to 3.4 cSt, from 3.6 cSt to 4.4 cSt, from 4.6 cSt to 5.4 cSt, from 5.6 cSt to 6.4 cSt, from 6.6 cSt to 7.4 cSt, from 7.6 cSt to 8.4 cSt, from 8.6 cSt to 9.4 cSt, or from 9.6 cSt to 10.4 cSt.

In an embodiment, the substantially hydrogenated olefin oligomers (or any portion thereof) described herein can have bromine number of less than 2, less than 1.8, less than 1.6, less than 1.4, less than 1.2, or less than 1 g Br/100 g substantially hydrogenated olefin oligomers, as determined in accordance with ASTM D1159-09. Generally, the bromine number is a measure of the degree of unsaturation of a sample or composition, and is generally expressed as the amount of bromine in grams absorbed by 100 g of sample or composition. In other embodiments, the substantially hydrogenated olefin oligomers (or any portion thereof) described herein can have a bromine index of less than 1000, less than 800, less than 600, or less than 500 mg Br/100 g substantially hydrogenated olefin oligomers, as determined in accordance with ASTM D2710-09. Generally, the bromine index is also a measure of the degree of unsaturation of a sample or composition, and is generally expressed as the amount of bromine in milligrams absorbed by 100 g of sample or composition.

Generally, the compositions disclosed herein can be prepared by processes including an oligomerization step. In an embodiment, the process can comprise a) contacting 1) a catalyst system and 2) a monomer feedstock (e.g., olefin monomers) comprising a branched $C_{10}$ olefin monomer in a reaction zone; and b) forming olefin oligomers. In some embodiments, the process can comprise a) contacting 1) a catalyst system and 2) a monomer feedstock (e.g., olefin monomers) comprising a branched $C_{10}$ olefin monomer in a reaction zone; b) forming olefin oligomers; and c) isolating a composition comprising olefin oligomers. In another embodiment, the process can comprise a) contacting 1) a catalyst system and 2) a monomer feedstock (e.g., olefin monomers) comprising a branched $C_{10}$ olefin monomer in a reaction zone; b) forming olefin oligomers; c) isolating a first composition comprising olefin oligomers; and d) hydrogenating at least a portion of the first composition to yield a second composition comprising substantially hydrogenated olefin oligomers. In an embodiment, the process can comprise a) contacting 1) a catalyst system and 2) a monomer feedstock (e.g., olefin monomers) comprising a branched $C_{10}$ olefin monomer comprising i) 3-propyl-1-heptene, ii) 4-ethyl-1-octene, iii) 5-methyl-1-nonene, or iv) any combination thereof in a reaction zone; b) forming olefin oligomers; and c) removing a reaction zone effluent from the reaction zone. In an embodiment, the reaction zone effluent can be contacted with a catalyst system deactivating agent to form a deactivated reaction zone effluent. In some embodiments, one or more fractions comprising all or a portion of the olefin oligomers of the reaction zone effluent and/or deactivated reaction zone effluent can be isolated from the reaction zone effluent and/or deactivated reaction zone effluent, respectively. In a further embodiment, at least one of the one or more fractions comprising all or a portion of the olefin oligomers of the reaction zone effluent and/or deactivated reaction zone effluent can be hydrogenated (e.g., subjected to hydrogenation). In yet a further embodiment, one or more fractions from the hydrogenated one or more fractions comprising all or a portion of the olefin oligomers of the reaction zone effluent and/or deactivated reaction zone effluent can be isolated. Features and aspects of the processes, including but not limited to, the catalyst system, the monomer feedstock (e.g., olefin monomer), the reaction zone, the olefin oligomer, the conditions for forming the olefin oligomers, steps for processing a reaction zone effluent, steps of isolating a first composition comprising olefin oligomers, steps for isolating one or more fractions comprising all or a portion of the olefin oligomers from the reaction zone effluent and/or deactivated reaction zone effluent, steps for hydrogenating at least a portion of the first composition to yield a second composition comprising substantially hydrogenated olefin oligomers, steps for hydrogenating at least one of the one or more fractions comprising all or a portion of the olefin oligomers of the reaction zone effluent and/or deactivated reaction zone effluent, steps for isolating at least one of the one or more fractions comprising all or a portion of the olefin oligomers from the reaction zone effluent and/or deactivated reaction zone effluent, properties of the olefin oligomers, properties of any one of the one or more fractions of the olefin oligomers, properties of the substantially hydrogenated olefin oligomers, and properties of any one of the one or more fractions from the hydrogenated one or more fractions comprising all or a portion of the olefin oligomers of the reaction zone effluent and/or deactivated reaction zone effluent are independently disclosed herein and these aspects and embodiments can be utilized without limitation and in any combination to further describe the processes disclosed herein. In relation to the monomer feedstock, the monomer feedstock for any of the processes described herein can be any of the olefin monomers comprising branched $C_{10}$ olefin monomers of the composition comprising olefin oligomers (or the composition comprising substantially hydrogenated olefin oligomers) described herein.

For purposes of the disclosure herein, the term "reaction zone" refers to a portion of a process, associated equipment and associated process lines where all necessary reaction components and reaction conditions are present such that a reaction (e.g., oligomerization reaction, olefin oligomerization, etc.) can occur at a desired rate. For purposes of the disclosure herein, the reaction zone can comprise one or more reactors, and/or associated equipment where all the necessary reaction components and reaction conditions are present such that the reaction can occur at a desired rate.

Generally, the monomer feedstock can comprise the olefin monomers from which the olefin oligomers (or substantially hydrogenated olefin oligomers) are formed. In an embodiment, the monomer feedstock can comprise, can consist essentially of, or can be, any olefin monomer(s) previously disclosed herein which can form the olefin oligomers. In an embodiment, a composition containing the monomer feedstock can further comprise components which are not olefins and/or are not incorporated into the olefin oligomer. In some embodiments, the composition containing the monomer feedstock can contain a variety of non-olefin impurities, such as saturated hydrocarbons (e.g., acyclic saturated hydrocarbons, cyclic saturated hydrocarbons), aromatic hydrocarbons, alcohols, or combination thereof. Non-limiting examples of non-olefin impurities which could be present in the composition containing the monomer feedstock can include $C_{8-14}$ alkanes, cyclohexane, methylcyclopentane, methylcyclohexane, benzene, toluene, ethylbenzene, xylene, mesitylene, hexamethylbenzene, $C_{4-12}$ alcohols, 2-ethyl-1-hexanol, and 2-ethylhexyl-2-ethylhexanoate, or any combination thereof. Generally, the composition comprising the monomer feedstock can comprise an maximum of 10 wt. %, 7.5 wt. %, 5 wt. %, 4 wt. %, or 3 wt. %, based upon the weight of the olefins in the monomer feedstock of these non-olefin impurities. International Application No. PCT/US2015/040433 filed on Jul. 14, 2015 describes compositions containing branched $C_{10}$ olefins which can be utilized to provide all or a part of the olefin monomers of the olefin feedstock for the processes described herein.

Generally, the processes disclosed herein, can employ any catalyst or catalyst system which can oligomerize the olefin monomer of the olefin feedstock to form the olefin oligomer.

In an embodiment, the catalyst system can comprise, consist essentially of, or consist of, a Lewis acid. In some embodiments, the catalyst system can comprise, consist essentially of, or consist of, a Lewis acid and a promoter. When a promoter is utilized, the promoter can be introduced as a component of the catalyst mixture; alternatively, can be introduced with the monomer; or alternatively, can be introduced as a separate component to the processes described herein.

Generally, a Lewis acid refers to a chemical species that can accept a pair of electrons in a particular chemical reaction or process. Non-limiting examples of Lewis acids suitable for use in the present disclosure include a boron trihalide, an aluminum halide compound, a titanium halide, an iron halide, a gallium halide, a tin halide, or combinations thereof; alternatively, a boron trihalide; or alternatively, an aluminum halide compound. In an embodiment, each halide of any halide containing Lewis acid described herein can be fluoride, chloride, bromide, or iodide; alternatively, chloride, bromide, or iodide; alternatively, chloride or bromide; alternatively, chloride or iodide; alternatively, bromide or iodide; alternatively, fluoride; alternatively chloride, or alternatively, bromide.

Generally, the aluminum halide compound which can be utilized as the Lewis acid can be any aluminum halide compound which can oligomerize the olefin monomer either in the presence of a promoter or in the absence of a promoter. In an embodiment, the aluminum halide compound can have the formula $R_yAlX_{3-y}$, wherein R can be a hydrocarbyl group (or an alkyl group), X can be any halide described herein, and y can range from 0 to 3. Further features and embodiments of the aluminum halide compound (including features and embodiments of aluminum trihalides, hydrocarbylaluminum halides, and alkylaluminum halides) are described herein and these features and embodiments can be utilized without limitation and in any combination to further describe the aluminum halide compound which can be utilized in the processes described herein.

In some particular embodiments, the Lewis Acid can comprise, consist essentially of, or consist of, $BF_3$, $BCl_3$, $AlCl_3$, $AlBr_3$, $TiCl_3$, $TiBr_3$, $TiCl_4$, $TiBr_4$, $SnCl_4$, $GaCl_3$, $GaBr_3$, $FeCl_3$, $FeBr_3$, or any combination thereof; alternatively, $BF_3$, $AlCl_3$, $AlBr_3$, $TiCl_3$, $TiCl_4$, or any combination thereof; alternatively, $BF_3$; alternatively, $AlCl_3$; alternatively, $AlBr_3$; alternatively, $TiCl_3$; or alternatively, $TiCl_4$. In other embodiments, the Lewis acid can be synthetic or natural zeolites, acid clays, polymeric acidic resins, amorphous solid catalysts such as silica-alumina, and heteropolyacids such as tungsten zirconates, tungsten molybdates, tungsten vanadates, phosphotungstates and molybdotungstovanadogermanates (e.g., $WOx/ZrO_2$, $WOx/MoO_3$).

The amount of the Lewis acid utilized in the processes disclosed herein can be any amount which promotes the formation of the olefin oligomers and/or allows the oligomerization to proceed at a reasonable rate. A useful of amount of Lewis acid can range from 0.0001 moles or 0.005 moles to 0.20 moles or 0.03 moles of Lewis acid per mole of olefin monomer. The temperature at which the olefin oligomers can be formed using a Lewis acid catalyst or a Lewis acid catalyst system can range from 0° C., 10° C. or 20° C. to 300° C., 200° C., 150° C., 100° C., 75° C., or 60° C. The pressure at which the olefin oligomers can be formed using a Lewis acid catalyst or a Lewis acid catalyst system can range from 0 psig (101 kPa) or 5 psig (135 kPa) to 725 psig (5 MPa) or 50 psig (441 kPa), Generally, the promoter can be any compound which can provide a more desirable rate of formation of the olefin oligomers (or rate of monomer oligomerization) when compared to a rate in the absence of the promoter and/or can provide a more desirable oligomer distribution when compared to an oligomer distribution in the absence of the promoter. Non-limiting examples of promoters suitable for use in the present disclosure include water, alcohols, carboxylic acids, carboxylic acid esters, carboxylic acid anhydrides, aldehydes, ketones, ethers, organohalides (e.g., alkyl halides), mineral acids (e.g., HCl, HBr, $H_2SO_4$, $HNO_3$ $HPO_4$, among others), or any combination thereof. The amount of promoter employed utilized in the processes utilizing a Lewis acid and a promoter can range of from 0.0001 moles or 0.0025 moles to 0.20 moles or 0.025 moles per mole of olefin monomer employed. General and specific examples of the promoters are disclosed herein and can be utilized without limitation to further describe any catalyst system utilizing a promoter.

In an embodiment, the catalyst system can be selected from the group consisting of (a) a catalyst system comprising $BF_3$, (b) a catalyst system comprising an alkylaluminum halide, an aluminum trihalide, or any combination thereof, (c) a supported metal oxide, (d) a catalyst system comprising an acidic ionic liquid, (e) a catalyst system comprising a metallocene, (f) a catalyst system comprising a clay, an acidic clay, or an acid washed clay, and (g) an acidic ion exchange resin. In some embodiments, the catalyst system can comprise $BF_3$; alternatively, an alkylaluminum halide, an aluminum trihalide, or any combination thereof; alternatively, a supported metal oxide; alternatively, an acidic ionic liquid; alternatively, a metallocene; alternatively, a catalyst system comprising a clay, an acidic clay, or an acid washed clay; or alternatively, an acidic ion exchange resin. In other embodiments, the catalyst system can comprise a supported metal oxide.

In an embodiment, the catalyst system can comprise, or can consist essentially of, $BF_3$. In some embodiments, the catalyst system can comprise (a) $BF_3$ and (b) a promoter. In some embodiments, the promoter can be selected from the group consisting of water, alcohols, carboxylic acids, carboxylic acid esters, carboxylic acid anhydrides, aldehydes, ketones, ethers, organohalides (e.g., alkyl halides), and any combination thereof. General and specific examples of the promoters are disclosed herein and can be utilized without limitation to further describe any catalyst system comprising $BF_3$ and a promoter. General and specific examples of alcohol promoters are disclosed herein and can be utilized without limitation to further describe any catalyst system comprising $BF_3$ and an alcohol promoter. In other particular embodiments, the promoter can be a combination of an alcohol and a carboxylic acid ester. When the promoter utilized is a combination of an alcohol and a carboxylic acid ester, the alcohol can be any general or specific alcohol described herein and the carboxylic acid ester can be any general or specific carboxylic acid ester disclosed herein.

Generally, the quantity of $BF_3$ that can be utilized in processes utilizing $BF_3$ or $BF_3$ and a promoter can be any quantity that can allow the olefin oligomerization to proceed at a reasonable rate and/or produce a desired olefin oligomer distribution. In an embodiment, the processes can utilize a $BF_3$ partial pressure from 2 psi (13.8 kPa) to 1000 psi (6.89 MPa), from 2 psi (13.8 kPa) to 500 psi (3.45 MPa), from 10 psi (68.6 kPa) to 500 psi (3.45 MPa), or from 10 psi (68.6 kPa) to 250 psi (1.72 MPa). The quantity of promoter, if utilized can be any quantity that can promote the olefin oligomerization to proceed at a reasonable rate and/or produce a desired olefin oligomer distribution. In an embodiment, the total amount of promoter can be from 0.01 moles alcohol to 7 moles alcohol per mole of olefin, from 0.05 moles alcohol to 5 moles alcohol per mole of olefin, from 0.1 moles alcohol to 3 moles alcohol per mole of olefin, or from 0.2 moles alcohol to 2 moles alcohol per mole of olefin. Generally, the temperature at which the olefin oligomers are formed using a catalyst system comprising, or consisting essentially of, $BF_3$ (or $BF_3$ and a promoter) can be any temperature that can allow the olefin oligomerization to proceed at a reasonable rate and/or produce a desired olefin oligomer distribution. In an embodiment, the olefin oligomer can be formed at a temperature from –20° C. to 150° C., from –20° C. to 100° C., 0° C. to 90° C., from 20° C. to 90° C., or from 20° C. to 70° C. Additional information on the use of a catalyst system comprising BF, can be found in U.S. Pat. Nos. 3,957,664, 4,045,507, 4,045,508, 4,172,855, 4,409,415, 5,498,815, 7,652,186, and 9,206,095 among other patents and patent applications.

In an embodiment, the catalyst system can comprise, consist essentially of, or consist of, an alkylaluminum halide, an aluminum trihalide, or any combination thereof; alternatively, alkylaluminum halide; or alternatively, an aluminum trihalide. In some embodiments, the catalyst system can comprise, consist essentially of, or consist of, (a) an alkylaluminum halide, an aluminum trihalide, or any combination thereof and (b) a promoter; alternatively, (a) an alkylaluminum halide and (b) a promoter; or alternatively, (a) an aluminum trihalide and (b) a promoter. In an embodiment, the promoter can be selected from the group consisting of water, alcohols, carboxylic acids, carboxylic acid esters, carboxylic acid anhydrides, aldehydes, ketones, ethers, organohalides (e.g., alkyl halides), and combinations thereof.

Generally, the alkylaluminum halide and/or aluminum trihalide can be any alkylaluminum halide and/or aluminum trihalide which can oligomerize the olefin monomer in the presence of a promoter or in the absence of a promoter. In an embodiment, the alkylaluminum halide can have the formula $R_yAlX_{3-y}$, wherein R can be a hydrocarbyl group (or an alkyl group), X can be a halide, and y can range from greater than 0 to less than 3; can range from greater than 0 to 2; alternatively, can be about 1; alternatively, can be about 1.5; or alternatively, can be about 2. In an embodiment, the aluminum trihalide can have the formula $AlX_3$, wherein X is a halide. In some embodiments, each halide, X, of the aluminum trihalide and/or the alkylaluminum halide independently can be chloride, bromide, or iodide; alternatively, chloride or bromide; alternatively, chloride or iodide; or alternatively, bromide or iodide.

Each R of any alkylaluminum halide having the formula $R_yAlX_{3-y}$ independently can be a $C_1$ to $C_{10}$ hydrocarbyl group; or alternatively, a $C_2$ to $C_6$ hydrocarbyl group. In an embodiment, the alkylaluminum halide can comprise, consist essentially of, or can be, a hydrocarbylaluminum dihalide, a hydrocarbylaluminum sesquihalide, a dihydrocarbylaluminum halide, or any combination thereof; alternatively, a hydrocarbylaluminum dihalide; alternatively, a hydrocarbylaluminum sesquihalide; or alternatively, a dihydrocarbylaluminum halide. In an embodiment, each R of the alkylaluminum halide independently can be a methyl group, an ethyl group, a propyl group, a butyl group, a pentyl group, a hexyl group, a heptyl group, or an octyl group; alternatively, an ethyl group, an n-butyl group, an iso-butyl group, or a hexyl group; alternatively, an ethyl group; alternatively, an n-butyl group; or alternatively, an iso-butyl group.

In some embodiments, the alkylaluminum halide can be ethylaluminum dichloride, ethylaluminum dibromide, ethylaluminum sesquichloride, ethylaluminum sesquibromide, diethylaluminum chloride, diethylaluminum bromide, or any combination thereof; alternatively, ethylaluminum dichloride, ethylaluminum sesquichloride, diethylaluminum chloride, or any combination thereof; or alternatively, ethylaluminum dibromide, ethylaluminum sesquibromide, diethylaluminum bromide, or any combination thereof. Aluminum trihalides suitable for use as the catalyst or as a component in the catalyst system can comprise, consist essentially of, or consist of, aluminum trichloride, aluminum tribromide, aluminum triiodide, or any combinations thereof; alternatively, aluminum trichloride, aluminum tribromide, or any combinations thereof; alternatively, aluminum trichloride; or alternatively, aluminum tribromide. In an embodiment, the aluminum halide compound (whether it is an aluminum trihalide or alkylaluminum halide) can be substantially devoid of an aluminum halide based ionic liquid. Within this context, substantially devoid of an aluminum halide based ionic liquid means that less than 5 wt. % of the aluminum halide is in the form a low melting organic halogen aluminate salt.

Generally, the alkylaluminum halide and/or the aluminum trihalide to monomer molar ratio can be any ratio which can provide desirable olefin oligomers. In an embodiment, the minimum alkylaluminum halide and/or aluminum trihalide to monomer molar ratio can be $5 \times 10^{-8}:1$, $5 \times 10^{-5}:1$, $1 \times 10^{-4}:1$, $2.5 \times 10^{-4}:1$, $5 \times 10^{-4}:1$, $7.5 \times 10^{-4}:1$ or $1 \times 10^{-3}:1$. In an embodiment, the maximum alkylaluminum halide and/or aluminum trihalide to monomer molar ratio can be $3.5 \times 10^{-2}:1$, $3 \times 10^{-2}:1$, $2.5 \times 10^{-2}:1$, $2 \times 10^{-2}:1$, $1.5 \times 10^{-2}:1$, $1 \times 10^{-2}:1$, or $1.1 \times 10^{-2}:1$. In an embodiment, the alkylaluminum halide and/or aluminum trihalide to monomer molar ratio can range from any minimum alkylaluminum halide and/or aluminum trihalide to monomer molar ratio described herein to any maximum alkylaluminum halide and/or aluminum trihalide to monomer molar ratio described herein. Suitable ranges for the alkylaluminum halide and/or aluminum trihalide to monomer molar ratio can include, but are not limited to, from $5 \times 10^{-8}:1$ to $1.1 \times 10^{-2}:1$, from $5 \times 10^{-5}:1$ to $3.5 \times 10^{-2}:1$, from $1 \times 10^{-4}:1$ to $3 \times 10^{2}:1$, from $2.5 \times 10^{-4}:1$ to $2.5 \times 10^{-2}:1$, from $5 \times 10^{-4}:1$ to $2 \times 10^{-2}:1$, from $5 \times 10^{-4}:1$ to $1.5 \times 10^{-2}:1$, from $5 \times 10^{-4}:1$ to $1 \times 10^{-2}:1$, or from $5 \times 10^{4}:1$ to $5 \times 10^{3}:1$. Other suitable alkylaluminum halide and/or aluminum trihalide to monomer molar ratio ranges are readily apparent from the present disclosure.

In an embodiment, stable liquid solutions can be formed between alkylaluminum halides and/or aluminum trihalides and an organic liquid carrier comprising olefins where the organic liquid carrier olefins can comprise, consist essentially of, or consist of, one or more 1,2-disubstituted olefins, trisubstituted olefins, or any combination thereof. Such a stable liquid solution can be prepared in advance of its use and stored for long periods of time. The formation of catalyst mixtures comprising, consisting essentially of, or consisting of, an alkylaluminum halide and/or aluminum trihalides and an organic liquid carrier comprising olefins where the organic liquid carrier olefins comprise, consist essentially of, or consists of, one or more 1,2-disubstituted olefins, trisubstituted olefins, or any combination thereof has an advantage in that the catalyst mixture can thus avoid the addition of solid/powered catalyst (e.g., an aluminum trihalide) to a reaction, does not add unreactive components to a reaction (e.g., oligomerization), and/or the catalyst mixture can be stable for long periods of time. In some embodiments, the catalyst mixture or catalyst system mixture comprising, consisting essentially of, or consisting of, an alkylaluminum halide and/or alkylaluminum halide and an organic liquid carrier comprising olefins where the organic liquid carrier olefins comprises, consists essentially of, or consists of, one or more 1,2-disubstituted olefins, trisubstituted olefins, or any combination thereof can be stored for at least 1 day, 7 days, 14 days, 30 days or 60 days.

In aspects and embodiments utilizing a catalyst system comprising any alkylaluminum halide and/or alkylaluminum halide disclosed herein and including an organic liquid carrier, the organic liquid carrier can comprise, or consist essentially of, olefins. In an embodiment, the organic liquid carrier can comprise at least 50 wt. %, 55 wt. %, wt. %, 65 wt. %, 70 wt. %, 75 wt. %, 80 wt. %, 85 wt. %, 90 wt. %, 92 wt. %, 94 wt. %, or 95 wt. % olefins based upon the total weight of the catalyst system (e.g., catalyst system solution). In an embodiment, the catalyst mixture including an organic liquid carrier, the organic liquid carrier olefins can comprise 1,2-disubstituted olefins, trisubstituted olefins, or any combination thereof; alternatively, 1,2-disubstituted olefins; or alternatively, trisubstituted olefins. In some embodiments, the organic liquid carrier olefins (1,2-disubstituted olefins, trisubstituted olefins, or combination thereof) can be hydrocarbon olefins. In other embodiments, the organic liquid carrier olefins (1,2-disubstituted olefins, trisubstituted olefins, or combination thereof) can be aliphatic olefins. In further embodiments, the organic liquid carrier olefins (1,2-disubstituted olefins, trisubstituted olefins, or combination thereof) can be aliphatic hydrocarbon olefins. In some embodiments, the 1,2-disubstituted olefins which can be utilized as the organic liquid carrier olefins or as part of the organic liquid carrier olefins can comprise, consist essentially of, or consist of, linear 1,2-disubstituted olefins, branched (at a position other than on the olefin carbon-carbon double bond) olefins, or any combination thereof; alternatively, linear 1,2-disubstituted olefins; or alternatively, branched 1,2-disubstittued olefins. In an embodiment, the liquid organic carrier olefins can comprise at least 50 mol %, 55 mol %, 60 mol %, 65 mol %, 70 mol %, 75 mol %, 80 mol %, 85 mol %, 90 mol %, 92 mol %, 94 mol %, or 95 mol % of any 1,2-disubstittued olefin, trisubstituted olefin, or combination thereof described herein. In some embodiments, the liquid organic carrier olefins can comprise a maximum of 10 mol %, 8 mol %, 6 mol %, 5 mol %, 4 mol %, 3 mol %, or 2 mol % of any alpha olefin (or normal alpha olefin). In some embodiments, the liquid organic carrier olefins can comprise a maximum of 50 mol %, 45 mol %, 40 mol %, 35 mol %, 30 mol %, 25 mol %, 20 mol %, 15 mol %, 10 mol %, 8 mol %, 6 mol %, or 5 mol % tetrasubstituted olefins. In some embodiments, the liquid organic carrier olefins can comprise a maximum of 30 mol %, 25 mol %, 20 mol %, 15 mol %, 10 mol %, 8 mol %, 6 mol %, or 5 mol % vinylidenes. In some embodiments, the liquid organic carrier can comprise a maximum of 100 ppm (by weight), 80 ppm, 60 ppm, 50 ppm, 40 ppm, 30 ppm, 20 ppm or 10 ppm water (unless intentionally added as the promoter described herein). In some embodiments, the liquid organic carrier can comprise a maximum of 1000 ppm (by weight), 750 ppm, 500 ppm, 250 ppm, 100 ppm, 80 ppm, 60 ppm, 50 ppm, 40 ppm, 30 ppm, 20 ppm or 10 ppm peroxides (unless intentionally added as the promoter described herein).

Generally, the concentration of the alkylaluminum halide and/or aluminum trihalide in relation to the organic liquid carrier olefins can be any concentration which forms a stable solution with the organic liquid carrier. In an embodiment, the minimum concentration of the alkylaluminum halide and/or aluminum trihalide in the organic liquid carrier olefins can be 0.15 molal (moles catalyst per kg organic liquid carrier), 0.2 molal, 0.4 molal, 0.6 molal, 0.7 molal, 0.8 molal, 0.9 molal, 1.0 molal, 1.1 molal, or 1.2 molal. In an embodiment, the maximum concentration of the alkylaluminum halide and/or aluminum trihalide in the organic liquid carrier olefins can be 4.0 molal, 3.5 molal, 3.0 molal, 2.5 molal, 2.0 molal, 1.8 molal, 1.6 molal, 1.4 molal, 1.2 molal, or 1.0 molal. In an embodiment, the alkylaluminum halide and/or aluminum trihalide concentration in the organic liquid carrier olefins can range from any minimum alkylaluminum halide and/or aluminum trihalide concentration in the organic liquid carrier olefins described herein to any maximum alkylaluminum halide and/or aluminum trihalide concentration in the organic liquid carrier olefins described herein. Suitable ranges for the alkylaluminum halide and/or aluminum trihalide concentration in the organic liquid carrier olefins can include, but are not limited to, from 0.15 molal to 4.0 molal, from 0.4 molal to 4.0 molal, from 0.4 molal to 3.5 molal, from 0.6 molal to 3.5 mol, from 0.6 molal to 3.0 molal, or from 0.8 molal to 2.5 molal. Other suitable alkylaluminum halide and/or aluminum trihalide concentrations in the organic liquid carrier olefins are readily apparent from the present disclosure.

In an aspect, catalyst systems comprising an alkylaluminum halide and/or aluminum trihalide which can be utilized in the processes described herein can include a promoter. Generally, the promoter can be any compound which can provide a more desirable rate of formation of the olefin oligomers (or rate of monomer oligomerization) when compared to the rate in the absence of the promoter and/or can provide a more desirable olefin oligomer distribution when compared to the olefin oligomer distribution in the absence of the promoter. In an embodiment, the promoter can comprise, consist essentially of, or consist of, water, an alcohol, a carboxylic acid, an ester, a ketone, an ether, a halogenated hydrocarbon, or any combination thereof; alternatively, water, an alcohol, a carboxylic acid, an ester, a ketone, an ether, or any combination thereof; alternatively, water, an alcohol, an ester, or any combination thereof; alternatively, water and an alcohol; alternatively, water and a carboxylic acid; alternatively, water and an ester, alternatively, water and a ketone; alternatively, an alcohol and a carboxylic acid; alternatively, an alcohol and an ester; alternatively, an alcohol and a ketone; alternatively, water; alternatively, an alcohol; alternatively, a carboxylic acid; alternatively, an ester; alternatively, a ketone; alternatively, an ester, or alternatively, a halogenated hydrocarbon. Specific promoters within these promoter classes are independently described herein and these specific promoter descriptions can be utilized without limitation to further describe the promoters which can be utilized in the catalyst systems comprising an alkylaluminum halide and/or aluminum trihalide and a promoter.

In another aspect, the catalyst systems comprising an alkylaluminum halide and/or aluminum trihalide which can be utilized in the processes described herein can include a protic promoter. Generally, the protic promoter can be any compound having an acidic proton and can provide a more desirable rate of formation of the olefin oligomers (or rate of monomer oligomerization) when compared to the rate in the absence of the promoter and/or can provide a more desirable oligomer distribution when compared to the oligomer distribution in the absence of the promoter. In an embodiment, the protic promoter can comprise, consist essentially of, or consist of, water, an alcohol, a carboxylic acid, or any combination thereof; alternatively, water and an alcohol; alternatively, water and a carboxylic acid; alternatively, an alcohol and a carboxylic acid; alternatively, water; alternatively, an alcohol; or alternatively, a carboxylic acid. Specific protic promoters within these protic promoter classes are independently described herein and these specific protic promoter descriptions can be utilized without limitation to further describe the acidic promoters which can be utilized in the catalyst systems comprising an alkylaluminum halide and/or aluminum trihalide and a promoter.

In any aspect or embodiment of the alkylaluminum halide and/or aluminum trihalide catalyst or catalyst systems disclosed herein, a metal halide (other than the aluminum halide component utilized as a catalyst, component of the catalyst mixture, or catalyst system mixture), an alkyl metal halide (other than the alkylaluminum halide component utilized as a catalyst, component of the catalyst mixture, or catalyst system mixture), an alkyl metal compound, or any combination thereof can be utilized as a component of the catalyst system or in any process using any alkylaluminum halide and/or aluminum trihalide catalyst or catalyst systems disclosed herein. In an embodiment, the metal halide, the alkyl metal halide, and/or the alkyl metal compound can be a component of the catalyst mixture (or catalyst system mixture); or alternatively, the metal halide, the alkyl metal halide, and/or the alkyl metal compound can be contacted with the catalyst (or catalyst mixture, or catalyst system mixture) and monomer to form the olefin oligomers. Generally, the metal halide can be any compound which can increase the rate of formation of the olefin oligomers (or rate of monomer oligomerization) when compared to the rate in the absence of the metal halide and/or can provide a more desirable oligomer distribution when compared to the oligomer distribution in the absence of the metal halide.

In an embodiment, the metal of the metal halide, alkyl metal halide, and/or the alkyl metal compound utilized as a component of the alkylaluminum halide and/or aluminum trihalide catalyst or catalyst systems can be a Group 4-10 metal; alternatively, a Group 4-8 metal; or alternatively, a Group 4-5 metal. In some embodiments the metal of the metal halide, alkyl metal halide, and/or the alkyl metal compound can be titanium, vanadium, zirconium, chromium, or iron; alternatively, titanium, vanadium, or iron; alternatively, titanium; alternatively, vanadium; or alternatively, iron. In an embodiment, each halide of the metal halide and/or alkyl metal halide independently can be chloride, bromide, or iodide; alternatively, chloride; alternatively, bromide; or alternatively, iodide. In an embodiment, each alkyl group of the alkyl metal halide and/or the alkyl metal compound can be a methyl group, an ethyl group, a propyl group, a butyl group, a pentyl group, a hexyl group, or a heptyl group; alternatively, an ethyl group, an n-butyl group, an iso-butyl group or a hexyl group; alternatively, an ethyl group; alternatively, a n-butyl group; or alternatively, an iso-butyl group. In some embodiments, the metal halide can comprise, consist essentially of, or consist of, titanium trichloride, titanium tetrachloride, vanadium trichloride, vanadium tetrachloride, iron dichloride, or iron trichloride; alternatively, titanium tetrachloride, vanadium tetrachloride, or iron trichloride; or alternatively, titanium tetrachloride. In embodiments where an aluminum trihalide is used, the alkyl metal halide can be an alkylaluminum halide having the formula $R_yAlX_{3-y}$, wherein y can range from greater than 0 to less than 3. Alkylaluminum halides having the formula $R_yAlX_{3-y}$, wherein y can range from greater than 0 to less than 3 (general and specific) are described herein as potential selections for the catalyst and this alkylaluminum halide can be utilized, without limitation, as the alkyl metal halide when the catalyst is aluminum trihalide. In some embodiments, the alkyl metal compound can be a trialkylaluminum compound. Alkyl groups for the alkyl metal compound are described herein and these can be utilized, without limitation, to further describe the trialkylaluminum compound. In some embodiments, the trialkylaluminum compound can comprise, consist essentially, or consist of, triethylaluminum, tributylaluminum, trihexylaluminum, trioctylaluminum, or any combination thereof; alternatively triethylaluminum, tri-n-butylaluminum, tri-isobutylaluminum, or any combination thereof; alternatively, triethyl aluminum; or alternatively, tri-iso-butylaluminum.

Generally, in any aspect or embodiment where a metal halide, alkyl metal halide, and/or the alkyl metal compound is utilized in conjunction with the aluminum halide catalyst, the metal of the metal halide, alkyl metal halide, and/or the alkyl metal compound to aluminum halide molar ratio (metal to aluminum molar ratio) can be any metal to aluminum molar ratio which can provide a more desirable rate of formation of the olefin oligomers (or rate of monomer oligomerization) when compared to the rate in the absence of the metal halide, alkyl metal halide, and/or the alkyl metal compound and/or can provide a more desirable oligomer distribution when compared to the oligomer distribution in the absence of the metal halide, alkyl metal halide, and/or the alkyl metal compound. In an embodiment, the minimum metal to aluminum molar ratio can be $1\times10^{-1}$:1, $2.5\times10^{-1}$:1, $5\times10^{-1}$:1, $7.5\times10^{-2}$:1, or 1:1. In an embodiment, the maximum metal to aluminum molar ratio can be 3:1, 2.5:1, 2:1, 1.5:1, 1.25:1, 1.1:1 or 1:1. In an embodiment, the alkyl metal compound to aluminum halide molar ratio can range from any minimum metal to aluminum molar ratio described herein to any maximum metal to aluminum molar ratio described herein. Suitable ranges for the metal to aluminum molar ratio can include, but are not limited to, from $1\times10^{-1}$:1 to 3:1, from $2.5\times10^{-1}$:1 to 2.5:1, from $5\times10^{-1}$:1 to 2:1, from $5\times10^{-1}$:1 to 1.5:1, or from $5\times10^{1}$:1 to 1.25:1. Other suitable metal to aluminum molar ratio ranges are readily apparent from the present disclosure. Additional description of the catalyst systems comprising, consist essentially of, or consisting of, an alkylaluminum halide, an aluminum trihalide, or any combination thereof can be found in U.S. application Ser. No. 14/132,208.

In an embodiment, the catalyst system can comprise an acidic ionic liquid. In some embodiments, the catalyst system can comprise, consist essentially of, or consist of, (a) an acidic ionic liquid, or (b) an acidic ionic liquid and a halogenated hydrocarbon; alternatively, an acidic ionic liquid; or alternatively, an acidic ionic liquid and a halogenated hydrocarbon. Acidic ionic liquids and halogenated hydrocarbons are independently described herein and these independent descriptions can be utilized without limitation to further describe any appropriate catalyst system comprising an acid ionic liquid described herein.

Ionic liquids are a category of compounds which are made up entirely of ions and are generally liquids at or below process temperatures. Often, salts which are composed entirely of ions are solids with high melting points, for example, above 450° C. These solids are commonly known as 'molten salts' when heated to above their melting points. Sodium chloride, for example, is a common 'molten salt', with a melting point of 800° C. Ionic liquids differ from 'molten salts,' in that they have low melting points, for example, from −100° C. to 200° C. Ionic liquids tend to be liquids over a very wide temperature range, with some having a liquid range of up to 300° C. or higher. Ionic liquids are generally non-volatile, with effectively no vapor pressure. Many ionic liquids are air stable and water stable, and can be good solvents for a wide variety of inorganic, organic, and polymeric materials.

The properties of ionic liquids can be tailored by varying the cation and anion pairing. Ionic liquids and some of their commercial applications are described, for example, in J. Chem. Tech. Biotechnol, 1997, vol. 68(4), pp. 351-356; J. Phys. Condensed Matter, 5:(supp 34B):B99-B106 (1993); Chemical and Engineering News, Mar. 30, 1998, pp. 32-37; J. Mater. Chem., 1998, vol. 8, pp. 2627-2636; and Chem. Rev., 1999, vol. 99, pp. 2071-2084.

Ionic liquids can be characterized by the general formula $Q^+A^-$. Generally, $Q^+$ gives the ionic liquid a Lewis acidic character. Generally, the mole ratio of $A^-$ to $Q^+$ can range from 1:1 to 5:1; or alternatively, range from 1:1 to 2:1.

$Q^+$ of the ionic liquid can be a quaternary ammonium, quaternary phosphonium, or quaternary sulfonium; alternatively, quaternary ammonium; alternatively, quaternary phosphonium or alternatively, quaternary sulfonium. A⁻ of the ionic liquid can be a negatively charged ion. Negatively charged anions which can be present in ionic liquids include, but are not limited, halides, perhalides, nitrate, tetrahaloborates, hexahalophosphates, hexahaloantinomates, haloaluminates, halotantalates, halocuprates, haloferates, trifluoromethylsulfonium, or any combination thereof; alternatively, chloroaluminates, bromoaluminates, tetrachloroborate, tetrafluoroborate, hexafluorophosphate, trifluoromethane sulfonate, methylsulfonate, p-toluenesulfonate, or any combination thereof; alternatively, chloroaluminates, bromoaluminates, or any combination thereof; alternatively, haloaluminates, or alternatively, bromoalumnates. In some embodiments, the negatively charged ions which can be present in the ionic liquids can include, but are not limited to, Cl⁻, Br⁻, OCl₄⁻, NO₃⁻, BF₄⁻, BCl₄⁻, PF₆⁻, SbF₆⁻, AlCl₄⁻, Al₂Cl₇⁻, AlBr₄⁻, Al₂Br₇⁻, ArF₆⁻, TaF₆⁻, CuCl₂⁻, FeCl₃⁻, ZnCl₃⁻, SO₃CF₃⁻, SO₃Cl₇⁻, or any combination thereof; alternatively, AlCl₄⁻, Al₂Cl₇⁻, AlBr₄⁻, Al₂Br₇⁻, or any combination thereof; alternatively, AlCl₄⁻, Al₂Cl₇⁻, or any combination thereof; or AlBr₄⁻, Al₂Br₇⁻, or any combination thereof. A– which can be used in ionic liquids include, but are not limited to, chloroaluminates, bromoaluminates, tetrachloroborate, tetrafluoroborate, hexafluorophosphate, trifluoromethane sulfonate, methylsulfonate, p-toluenesulfonate. The ionic liquids which can be used advantageously in the present disclosure include acidic haloaluminates; alternatively, chloroaluminates, bromoaluminates, or any combination thereof; alternatively, chloroaluminates; or alternatively, bromoaluminates.

In some embodiments, Q⁺ for the ionic liquid can be amine-based. Among the most common ionic liquids are those formed by reacting a nitrogen-containing heterocyclic ring (cyclic amines), preferably nitrogen-containing aromatic rings (aromatic amines), with an alkylating agent (for example, an alkyl halide) to form a quaternary ammonium salt, followed by ion exchange or other suitable reactions to introduce the appropriate counter anionic species to form ionic liquids. Examples of suitable heteroaromatic rings include pyridine and its derivatives, imidazole and its derivatives, and pyrrole and its derivatives. These rings can be alkylated with varying alkylating agents to incorporate a broad range of alkyl groups on the nitrogen including straight, branched or cyclic $C_{1-20}$ alkyl group. Frequently, $C_{1-12}$ alkyl groups are used since alkyl groups larger than $C_{12}$ can produce undesirable solid products with some amines Pyridinium and imidazolium-based ionic liquids are perhaps the most commonly used ionic liquids. Other amine-based ionic liquids including cyclic and non-cyclic quaternary ammonium salts are frequently used. Phosphonium and sulphonium-based ionic liquids have also been used.

In embodiments, the haloaluminate ionic liquid can be a trialkylammonium haloaluminate ionic liquid, a tetraalkylammonium haloaluminate ionic liquid, hydrogen pyridinium haloaluminate ionic liquid, an N-alkylpryidinium haloaluminate ionic liquid, an N,N'-dialkylimidizolium haloaluminate ionic liquid, or any combination thereof; alternatively, a tetraalkylammonium haloaluminate ionic liquid, an N-alkylpryidinium haloaluminate ionic liquid, an N,N'-dialkylimidizolium haloaluminate ionic liquid, or any combination thereof; alternatively, a tetraalkylammonium haloaluminate ionic liquid; alternatively, an N-alkylpryidinium haloaluminate ionic liquid; or alternatively, an N,N'-dialkylimidizolium haloaluminate ionic liquid.

In embodiments, the haloaluminate ionic liquid can be a chloroaluminate ionic liquid, a bromoaluminate ionic liquid, or any combination thereof; alternatively, a chloroaluminate ionic liquid; or alternatively, a bromoaluminate ionic liquid.

In embodiments, the haloaluminate ionic liquid can be N-(n-butyl)pyridinium chloroaluminate, N-(n-butyl)pyridinium bromoaluminate, or any combination thereof; alternatively, N-(n-butyl)pyridinium bromoaluminate; or alternatively, N-(n-butyl)pyridinium chloroaluminate.

In embodiments, the haloaluminate ionic liquid can have a cationic portion comprising trialkylammonium, tetraalkylammonium, N-alkylpyridinium, or N',N"-dialkylimidizolium; alternatively, tetraalkylammonium, N-alkylpyridinium, or N',N"-dialkylimidizolium; alternatively, trialkyl ammonium; alternatively, tetraalkylammonium; alternatively, N-alkylpyridinium; or alternatively, N',N"-dialkylimidizolium. In embodiments where the cationic portion is trialkylammonium, the cationic portion can have Structure ILC 1. In embodiments where the cationic portion is tetraalkylammonium, the cationic portion can have Structure ILC 2. In embodiments where the cationic portion is N-alkylpyridinium, the cationic portion can have Structure ILC 3 or Structure ILC 4; alternatively, Structure ILC 3; or alternatively, Structure ILC 4. In embodiments where the cationic portion is N',N"-dialkylimidizolium, the cationic portion can have Structure ILC 5 or Structure ILC 6; alternatively, Structure ILC 5; or alternatively, Structure ILC 6.

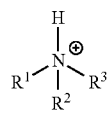

ILC 1

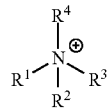

ILC 2

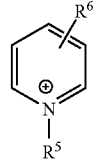

ILC 3

ILC 4

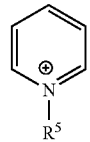

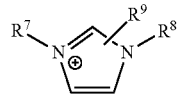

ILC 5

ILC 6

Each $R^1$, $R^2$, and $R^3$ of the trialkylammonium having Structure ILC 1, each $R^1$, $R^2$, $R^3$, and $R^4$ of the tetraalkylammonium having Structure ILC 2, each $R^5$ and $R^6$ of the N-alkylpyridinium having Structure ILC 3, each $R^5$ of the N-alkylpyridinium having Structure ILC 4, each $R^7$, $R^8$, and $R^9$ of the N',N"-dialkylimidizolium having Structure ILC 5, or each $R^7$ and $R^8$ of the N',N"-dialkylimidizolium having Structure ILC 6 independently can be a hydrocarbyl group; or alternatively, an alkyl group. General and specific hydrocarbyl groups and alkyl groups are independently described herein as potential substituent groups for various aspects and embodiments described herein and these independently described general and specific hydrocarbyl and alkyl group can be utilized without limitation to further describe each $R^1$, $R^2$, and $R^3$ of the trialkylammonium having Structure ILC 1, each $R^1$, $R^2$, $R^3$, and $R^4$ of the tetraalkylammonium having Structure ILC 2, each $R^5$ and $R^6$ of the N-alkylpyridinium having Structure ILC 3, each $R^5$ of the N-alkylpyridinium having Structure ILC 4, each $R^7$, $R^8$, and $R^9$ of the N',N"-dialkylimidizolium having Structure ILC 5, or each $R^7$ and $R^8$ of the N',N"-dialkylimidizolium having Structure ILC 6.

General and specific halogenated hydrocarbons are independently disclosed herein as promoters for Lewis acid catalyst systems. These general and specific halogenated hydrocarbons can be utilized without limitation, and in any combination, with the general and specific ionic liquids disclosed herein to further described catalyst systems comprising, consisting essentially of, or consisting of, (a) an ionic liquid and (b) a halogenated hydrocarbon that can be utilized as the catalyst system comprising an ionic liquid. In embodiments utilizing a haloaluminate ionic liquid, a molar ratio of halide in the halogenated hydrocarbon to aluminum in the haloaluminate ionic liquid can be at least 0.0001:1, 0.001:1, 0.005:1, 0.01:1, 0.025:1, 0.05:1, 0.075:1, 0.1:1, 0.14:1, 0.18:1, or 0.2:1; alternatively or additionally, a maximum molar ratio of halide in the halogenated hydrocarbon to aluminum in the haloaluminate ionic liquid can be less than 10:1, 7.5, 5:1, 4:1, 3:1, 2:1 1.75:1, or 1.5:1. In an embodiment, the molar ratio of halide in the halogenated hydrocarbon to aluminum in the haloaluminate ionic liquid can range from any minimum molar ratio of halide in the halogenated hydrocarbon to aluminum in the haloaluminate ionic liquid to any maximum molar ratio of halide in the halogenated hydrocarbon to aluminum in the haloaluminate ionic liquid described herein. In some embodiments, suitable ranges for the molar ratio of halide in the halogenated hydrocarbon to aluminum in the haloaluminate ionic liquid can include, but are not limited to, a molar ratio of halide in the halogenated hydrocarbon to aluminum in the haloaluminate ionic liquid from 0.0001:1 to 10:1, from 0.001:1 to 7.5:1, from 0.01:1 to 5:1, from 0.025:1 to 5:1, from 0.05:1 to 5:1, from 0.05:1 to 5:1, from 0.1:1 to 5:1, from 0.1:1 to 4:1, from 0.1:1 to 3:1, from 0.12:1 to 4:1, from 0.14:1 to 5:1, from 0.14:1 to 4:1, from 0.14:1 to 3:1, from 0.14:1 to 2:1, from 0.16:1 to 4:1, from 0.16:1 to 3:1, from 0.16:1 to 2:1, from 0.18:1 to 4:1, from 0.18:1 to 3:1, from 0.18:1 to 2:1, from 0.2:1 to 4:1, from 0.2:1 to 3:1, or from 0.2:1 to 2:1. Other suitable molar ratios of halide in the halogenated hydrocarbon to aluminum in the haloaluminate ionic liquid which can be utilized are readily apparent from the present disclosure. The molar ratio of halide in the halogenated hydrocarbon to aluminum in the haloaluminate ionic liquid can be referred to as the halide in the halogenated hydrocarbon to aluminum in the haloaluminate ionic liquid molar ratio.

Additional descriptions of the catalyst systems comprising an acidic ionic liquid suitable for use as a catalyst system in the current disclosure can be found in U.S. application Ser. No. 14/829,987 and U.S. Pat. No. 6,395,948.

In an embodiment, the catalyst system can comprise a metallocene. In some embodiments, the catalyst system can comprise (a) a metallocene and an aluminoxane, (b) a metallocene, a non-coordinating anion, and an organoaluminum compound (e.g., alkylaluminum compound), or (c) a metallocene, a chemically-treated solid oxide, and an organoaluminum compound (e.g., an alkylaluminum compound); alternatively, a metallocene and an aluminoxane; alternatively, a metallocene, a non-coordinating anion, and organoaluminum compound; or alternatively, a metallocene, a chemically-treated solid oxide, and an organoaluminum compound. The metallocene, aluminoxane, non-coordinating anion, organoaluminum compound, and chemically treated solid oxide used in conjunction with various catalyst systems comprising a metallocene described herein are independently described herein. These metallocenes, aluminoxanes, non-coordinating anions, organoaluminum compounds, and chemically treated solid oxides can be used without limitation to further describe the various aspects and embodiments of the catalyst systems comprising a metallocene.

Generally, the metallocene can be a metal compound pi-bonded to at least one $\eta^{x \geq 5}$ ligand. In other embodiments, the metallocene can be a metal compound pi-bonded to two $\eta^{x \geq 5}$ ligands (e.g., an unbridged metallocene); or alternatively, a metal compound having two pi-bonds to a ligand having two $\eta^{x \geq 5}$ groups (e.g., a bridged metallocene).

The metal of the metallocene can comprise a Group 3-10 transition metal (one or more than one Group 3-10 transition metal). In an embodiment, the metal of the metallocene can comprise a Group 3, 4, 5, or 6 transition metal, or a combination of two or more Group 3, 4, 5, or 6 transition metals. In some embodiments, the metal of the metallocene can comprise chromium, titanium, zirconium, hafnium, vanadium, or any combination thereof; or alternatively, chromium, titanium, zirconium, hafnium, or any combination thereof; or alternatively, zirconium. Moreover, the catalyst system can comprise two or more metallocenes, wherein each metal of the metallocene compound independently can comprise chromium, titanium, zirconium, hafnium, vanadium, or any combination thereof. In some embodiments, the catalyst system can comprise two or more metallocenes wherein each metal comprise zirconium.

When the metallocene has one or two pi-bonded $\eta^{x \geq 5}$ ligands, each pi-bonded $\eta^{x \geq 5}$ ligand independently can be cyclopentadienyl (substituted or unsubstituted) or a ring system (substituted or unsubstituted) containing a cyclopentadienyl group (substituted or unsubstituted). In an embodiment, each pi-bonded $\eta^{x \geq 5}$ ligand, which can be utilized for a metallocene having one or two pi-bonded $\eta^{x \geq 5}$ ligands, independently can be a cyclopentadienyl group (substituted or unsubstituted), an indenyl group (substituted or unsubstituted) or a fluorenyl group (substituted or unsubstituted). When the metallocene has one or two pi-bonded $\eta^{x \geq 5}$ ligands, each pi-bonded $\eta^{x \geq 5}$ ligand independently can be cyclopentadienyl, a substituted cyclopentadienyl, indenyl, a substituted indenyl, fluorenyl, or a substituted fluorenyl; alternatively, cyclopentadienyl or a substituted cyclopentadienyl; alternatively, indenyl or a substituted indenyl; or alternatively, fluorenyl or a substituted fluorenyl. Groups which can be utilized as substituents are independently described herein and these groups/substituents can be utilized without limitation and in any combination to further describe the substituted cyclopentadienyl, substituted indenyl, and/or substituted fluorenyl which can be utilized as an $\eta^{x \geq 5}$ ligand for any metallocene described herein.

When the metallocene has an $\eta^{x \geq 5}$ ligand having two $\eta^{x \geq 5}$ groups, each pi-bonded $\eta^{x \geq 5}$ group independently can be any group containing a cyclopentadienyl group (substituted or unsubstituted) or a ring system (substituted or unsubstituted) containing a cyclopentadienyl group (substituted or unsubstituted). In an embodiment, when the metallocene has an $\eta^{x\geq5}$ ligand having two $\eta^{x\geq5}$ groups, each $\eta^{x\geq5}$ group independently can be a cyclopentadienyl group (substituted or unsubstituted), an indenyl group (substituted or unsubstituted), or a fluorenyl group (substituted or unsubstituted). When the metallocene has a $\eta^{x\geq5}$ and having two $\eta^{x\geq5}$ groups, each pi-bonded $\eta^{x\geq5}$ group independently can be a cyclopentadienyl group, a substituted cyclopentadienyl group, an indenyl group, a substituted indenyl group, a fluorenyl group, or a substituted fluorenyl group; alternatively, a cyclopentadienyl group or a substituted cyclopentadienyl group; alternatively, an indenyl group or a substituted indenyl group; or alternatively, a fluorenyl group or a substituted fluorenyl group. Groups which can be utilized as substituents are independently described herein and these groups/substituents can be utilized without limitation and in any combination to further describe the substituted cyclopentadienyl group, substituted indenyl group, and/or a substituted fluorenyl group which can be present in a metallocene having an $\eta^{x\geq5}$ ligand with two $\eta^{x\geq5}$ groups.

When the metallocene has an $\eta^{x\geq5}$ ligand having two $\eta^{x\geq5}$ groups (a bridged metallocene), the two independent $\eta^{x\geq5}$ groups (which are independently described herein) can be linked by a linking group. In an embodiment, the two $\eta^{x\geq5}$ groups can be linked with a linking group separating the two $\eta^{x\geq5}$ groups by from 1 to 10 atoms; alternatively, 1 to 5 atoms; alternatively, 1 atom; alternatively, 2 atoms; alternatively, 4 atoms; or alternatively, 5 atoms. Generally, the number of atoms separating the two $\eta^{x\geq5}$ groups is the number of atoms of the shortest chain separating the two $\eta^{x\geq5}$ groups and not the total number of atoms in the linking group. In an embodiment, each atom separating the $\eta^{x\geq5}$ groups can be selected from the group consisting of carbon, silicon, and germanium; alternatively, the group consisting of carbon and silicon; alternatively, carbon; or alternatively, silicon. Non-limiting examples of linking groups which can be utilized to link the two independent $\eta^{x\geq5}$ groups of a metallocene having an $\eta^{x\geq5}$ ligand having two $\eta^{x\geq5}$ groups include $(CH_3)_2C<$, $(CH_2CH_2CH_2)_2C<$, $(CH_2CH_2CH_2CH_2)_2C<$, $(CH_3)_2Si<$, $(CH_2CH_2CH_2)_2Si<$, $(CH_2CH_2CH_2CH_2)_2Si<$, $-CH_2CH_2-$, $-CH(CH_3)CH(CH_3)-$, or $-CH_2CH_2CH=CHCH_2-$, alternatively, $(CH_3)_2C<$ or $(CH_3)_2Si<$; alternatively, $(CH_3)_2C<$; or alternatively, $(CH_3)_2Si<$.

In certain embodiments, the metallocene can comprise a bridged zirconium metallocene. In an embodiment, the metallocene can comprise a bridged zirconium metallocene with a carbon bridging atom or a silicon bridging atom. In some embodiments, the metallocene can comprise a bridged zirconium based metallocene having an $\eta^{x\geq5}$ ligand having two $\eta^{x\geq5}$ groups independently selected from the group of a cyclopentadienyl group (substituted or unsubstituted), an indenyl group (substituted or unsubstituted), or a fluorenyl group (substituted or unsubstituted) linked by a carbon bridging atom or a silicon bridging atom. In other embodiments, the metallocene can comprise a bridged zirconium based metallocene having an $\eta^{x\geq5}$ ligand having two cyclopentadienyl groups (each independently substituted or unsubstituted) linked by a carbon bridging atom or a silicon bridging atom. In these and other embodiments, the bridging atom can contain two alkyl substituents (e.g., each substituent can independently be methyl, ethyl, n-propyl, or n-butyl, among other substituents described herein) on the bridging atom. Additionally or alternatively, the bridged metallocene compound can contain one or more alkyl substituents on one or two of the two $\eta^{x\geq5}$ groups.

In certain other embodiments, the metallocene can comprise an unbridged metallocene compound. In an embodiment, the metallocene can comprise a zirconium metallocene having two $\eta^{x\geq5}$ ligands independently selected from the group consisting of a cyclopentadienyl ligand (substituted or unsubstituted), an indenyl ligand (substituted or unsubstituted), and a fluorenyl ligand (substituted or unsubstituted) compound. In some embodiments, the metallocene can comprise a zirconium having two cyclopentadienyl ligand (substituted or unsubstituted), two indenyl ligands (substituted or unsubstituted), two fluorenyl ligands (substituted or unsubstituted), or a cyclopentadienyl ligand (substituted or unsubstituted) and an indenyl ligand (substituted or unsubstituted); alternatively, two cyclopentadienyl ligands (substituted or unsubstituted); alternatively, two indenyl ligands (substituted or unsubstituted); or alternatively, a cyclopentadienyl ligand (substituted or unsubstituted) and an indenyl ligand (substituted or unsubstituted). Additionally or alternatively, the unbridged metallocene compound can contain one or more alkyl substituents on one or two of the two $\eta^{x\geq5}$ ligands.

Illustrative and non-limiting examples of metallocenes that are suitable for use in any catalyst system described herein which uses a metallocene can include the following metallocenes:

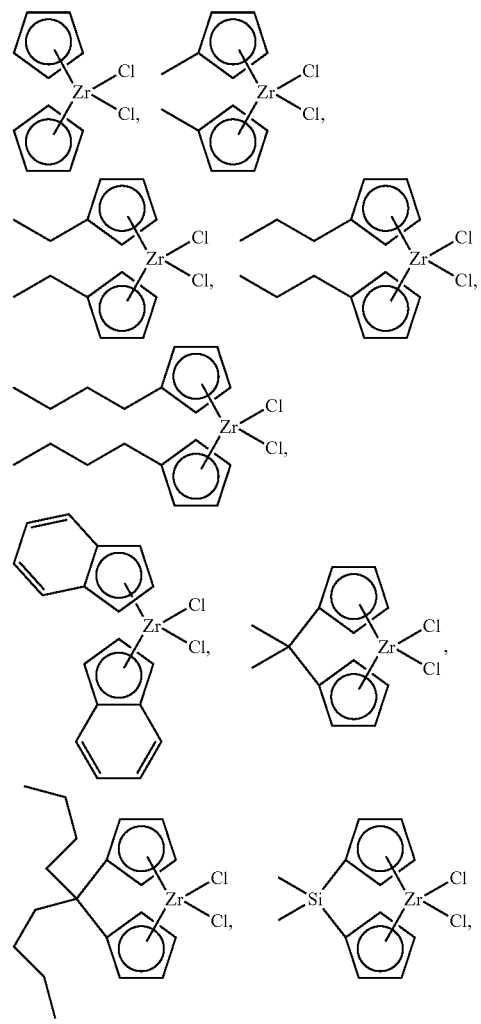

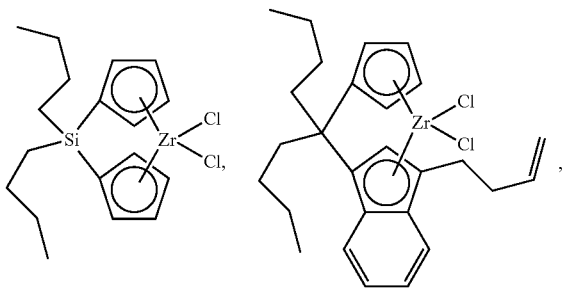
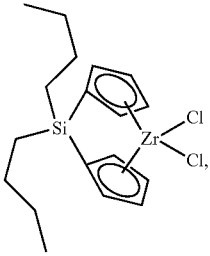
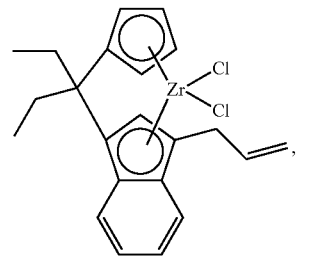
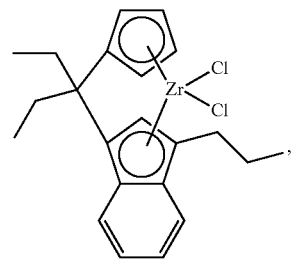
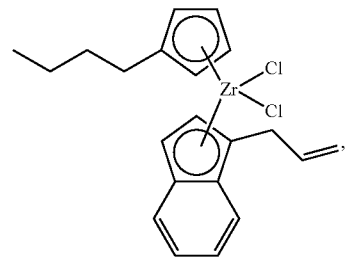

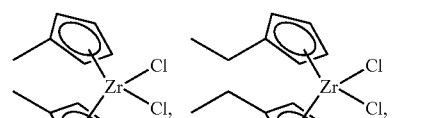
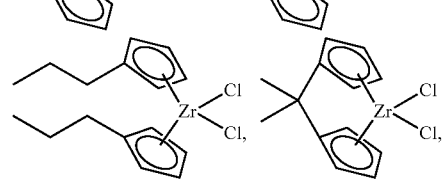
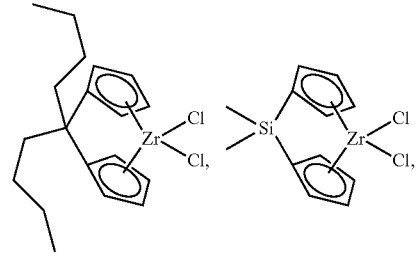

or any combination thereof; alternatively, or any combination thereof. Other suitable metallocenes (compounds are disclosed in U.S. Pat. Nos. 7,026,494, 7,041,617, 7,199,073, 7,226,886, 7,312,283, 7,517,939, 7,619,047, 7,919,639, and 8,080,681.

In a non-limiting embodiment, the aluminoxane can have a repeating unit characterized by the Formula I:

Formula I wherein R' is a linear or branched alkyl group. In an embodiment, each alkyl group, R', of the aluminoxane independently can be a $C_1$ to $C_{20}$ alkyl group; alternatively, a $C_1$ to $C_{10}$ alkyl group; or alternatively, a $C_1$ to $C_6$ alkyl group. In an embodiment, each alkyl group, R', of the aluminoxane independently can be a methyl group, an ethyl group, a propyl group, a butyl group, a pentyl group, a hexyl group, a heptyl group, or an octyl group; alternatively, a methyl group, an ethyl group, a butyl group, a hexyl group, or an octyl group. In some embodiments, each alkyl group independently can be a methyl group, an ethyl group, an n-propyl group, a n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group. Generally, n of Formula I is greater than 1; or alternatively greater than 2. In an embodiment, n can range from 2 to 15; or alternatively, range from 3 to 10. In some non-limiting embodiments, the aluminoxane can comprise methylaluminoxane (MAO), ethylaluminoxane, modified methylaluminoxane (MMAO), n-propylaluminoxane, iso-propylaluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, iso-pentylaluminoxane, neopentylaluminoxane, or mixtures thereof. In some non-limiting embodiments, useful aluminoxanes can include methylaluminoxane (MAO), modified methylaluminoxane (MMAO), isobutyl aluminoxane, t-butyl aluminoxane, or mixtures thereof. In other non-limiting embodiments, the aluminoxane can comprise methylaluminoxane (MAO); alternatively, ethylaluminoxane; alternatively, modified methylaluminoxane (MMAO); alternatively, n-propylaluminoxane; alternatively, iso-propylaluminoxane; alternatively, n-butylaluminoxane; alternatively, sec-butylaluminoxane; alternatively, iso-butylaluminoxane; alternatively, t-butyl aluminoxane; alternatively, 1-pentylaluminoxane; alternatively, 2-pentylaluminoxane;

alternatively, 3-pentylaluminoxane; alternatively, iso-pentylaluminoxane; or alternatively, neopentylaluminoxane.

The term "non-coordinating anion" (NCA) refers to an anion which either does not coordinate to a cation (e.g., metal cation) or which is only weakly coordinated to the cation thereby remaining sufficiently labile to be displaced by a neutral Lewis base. "Compatible" non-coordinating anions are those which are not degraded to neutral species when the initially formed complex decomposes. Non-coordinating anions useful in metallocenes catalyst systems including a non-coordinating anion are those that are compatible, stabilize the metal cation in the sense of balancing its ionic charge, and yet retain sufficient ability to permit displacement by an ethylenically unsaturated monomer during oligomerization. Metallocenes catalyst systems including a non-coordinating anion can sometimes use a trialkylaluminum compound (e.g., tri-isobutyl aluminum or tri-octyl aluminum, among others disclosed herein) as a scavenger.

Generally, the non-coordinating anion can be a part of any compound, ionic or neutral, which contains all anion which can activate the oligomerization, Compounds containing non-coordinating anion can contain an active proton, or some other cation associated with, but not coordinated to, or only loosely coordinated to, the non-coordinating anion. Such compounds are described in EP 570 982 A, EP 520 732 A, EP 495 375 A, EP 500 944 B1, EP277 003A, EP 277 004 A, U.S. Pat. Nos. 5,153,157, 5,198,401, 5,066,741, 5,206, 197, 5,241,025, 5,384,299, 5,502,124, and U.S. patent application Ser. No. 08/285,380, filed Aug. 3, 1994.

Compounds which include a non-coordinating anion can be represented by the following formula:

$$(W^{f+})_g(NCA^{h-})_i$$

wherein $W^{f+}$ is a cation component having the charge f+, $NCA^{h-}$ is a non-coordinating anion having the charge h-, f is an integer from 1 to 3, h is an integer from 1 to 3, and g and h are constrained by the relationship: $(g)\times(f)=(h)\times(i)$. The cation component, ($W^{f+}$) can include Brønsted acids such as protons or protonated Lewis bases or reducible Lewis acids capable of protonating or abstracting a moiety, such as an alkyl or aryl, from an analogous metallocene or a Group 15 containing transition metal catalyst compound, resulting in a cationic transition metal species. In an embodiment, compounds which include a non-coordinating anion can be represented by the following formula:

$$(LB-H^{f+})_g(NCA^{h-})_i$$

wherein LB is a neutral Lewis base; H is hydrogen; $NCA^{h-}$ is a non-coordinating anion having the charge h-, f is an integer from 1 to 3, h is an integer from 1 to 3, and g and h are constrained by the relationship:

$$(g)\times(f)=(h)\times(i).$$

In some embodiments, the activating cation ($W^{f+}$) can be a Brønsted acid, ($LB-H^{f+}$), capable of donating a proton to the transition metal catalyst compound resulting in a transition metal cation. In such embodiments, the non-coordinating anion can be represented by the following formula:

$$(LB-H^{f+})_g(NCA^{h-})_i$$

wherein LB is a neutral s base; H is hydrogen; $NCA^{h-}$ is a non-coordinating anion having the charge h-, f is an integer from 1 to 3, h is an integer from 1 to 3, and g and h are constrained by the relationship: $(g)\times(f)=(h)\times(i)$. In an embodiment, ($LB-H^{f+}$) can comprise ammonium cations, oxonium cations, phosphonium cations, silylium cations, or any combination thereof. In an embodiment, the ammonium cations can be those of methylamine, dimethylamine, diethylamine, N-methylaniline, diphenylamine, trimethylamine, triethylamine, N,N-dimethylaniline, methyldiphenylamine, pyridine, p-bromo N,N-di p-nitro-N,N-dimethylaniline, phosphoniums from triethylphosphine, triphenylphosphine, diphenylphosphine, or any combination thereof. In an embodiment, the oxonium cations can be those of ethers such as dimethyl ether diethyl ether, tetrahydrofuran, dioxane, or any combination thereof. In an embodiment, the sulfonium cations can be those of thioethers, such as diethyl thioethers and tetrahydrothiophene, or any combination thereof.

The activating cation ($W^{f+}$) can also be an abstracting moiety such as silver, carbonium cations, tropylium, carbenium cations, ferrocenium cations, or any combination thereof; alternatively, carbonium cations, ferrocenium cations, or any combination thereof. Most preferably ($W^{f+}$) is triphenyl carbonium.

The non-coordinating anion, ($NCA^{h-}$), can include those having the formula $[T^{j+}Q_k]^{h-}$ wherein j is an integer from 1 to 3, k is an integer from 2 to 6; k-j=h, T is an element selected from Group 13 or 15 of the Periodic Table of the Elements, and Q can be a hydride, a $C_3$ to $C_{20}$ bridged or unbridged dialkylamido, a halide, a $C_1$ to $C_{20}$ alkoxide group, a $C_6$ to $C_{20}$ aryloxide group, a $C_1$ to $C_{20}$ hydrocarbyl group, or a $C_1$ to $C_{20}$ substituted hydrocarbyl group with the proviso that in not snore than one occurrence Q can be a halide. In some embodiments, the $C_1$ to $C_{20}$ substituted hydrocarbyl can be a $C_1$ to $C_{20}$ halogenated hydrocarbyl group. In an embodiment, each Q can be a $C_1$ to $C_{20}$ fluorinated hydrocarbyl group; alternatively, $C_6$ to $C_{20}$ a fluorinated aryl group; alternatively, a pentafluoro aryl group. In an embodiment, T can be boron or aluminum; alternatively boron; or alternatively, aluminum. Examples of suitable ($NCA^{h-}$)$_j$ also include diboron compounds as disclosed in U.S. Pat. No. 5,447,895.

Illustrative, but non-limiting examples of boron compounds which can be used as the non-coordinating anion, or the compound including a non-coordinating anion can include tri-substituted ammonium borate salts, dialkyl ammonium borate salts, and/or tri-substituted phosphonium salts; alternatively, tri-substituted ammonium borate salts; alternatively, dialkyl ammonium borate salts; or alternatively, tri-substituted phosphonium salts. Tri-substituted ammonium borate salts which can be utilized include trimethylammonium tetraphenylborate, triethylammonium tetraphenylborate, tripropylammonium tetraphenylborate, tri(n-butyl)ammonium tetraphenyl borate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluoro-phenyl)borate, triethylammonium tetrakis(pentafluorophenyl)borate, tripropylammonium tetrakis(penta-fluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis-(pentafluorophenyl)borate, trimethylammonium tetrakis(2,3,4,6-tetrafluorophenyl)borate, triethylammonium tetrakis(2,3,4, 6-tetrafluorophenyl)borate, tripropylammonium tetrakis(2, 3,4,6-tetra-fluorophenyl)borate, tri(n-butyl)ammonium tetrakis(2,3,4,6-tetrafluorophenyl)borate, dimethyl(t-butyl) ammonium tetrakis(2,3,4,6-tetrafluorophenyl)borate, N,N-dimethylanilinium tetrakis(2,3,4,6-tetra-fluorophenyl)borate, N,N-diethylanilinium tetrakis(2,3,4,6-tetrafluorophenyl)borate, and N,N-dimethyl(2,4,6-trimethylanilinium) tetrakis(2,3,4,6-tetrafluorophenyl) borate. Dialkyl ammonium borate salts which can be utilized include di-(iso-propyl)ammonium tetrakis(pentafluorophenyl)borate, and dicyclohexylammonium tetrakis(pentafluorophenyl)borate. Tri-substituted phosphonium borate salts which can be utilized include triphenylphosphonium tetrakis (pentafluorophenyl)borate, tri(o-tolyl)phosphonium tetrakis (pentafluorophenyl)borate, and tri(2,6-dimethylphenyl) phosphonium tetrakis-(pentafluorophenyl)borate.

In a particular embodiment, the compound including a non-coordinating anion can be N,N-dimethylanilinium tetrakis(perfluorophenyl)borate and/or triphenylcarbenium tetrakis-(perfluorophenyl)borate; or alternatively, N,N-dimethylanilinium tetrakis(perfluorophenyl)borate.

In another embodiment, the non-coordinating anion can be a part of a compound, ionic or neutral, not containing an active proton, but capable of producing an analogous metallocene catalyst cation and the non-coordinating anion. These compounds are described in EP 426637 A, EP 573403 A, and U.S. Pat. No. 5,387,568.

In an embodiment, the non-coordinating anion can be formed in-situ using an initially neutral compound (e.g., neutral Lewis acid) that can form a cationic metal complex and the non-coordinating anion in the reaction zone. Exemplary neutral acid Lewis acids which can be used include those having the formula $A^{10}(R^{11})_3$, where $A^{10}$ can be a Group 13 element and $R^{11}$ can be a hydrogen, a $C_1$ $C_{20}$ hydrocarbyl group, or a $C_1$ $C_{20}$ substituted hydrocarbyl. In an embodiment, $A^{10}$ can be boron or aluminum; alternatively, boron, or alternatively, aluminum. In some embodiments, $R^{11}$ can be an alkyl group, an arene, or a perfluorinated arene; alternatively, a $C_1$ $C_{20}$ alkyl group, a phenyl group, or a perfluorinated phenyl group; alternatively, a $C_1$ $C_{20}$ alkyl group; alternatively, a phenyl group; or alternatively, a perfluorinated phenyl group. Non-limiting examples of these neutral Lewis acids can include $BMe_3$, $BEt_3$, $B(iBu)_3$, $BPh_3$, $B(C_6F_5)_3$, $B(C_{10}F_7)_3$, $AlMe_3$, $Al(iBu)_3$, $AlPh_3$, $Al(C_6F_5)_3$, $[NMeHPh][B(C_{10}F_7)_4]$, alumoxanes, or any combination thereof; alternatively, $BMe_3$, $BEt_3$, $B(iBu)_3$, $BPh_3$, $B(C_6F_5)_3$, $B(C_{10}F_7)_3$, or any combination thereof; alternatively, $AlMe_3$, $AlEt_3$, $Al(iBu)_3$, $Al(C_6F_5)_3$, or any combination thereof; alternatively, $BPh_3$, $B(C_6F_5)_3$, or any combination thereof; or alternatively, aluminoxanes. Other neutral Lewis acids, combinations of forming the non-coordinating anion, and methods of forming the non-coordinating anion are disclosed in U.S. Pat. Nos. 5,624,878, 5,486,632, 5,527,929, EP 0427697A, EP 520732A, EP 495375A, and E. Y. -X. Chen and T. J. Marks, "Cocatalysts for Metal-Catalyzed Olefin Polymerization: Activators, Activation Processes, and Structure-Activity Relationships", Chem. Rev., 100, 13914434 (2000).

When the compound does not contain at least one hydride or hydrocarbyl ligand, but does contain at least one functional group ligand (e.g., chloride, amido or alkoxy ligands), and the functional group ligands are not capable of discrete ionizing abstraction with the ionizing anion pre-cursor compounds, the functional group ligands can be converted via known alkylation reactions with organometallic compounds such as lithium or aluminum hydrides or alkyls, alkyialuminoxanes, and/or Grignard reagents. EP 500944 A, EP 570982A, and EP 612768A describe the reaction of alkyl-aluminum compounds with analogous dihalide substituted metallocene compounds prior to or with the addition activating non-coordinating anion precursor compounds.

Additional non-coordinating anions are known in the art and will be suitable for use with the catalysts of the disclosure, for example as described in U.S. Pat. No. 5,278, 119 and the review articles by S. H. Strauss, "The Search for Larger and More Weakly Coordinating Anions", Chem. Rev., 93, 927-942 (1993) and C. A. Reed, "Carboranes: A New Class of Weakly Coordinating Anions for Strong Electrophiles, Oxidants and Superacids", Ace. Chem. Res., 31, 133-139 (1998).

When the cations of non-coordinating anion precursors are Brønsted acids (e.g., protons or protonated Lewis bases (excluding water)) or reducible Lewis acids (e.g., ferrocenium or silver cations, or alkali or alkaline earth metal cations such as those of sodium, magnesium or lithium), the cation to organoaluminum compound molar ratio may be any ratio. Combinations of the described organoaluminum compounds can also be used. In an embodiment, the organoaluminum compound that can be utilized with these cations can include trialkylaluminums, aluminoxanes, or any combination thereof; alternatively, trialkylaluminums; or alternatively, aluminoxanes. Trialkylaluminums and aluminoxanes are described herein and can be utilized without limitation with the non-coordinating canons described herein. In some non-limiting embodiments, the combinations of cations and organoaluminum compounds can include mixtures of (1) methylaluminoxane with dimethylanilinium tetrakis(pentafluorophenyl)borate or tris(pentafluorophenyl)boron, (2) a trialkylaluminum compound (e.g., any one or more of tri-isobutyl aluminum, triethyl aluminum, tri-n-alkylaluminum or trimethyl aluminum) with dimethylanilinium tetrakis(pentafluorophenyl)borate or tris (pentafluorophenyl)boron or their analogs. In another particular embodiment, a mixture of tris(perfluorophenyl) boron and methylalumoxane (or modified methylaluminoxane) can be used.

In an aspect, the catalyst systems comprising a metallocene can also include a chemically-treated solid oxide. The term "chemically-treated solid oxide" is used interchangeably with similar terms such as, "solid oxide treated with an electron-withdrawing anion," "treated solid oxide," or "solid super acid," which can also be termed "SSA." While not intending to be bound by theory, it is thought that the chemically-treated solid oxide can serve as an acidic activator-support. In one embodiment, the chemically-treated solid oxide can comprise a solid oxide treated with an electron-withdrawing anion. Alternatively, in another embodiment, the chemically-treated solid oxide can comprise a solid oxide treated with an electron-withdrawing anion, the solid oxide containing a Lewis-acidic metal ion. Non-limiting examples of suitable chemically-treated solid oxides are disclosed in, for instance, U.S. Pat. Nos. 7,294, 599, 7,601,665, 7,884,163, 8,309,485, 8,623,973, 8,703,886, and 9,023,959.

In one aspect and any embodiment of this disclosure, the chemically-treated solid oxide can comprise at least one solid oxide treated with at least one electron-withdrawing anion. Generally, the solid oxide can comprise any solid oxide that can be characterized as having a high surface area, and the electron-withdrawing anion can comprise any anion that increases the acidity of the solid oxide as compared to the solid oxide that is not treated with at least one electron-withdrawing anion. Generally, the electron-withdrawing component used to treat the oxide can be any component that increases the Lewis or Brønsted acidity of the solid oxide upon treatment. In one aspect, the electron-withdrawing component can be an electron-withdrawing anion derived from a salt, an acid, or other compound (e.g., a volatile organic compound) that can serve as a source or precursor for that anion.

In an embodiment, the chemically-treated solid oxide can comprise fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, or phosphated silica-coated alumina, or any combination thereof. In another embodiment, the chemically-treated solid oxide employed in the catalyst systems described herein can be, or can comprise, a fluorided solid oxide and/or a sulfated solid oxide, non-limiting examples of which can include fluorided alumina, sulfated alumina, fluorided silica-alumina, sulfated silica-alumina, fluorided silica-zirconia, fluorided silica-coated alumina, fluorided-chlorided silica-coated alumina, or sulfated silica-coated alumina, or any combination thereof. In yet another embodiment, the chemically-treated solid oxide can comprise fluorided alumina; alternatively, chlorided alumina; alternatively, sulfated alumina; alternatively, fluorided silica-alumina; alternatively, sulfated silica-alumina; alternatively, fluorided silica-zirconia; alternatively, chlorided silica-zirconia; alternatively, sulfated silica-coated alumina; alternatively, fluorided-chlorided silica-coated alumina; or alternatively, fluorided silica-coated alumina. In some embodiments, the chemically-treated solid oxide can comprise a fluorided solid oxide, while in other embodiments, the chemically-treated solid oxide can comprise a sulfated solid oxide.

In another aspect and in any embodiment of this disclosure, the solid oxide can comprise silica, alumina, silica-alumina, silica-coated alumina, aluminum phosphate, heteropolytungstate, titania, silica titania, zirconia, silica-zirconia magnesia, boria, zinc oxide, mixed oxides thereof, or mixtures thereof. In another embodiment, the solid oxide can comprise silica, alumina, silica-alumina, silica-coated alumina, titania, zirconia, magnesia, boria, zinc oxide, any mixed oxide thereof, or any combination thereof. In yet another embodiment, the solid oxide can comprise alumina, silica-alumina, silica-coated alumina, silica-titania, silica-zirconia, alumina-boria, or any combination thereof. In still another embodiment, the solid oxide can comprise silica, alumina, silica-alumina, silica-coated alumina, or any mixture thereof; alternatively, silica; alternatively, alumina; alternatively, silica-alumina; or alternatively, silica-coated alumina.

In an embodiment, the solid oxide can include mixed oxides. Mixed oxides which can be utilized as the solid oxide can include silica-alumina, silica-titania, silica-zirconia, zeolites, clay minerals, alumina-titania, alumina-zirconia, and zinc-aluminate; alternatively, silica-alumina, silica-titania, silica-zirconia, alumina-titania, alumina-zirconia, and zinc-aluminate; alternatively, silica-alumina, silica-titania, silica-zirconia, and alumina-titania. In some embodiments, the mixed oxides that can be used in the activator-support of the present disclosure can comprise, consist essentially of, or consist of, silica-alumina; alternatively, silica-titania; alternatively, silica-zirconia; alternatively, zeolites; alternatively, clay minerals; alternatively, alumina-titania; alternatively, alumina-zirconia; alternatively, and zinc-aluminate. In some embodiments, aluminosilicates such as clay minerals, calcium aluminosilicate, or sodium aluminosilicate are useful oxides that can be used in the activator-support of the present disclosure. In some embodiments, the solid oxide used herein also can encompass oxide materials such as silica-coated alumina, as described in U.S. Pat. No. 7,884,163.

The silica-alumina or silica-coated alumina solid oxide materials which can be used as the solid oxide can have a silica content from 5% to 95% by weight. In one embodiment, the silica content of these solid oxides can be from 10% to 80%, or from 20% to 70%, silica by weight. In another embodiment, such materials can have silica contents ranging from 15% to 60%, or from 25% to 50%, silica by weight. The solid oxides contemplated herein can have any suitable surface area, pore volume, and particle size, as would be recognized by those of skill in the art.

The electron-withdrawing component used to treat the oxide can be any component that increases the Lewis or Brønsted acidity of the solid oxide upon treatment (as compared to the solid oxide that is not treated with at least one electron-withdrawing anion). In one aspect, the electron-withdrawing component can be an electron-withdrawing anion derived from a salt, an acid, or other compound a volatile organic compound) that can serve as a source or precursor for that anion. In an aspect, electron-withdrawing anions include, but are not limited to, sulfate, bisulfate, fluoride, chloride, bromide, iodide, fluorosulfate, fluoroborate, phosphate, fluorophosphate, trifluoroacetate, tri flate, fluorozirconate, fluorotitanate, phospho-tungstate, tungstate, molybdate, and combinations thereof; alternatively, sulfate, bisulfate, fluoride, chloride, fluorosulfate, fluoroborate, phosphate, fluorophosphate, trifluoroacetate, triflate, fluorozirconate, fluorotitanate, and combinations thereof; alternatively, fluoride, chloride, bisulfate, sulfate, and combinations thereof; alternatively, sulfate, bisulfate, and combinations thereof; alternatively, fluoride, chloride, bromide, iodide, and combinations thereof; alternatively, fluorosulfate, fluoroborate, trifluoroacetate, triflate, fluorozirconate, fluorotitanate, trifluoroacetate, triflate, and combinations thereof; alternatively, fluoride, chloride, bromide, phosphate, triflate, bisulfate, sulfate, fluorophosphate, fluorosulfate, and combinations thereof; alternatively, fluoride, chloride, bisulfate, sulfate, or any combination thereof; alternatively, alternatively, fluoride, chloride, combinations thereof; or alternatively, bisulfate, sulfate, and combinations thereof. In some embodiments, the electron-withdrawing anion can comprise, consist essentially of, or consist of, sulfate; alternatively, bisulfate; alternatively, fluoride; alternatively, chloride; alternatively, bromide; alternatively, iodide; alternatively, fluorosulfate; alternatively, fluoroborate; alternatively, phosphate; alternatively, fluorophosphate; alternatively, trifluoroacetate; alternatively, triflate; alternatively, fluorozirconate; alternatively, fluorotitanate; alternatively, trifluoroacetate; or alternatively, triflate.

The chemically-treated solid oxide generally can contain from 1 wt. % to 25 wt. % of the electron-withdrawing anion, based on the weight of the chemically-treated solid oxide. In particular embodiments provided herein, the chemically-treated solid oxide can contain from 1 wt. % to 20 wt. %, from 2 wt. % to 20 wt. %, from 3 wt. % to 20 wt. %, from 2 wt. % to 15 wt. %, from 3 wt. % to 15 wt. %, from 3 wt. % to 12 wt. %, or from 4 wt. % to 10 wt. %, of the electron-withdrawing anion, based on the total weight of the chemically-treated solid oxide.

In another aspect and in any embodiment of this disclosure, the chemically-treated solid oxide can be fluorided alumina, chlorided alumina, bromided alumina, sulfated alumina, fluorided alumina, chlorided silica-alumina, bromided silica-alumina, sulfated silica-alumina, fluorided silica-zirconia, chlorided silica zirconia, bromided silica-zirconia, sulfated silica-zirconia, sulfated silica-zirconia, fluorided silica-titania, fluorided silica-coated alumina, fluorided-chlorided silica-coated alumina, sulfated silica-coated alumina, phosphated silica-coated alumina, or any combination thereof; alternatively, fluorided alumina, chlorided alumina, sulfated alumina, fluorided silica-alumina, chlorided silica-alumina, sulfated silica-alumina, fluorided silica-zirconia, sulfated silica-zirconia, sulfated silica-zirconia, fluorided silica-titania, fluorided silica-coated alumina, fluorided-chlorided silica-coated alumina, sulfated silica-coated alumina, or any combination thereof; alternatively, fluorided alumina; alternatively, chlorided alumina; alternatively, bromided alumina; alternatively, sulfated alumina; alternatively, fluorided silica-alumina; alternatively, chlorided silica-alumina; alternatively, bromided silica-alumina; alternatively, sulfated silica-alumina; alternatively, fluorided silica-zirconia; alternatively, chlorided silica-zirconia; alternatively, bromided silica-zirconia; alternatively, sulfated silica-zirconia; alternatively, sulfated silica-zirconia; alternatively, fluorided silica-titania; alternatively, fluorided silica-coated alumina; alternatively, fluorided-chlorided silica-coated alumina; alternatively, sulfated silica-coated alumina; or alternatively, phosphated silica-coated alumina.

Various processes can be used to form chemically-treated solid oxides useful in the present invention. Methods of contacting the solid oxide with the electron-withdrawing component, suitable electron withdrawing components and addition amounts, various calcining procedures and conditions (e.g., calcining temperatures in a range from 300° C. to 900° C., from 400° C. to 800° C., or from 500° C. to 700° C.), calcination times (e.g., calcination times in a range from 1 minute to 24 hours, from 5 minutes to 10 hours, or from 20 minutes to 6 hours), calcination equipment (e.g., calcination equipment such as a rotary kiln, muffle furnace, or fluidized bed, among other methods of conveying heat), and calcination atmosphere (e.g., dry or humid calcination atmospheres, oxidizing calcination atmospheres such as air or oxygen, reducing calcination atmospheres such as carbon monoxide or hydrogen, or non-reactive calcination atmospheres like nitrogen, argon or vacuum) are disclosed in U.S. Pat. Nos. 6,107,230, 6,165,929, 6,294,494, 6,300,271, 6,316,553, 6,355,594, 6,376,415, 6,391,816, 6,395,666, 6,524,987, 6,548,441, 6,750,302, 6,831,141, 6,936,667, 6,992,032, 7,601,665, 7,026,494, 7,148,298, 7,470,758, 7,517,939, 7,576,163, 7,294,599, 7,629,284, 7,501,372, 7,041,617, 7,226,886, 7,199,073, 7,312,283, 7,601,665, 7,619,047, 7,884,163, 8,309,485, and U.S. Publication No. 2010/0076167, among other patents and patent applications.

Various catalyst systems described herein (e.g., catalyst systems including a tnetallocene) also include an organoaluminum compound. In an aspect, organoaluminum compounds that can be used in any catalyst system of this disclosure include but are not limited to compounds having the formula:

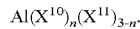

$Al(X^{10})_n(X^{11})_{3-n}$.

In an embodiment, each $X^{10}$ of the organoaluminum compound having the formula) $Al(X^{10})_n(X^{11})_{3-n}$ independently can be a $C_1$ to $C_{20}$ hydrocarbyl group; alternatively, a $C_1$ to $C_{10}$ hydrocarbyl group; alternatively, a $C_6$ to $C_{20}$ aryl group; alternatively, a $C_6$ to $C_{10}$ aryl group; alternatively, a $C_1$ to $C_{20}$ alkyl, group; alternatively, a $C_1$ to $C_{10}$ alkyl group; or alternatively, a $C_1$ to $C_5$ alkyl group. In an embodiment, each $X^{11}$ of the organoaluminum compound having the formula $Al(X^{10})_n(X^{11})_{3-n}$ independently can be a halide, a hydride, or a $C_1$ to $C_{20}$ hydrocarboxide group (also referred to as a hydrocarboxy group); alternatively, a halide, a hydride, or a $C_1$ to $C_{10}$ hydrocarboxide group; alternatively, a halide, a hydride, or a $C_6$ to $C_{20}$ aryloxide group (also referred to as an aroxide or aroxy group); alternatively, a halide, a hydride, or a $C_6$ to $C_{10}$ aryloxide group; alternatively, a halide, a hydride, or a $C_1$ to $C_{20}$ alkoxide group (also referred to as an alkoxy group); alternatively, a halide, a hydride, or a C to $C_{10}$ alkoxide, group; alternatively, a halide, a hydride, or, or a $C_1$ to $C_5$ alkoxide, group; alternatively, a halide; alternatively, a hydride; alternatively, a $C_1$ to $C_{20}$ hydrocarboxide group; alternatively, a $C_1$ to hydrocarboxide group; alternatively, a $C_6$ to $C_{20}$ aryloxide group; alternatively, a $C_6$ to $C_{10}$ aryloxide group; alternatively, a $C_1$ to $C_{20}$ alkoxide group; alternatively, a $C_1$ to $C_{10}$ alkoxide group; alternatively, a $C_1$ to $C_5$ alkoxide group. In an embodiment, n of the organoaluminum compound having the formula $Al(X^{10})_n(X^{11})_{3-n}$ can be a number (whole or otherwise) from 1 to 3, inclusive; alternatively, about 1.5; or alternatively, 3.

In an embodiment, each alkyl group(s) of the organoaluminum compound having the formula $Al(X^{10})_n(X^{11})_{3-n}$ independently can be a methyl group, an ethyl group, a butyl group, a hexyl group, or an octyl group. In some embodiments, each alkyl group(s) of the organoaluminum compound having the formula $Al(X^{10})_n(X^{11})_{3-n}$ independently can be a methyl group, an ethyl group, a n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group. In an embodiment, each aryl group of the organoaluminum compound having the formula) $Al(X^{10})_n(X^{11})_{3-n}$ independently can be a phenyl group or a substituted phenyl group; alternatively, a phenyl group; or alternatively, a substituted phenyl group.

In an embodiment, each halide of the organoaluminum compound having the formula) $Al(X^{10})_n(X^{11})_{3-n}$ independently can be a fluoride, chloride, bromide, or iodide. In some embodiments, each halide of the organoaluminum compound having the formula) $Al(X^{10})_n(X^{11})_{3-n}$ independently can be a fluoride; alternatively, chloride; alternatively, bromide; or alternatively, iodide.

In an embodiment, each alkoxide of the organoaluminum compound having the formula $Al(X^{10})_n(X^{11})_{3-n}$ independently can be a methoxy group, a ethoxy group, a butoxy group, a hexoxy group, or an octoxy group. In some embodiments, the alkoxy group independently can be a methoxy group, an ethoxy group, a n-butoxy group, or an iso-butoxy group; alternatively, a methoxy group; alternatively, an ethoxy group; alternatively, an n-propoxy group; alternatively, an n-butoxy group; alternatively, an iso-butoxy group; alternatively, a n-hexoxy group; or alternatively, an n-octoxy group. In an embodiment, each aryloxide of the organoaluminum compound having the formula $Al(X^{10})_n(X^{11})_{3-n}$ independently can be a phenoxide or a substituted phenoxide; alternatively, a phenoxide; or alternatively, a substituted phenoxide.

In an embodiment, the organoaluminum compound that can utilized in any aspect or embodiment of this disclosure can comprise, consist essentially of, or consist of, a trialkylaluminum, a dialkylaluminum halide, an alkylaluminum dihalide, a dialkylaluminum alkoxide, an alkylaluminum dialkoxide, a dialkylaluminum hydride, a alkylaluminum dihydride, and combinations thereof. In other embodiments, the organoaluminum compound that can utilized in any aspect or embodiment of this disclosure can comprise, consist essentially of, or consist of, a trialkylaluminum, a dialkylaluminum halide, an alkylaluminum dihalide, and combinations thereof; alternatively, a trialkylaluminum; alternatively, a dialkylaluminum halide; alternatively, an alkylaluminum dihalide; alternatively, a dialkylaluminum alkoxide; alternatively, an alkylaluminum dialkoxide; alternatively, a dialkylaluminum hydride; or alternatively, an alkylaluminum dihydride. In yet other embodiments, the organoaluminum compound that that can utilized in any aspect or embodiment of this disclosure can comprise, consist essentially of, or consist of, a trialkylaluminum, an alkylaluminum halide, or any combination thereof; alternatively, a trialkylaluminum; or alternatively, an alkylaluminum halide.

In a non-limiting embodiment, useful trialkylaluminum compounds can include trimethylaluminum, triethylaluminum, tripropylaluminum, tributylaluminum, trihexylaluminum, trioctylaluminum, or mixtures thereof. In some non-limiting embodiments, useful trialkylaluminum compounds can include trimethylaluminum, triethylaluminum, tripropylaluminum, tri-n-butylaluminum, tri-isobutylaluminum, tri-hexylaluminum, tri-n-octylaluminum, or mixtures thereof; alternatively, triethylaluminum, tri-n-butylaluminum, tri-isobutylaluminum, tri-n-hexylaluminum, tri-n-octylaluminum, or mixtures thereof; alternatively, triethylaluminum, tri-n-butylaluminum, tri-n-hexylaluminum, tri-n-octylaluminum, or mixtures thereof. In other non-limiting embodiments, useful trialkylaluminum compounds can be trimethylaluminum; alternatively, triethylaluminum; alternatively, tripropylaluminum; alternatively, tri-n-butylaluminum; alternatively, tri-isobutylaluminum; alternatively, hexylaluminum; or alternatively, tri-n-octylaluminum.

In a non-limiting embodiment, useful alkylaluminum halides can include diethylaluminum chloride, diethylaluminum bromide, ethylaluminum dichloride, ethylaluminum sesquichloride, and mixtures thereof. In some non-limiting embodiments, useful alkylaluminum halides can include diethylaluminum chloride, ethylaluminum dichloride, ethylaluminum sesquichloride, and mixtures thereof. In other non-limiting embodiments, useful alkylaluminum halides can be diethylaluminum chloride; alternatively, diethylaluminum bromide; alternatively, ethylaluminum dichloride; or alternatively, ethyl aluminum sesquichloride.

In an embodiment, the organoaluminum compound can be an aluminoxane, Aluminoxanes are independently described herein and these descriptions can be utilized without limitation to further describe the organoaluminum compound which can be utilized in the various aspects and embodiments described herein calling for an organoaluminum compound.

When the catalyst system comprises, consists essentially of, or consists of, a metallocene, and an organoaluminum compound, the catalyst system can comprise a minimum aluminum of organoaluminum compound to the metal of the metallocene molar ratio of 0.01:1, 0.02:1, 0.05:1, 0.1:1, 0.2:1, 0.5:1, 1:1 or 2:1; alternatively or additionally, a maximum aluminum of organoaluminum compound to the metal of the metallocene molar ratio of 10,000:1, 5,000:1, 1,000:1, 500:1, 100:1, 50:1, 25:1, 15:1, 10:1, or 5:1. Generally, the aluminum of organoaluminum compound to the metal of the metallocene molar ratio can range from any minimum value disclosed herein to any maximum value disclosed herein.

When the catalyst system comprises, consists essentially of, or consists of, a metallocene, a non-coordinating anion, and an organoaluminum compound, the catalyst system can comprise a minimum non-coordinating anion to metal of the metallocene molar ratio of 0.1:1, 0.2:1, 0.3:1, 0.5:1, 0.8:1, or 1:1; alternatively or additionally, a maximum non-coordinating anion to metal of the metallocene molar ratio of 10:1, 5:1, 3:1, or 2:1. When the catalyst system comprises, consists essentially of, or consists of a metallocene, a non-coordinating anion, and an organoaluminum compound, the catalyst system can comprise a minimum aluminum of organoaluminum compound to the metal of the metallocene molar ratio of 0.01:1, 0.02:1, 0.05:1, 0.1:1, 0.2:1, 0.5:1, 1:1 or 2:1; alternatively or additionally, a maximum aluminum of organoaluminum compound to the metal of the metallocene molar ratio of 10,000:1, 5,000:1, 1,000:1, 500:1, 100:1, 50:1. 25:1, 15:1, 10:1, or 5:1. Generally, the non-coordinating anion to metal of the metallocene molar ratio can range from any minimum value disclosed herein to any maximum value disclosed herein and/or the aluminum of organoaluminum compound to the metal of the metallocene molar ratio can range from any minimum value disclosed herein to any maximum value disclosed herein.

When the catalyst system comprises, consists essentially of, or consists of, a metallocene, a chemically-treated solid oxide, and an organoaluminum compound, the catalyst system can comprise a minimum chemically-treated solid oxide to metallocene weight ratio of 1:1, 10:1, 50:1, or 100:1; alternatively or additionally, a maximum chemically-treated solid oxide to metallocene weight ratio of 1,000,000:1, 100,000:1, 10,000:1, or 5,000:1. When the catalyst system comprises, consists essentially of, or consists of a metallocene, a chemically-treated solid oxide, and an organoaluminum compound, the catalyst system can comprise a minimum aluminum of the organoaluminum compound to metal of the metallocene molar ratio of 0.1:1, 1:1, 10:1, or 50:1; alternatively or additionally, a maximum aluminum of the organoaluminum compound to metal of the metallocene molar ratio of 10,000:1, 5,000:1, 1,000:1, or 500:1. When the catalyst system comprises, consists essentially of, or consists of a metallocene, a chemically-treated solid oxide, and an organoaluminum compound, the catalyst system can comprise a minimum organoaluminum compound to chemically-treated solid oxide weight ratio of 0.001:1, 0.01:1, or 0.2:1; alternatively or additionally, a maximum organoaluminum compound to chemically-treated solid oxide weight ratio of 5:1, 3:1, or 1:1. Generally, the chemically-treated solid oxide to metal of the metallocene molar ratio can range from any minimum value disclosed herein to any maximum value disclosed herein, the aluminum of organoaluminum compound to the metal of the metallocene molar ratio can range from any minimum value disclosed herein to any maximum value disclosed herein, and/or the organoaluminum compound to chemically-treated solid oxide weight ratio can range from any minimum value disclosed herein to any maximum value disclosed herein.

In an aspect, the catalyst system can comprise a supported metal oxide. In an embodiment, the catalyst system comprising a supported metal oxide can comprise a lower valence Group 6 metal oxide on an inert support. In some embodiments, the metal oxide can comprise chromium oxide. In some embodiments, the inert support can comprise, consist essentially of, or can be, silica, alumina, titania, silica alumina, magnesia, and the like, or combinations thereof. In particular embodiments, the inert support can have a pore opening of at least 40 angstroms.

The inert support can have a high surface area and large pore volumes. In some embodiments, the average pore size can be at 40 to 350 angstroms. High surface areas can be beneficial for supporting large amounts of highly dispersive, metal oxides (e.g., chromium oxide) to give maximum efficiency of metal usage and providing a very high activity catalyst. The support can have large average pore openings of at least 40 angstroms, with an average pore opening of 60 to 300 angstroms. Additional description of the supported metal oxide including specific metal oxide, specific supports (e.g., inert supports), methods of preparing the supported metal oxide, and method for oligomerizing olefins using the supported metal oxide can be found in U.S. Pat. No. 4,827,064.

In an aspect, the catalyst can comprise, can consist essentially of, or can be, a clay, an acidic clay, or an acid washed clay; alternatively, a clay; alternatively, an acidic clay; or alternatively, an acid washed clay. Generally, the clay, acidic clay, or acid washed clay can be any clay material that can catalyze the oligomerization of an olefin. In an embodiment, the clay can comprise, can consist essentially of, or can be, kaolinite, halloysite, vermiculite, chlorite, attapulgite, smectite, montmorillonite, illite, saconite, sepiolite, palygorskite, or any combination thereof. Generally, the acidic clay or acid washed clay can comprise, can consist essentially of, or can be, an acidic form or acid washed version of kaolinite, halloysite, vermiculite, chlorite, attapulgite, smectite, montmorillonite, illite, saconite, sepiolite, palygorskite, bentonite, or any combination thereof. In some embodiments, the acid washed clay can comprise, can consist essentially of, or can be, acid washed montmorillonite. Commercially available clays and acid washed clay which can be utilized as a catalyst can include those under the Filtrol® trademark designation.

In an aspect, the catalyst can comprise, consist essentially of, or consist of, an acidic ion exchange resin. Generally, the acidic ion exchange resin can be any acidic ion exchange resin which can oligomerize an olefin. In an embodiment, the acidic ion exchange resin can comprise, consist essentially of, or consist of, a functionalized styrene-divinylbenzene polymer resin, a functionalized polymer resin comprising units derived from styrene and units derived from divinyl benzene, a functionalized 4-vinylpyridine divinylbenzene polymer resin, a tetrafluoroethylene polymer resin modified with perfluorovinyl ether groups terminated with sulfonate groups, or any combination thereof. In some embodiments, the acidic ion exchange resin can comprise, consist essentially of, or consist of, a functionalized styrene-divinylbenzene polymer resin; alternatively, a functionalized polymer resin comprising units derived from styrene and units derived from divinyl benzene; alternatively, a functionalized 4-vinylpyridine divinylbenzene polymer resin; or alternatively, a tetrafluoroethylene polymer resin modified with perfluorovinyl ether groups terminated with sulfonate groups.

In an embodiment, functional groups which can be utilized in the functionalized styrene-divinylbenzene polymer resin, the functionalized polymer resin comprising units derived from styrene and units derived from divinyl benzene, and/or the functionalized 4-vinylpyridine divinylbenzene polymer resin can be an organic acid and/or an inorganic acid; alternatively, an organic acid; or alternatively, an inorganic acid. In some embodiments, the functional groups which can be utilized in the functionalized styrene-divinylbenzene polymer resin, the functionalized polymer resin comprising units derived from styrene and units derived from divinyl benzene, and/or the functionalized 4-vinylpyridine divinylbenzene polymer resin can be a carboxylic acid, a sulfonic acid, or any combination thereof; alternatively, a carboxylic acid; or alternatively, a sulfonic acid. In an embodiment, the carboxylic acid can be a $C_1$ to $C_{20}$ carboxylic acid; alternatively, a $C_1$ to $C_{15}$ carboxylic acid; or alternatively, a $C_1$ to $C_{10}$ carboxylic acid. In an embodiment, the sulfonic acid can be a $C_1$ to $C_{20}$ sulfonic acid; alternatively, a $C_1$ to $C_{15}$ sulfonic acid; or alternatively, a $C_1$ to $C_{10}$ sulfonic acid. In a non-limiting embodiment, the acid which can be utilized to functionalize the styrene-divinylbenzene polymer resin, the polymer resin comprising units derived from styrene and units derived from divinyl benzene, and/or the 4-vinylpyridine divinylbenzene polymer resin can comprise, consist essentially of, or consist of, benzoic acid, formic acid, acetic acid, propionic acid, butyric acid, oxalic acid, trifluoroacetic acid, trichloroacetic acid, sulfamic acid, benzene sulfonic acid, toluene sulfonic acid (ortho, meta, and/or para), dodecylbenzene sulfonic acid, naphthalene sulfonic acid, dinonylnaphthalene disulfonic acid, methane sulfonic acid, or any combination thereof; alternatively, benzoic acid, formic acid, acetic acid, propionic acid, butyric acid, oxalic acid, trifluoroacetic acid, trichloroacetic acid, or any combination thereof; or alternatively, benzene sulfonic acid, toluene sulfonic acid (ortho, meta, and/or para), dodecylbenzene sulfonic acid, naphthalene sulfonic acid, dinonylnaphthalene disulfonic acid, methane sulfonic acid, or any combination thereof.

In other embodiments, the acidic ion exchange resin can comprise, consist essentially of, or consist of, a sulfonated styrene-divinylbenzene polymer resin, a sulfonated polymer resin comprising units derived from styrene and units derived from divinyl benzene, a sulfonated 4-vinylpyridine divinylbenzene polymer resin, or any combination thereof; alternatively, a sulfonated styrene-divinylbenzene polymer resin; alternatively, a sulfonated polymer resin comprising units derived from styrene and units derived from divinyl benzene; or alternatively, a sulfonated 4-vinylpyridine divinylbenzene polymer resin. In an embodiment, these sulfonated polymer resins when utilized as the catalyst can be in $H^+$ form (i.e., protonated form).

Commercially available acidic ion exchange resins that can be employed as the catalyst in the processes disclosed herein can include AMBERLYST® resins, NAFION® resins, or any combination thereof. Thus, for example, the acidic ion exchange resins can comprise an AMBERLYST® resin; or alternatively, a NAFION® resin. Various grades of the AMBERLYST® resin and/or the NAFION® resin can be used as the acidic ion exchange resins. While not limited thereto, the acidic ion exchange resins can comprise, consist essentially of, or consist of, AMBERLYST® 15 resin, AMBERLYST® 31 resin, AMBERLYST® 35 resin, AMBERLYST® 36 resin, AMBERLYST® DT resin, or any combination thereof; alternatively, AMBERLYST® 15 resin; alternatively, AMBERLYST® 31 resin; alternatively, AMBERLYST® 35 resin; alternatively, AMBERLYST® 36 resin; or alternatively, AMBERLYST® DT resin. In other embodiments, the acidic ion exchange resins can comprise, consist essentially of, or consist of, Nafion® NR50, NAFION® SAC-13, or NAFION® trimethylsilylated; alternatively, NAFION® NR50; alternatively, NAFION® SAC-13; or alternatively, NAFION® trimethylsilylated.

Combinations of more than one catalyst systems described herein can be employed, if desired. Moreover, the processes disclosed herein are not limited solely to the catalyst systems provided hereinabove.

In an embodiment, processes for producing the compositions disclosed herein can be either continuous or batch. In an aspect, the olefin monomers can be added to the catalyst system; alternatively, the catalyst system can be added to the olefin monomers; or alternatively, the catalyst system and the olefin monomers can be simultaneously introduced into a reaction zone.

Some of the processes to produce the compositions disclosed herein can be continuous processes. In an embodiment, the process to produce the compositions disclosed herein comprise the introduction of olefin monomers and catalyst system into a reaction zone and withdrawing from the reaction zone a reaction effluent comprising olefin oligomers, as described herein.

The reaction zone of the process can be defined by any reaction zone means known in the art that can provide conditions to form the olefin oligomers. The reaction zone can comprise, or can be, a reactor vessel into which the olefin monomers, the catalyst system, and/or any other desired components (e.g., promoter, solvent, hydrogen, among other components described herein) can be introduced. The olefin monomers, the catalyst system, and/or any other desired components (e.g., promoter, solvent, hydrogen, among other components described herein) can be introduced separately into the reaction zone as separate feed streams, introduced as one or more mixtures, or they can be introduced together as a premixed mixture. A suitable reaction zone can be compatible with a continuous, semi-continuous, or batch process. In an embodiment, the reaction zone can comprise a continuous stirred tank reactor (CSTR), a plug flow reactor, a fixed bed reactor, or any combination thereof. In some embodiments, the reaction zone of any process, system, or reaction system described herein can comprise an autoclave reactor, continuous stirred tank reactor, a loop reactor, a solution reactor, a tubular reactor, or a recycle reactor.

The conditions capable of forming olefin oligomers disclosed herein within the reaction zone can be maintained to provide the oligomerization of the olefin monomer to form olefin oligomers. In an embodiment, the conditions capable of forming olefin oligomers can comprise a temperature, a pressure, a time, or any combination thereof; alternatively, a temperature and a pressure; alternatively, a temperature and a time; or alternatively, a temperature, a pressure and a time; alternatively, a temperature; alternatively, a pressure; or alternatively, a time.

In an embodiment, the reaction zone can operate at any pressure that can facilitate the formation of the olefin oligomers. In an embodiment, the pressure at which the reaction zone can operate can be any pressure that produces the desired olefin oligomers. In an embodiment, the minimum pressure which can be utilized as a condition capable of forming the olefin oligomers can be 0 psig (0 kPa), or 0.1 psig (0.69 KPa). In an embodiment, the maximum pressure which can be utilized as a condition capable of forming the olefin oligomers can be 4,000 psig (27.6 MPa), 2,000 psig (13.8 MPa), 1,000 psig (6.9 MPa), 500 psig (3.4 MPa), 250 psig (1.7 MPa), or 150 psig (1.0 MPa). In an embodiment, the pressure which can be utilized as a condition capable of forming the olefin oligomers can range from any minimum pressure which can be utilized as a condition capable of forming the olefin oligomers to any maximum pressure which can be utilized as a condition capable of forming the olefin oligomers described herein. In some embodiments, suitable ranges for the pressure which can be utilized as a condition capable of forming the olefin oligomers can include, but are not limited to, from 0 psig (0 KPa) to 4,000 psig (27.6 MPa); alternatively, 0.1 psig (0.69 KPa) to 2,000 psig (13.8 MPa); alternatively, 0.1 psig (0.69 KPa) to 1,000 psig (6.9 MPa); alternatively, 0.1 psig (0.69 KPa) to 500 psig (3.4 MPa); alternatively, 0.1 psig (0.69 KPa) to 250 psig (1.7 MPa); or alternatively, 0.1 psig (0.69 KPa) to 150 psig (1.0 MPa). Other suitable pressure ranges which can be utilized as a condition capable of forming the olefin oligomers are readily apparent from the present disclosure.

In an embodiment, a minimum temperature at which the olefin oligomers can be formed can be 0° C., 5° C., 10° C., 15° C., 20° C., or 25° C. In an embodiment, the maximum temperature which can be utilized as a condition capable of forming the olefin oligomers can be 300° C., 250° C., 200° C., 180° C., 160° C., 140° C., 120° C., or 120° C. In some embodiments, the temperature at which the olefin oligomers can be formed can range from any minimum temperature described herein to any maximum reaction temperature described herein as long as the maximum temperature is greater than the minimum temperature. Without wishing to be limited by theory, one of skill in the art will recognize that the temperature at which the olefin oligomers can be formed can be dependent upon the catalyst system utilized to form the olefin oligomers. Consequently, in an embodiment, the temperature at which the olefin oligomers product (e.g., olefin oligomers as disclosed herein) can be formed can range from 0° C. to 300° C.; alternatively, 0° C. to 200° C.; alternatively, 5° C. to 180° C.; alternatively, from 15° C. to 160° C.; alternatively, from 20° C. to 140° C.; alternatively, from 30° C. to 140° C.; alternatively, from 30° C. to 120° C.; alternatively, from 30° C. to 100° C.; alternatively, from 40° C. to 100° C.; alternatively, from 50° C. to 130° C.; alternatively, from 60° C. to 120° C.; alternatively, from 50° C. to 100° C.; alternatively, from 60° C. to 140° C.; or alternatively, from 60° C. to 120° C.; or alternatively, from 80° C. to 100° C. Other temperature ranges at which the olefin oligomers can be formed can be understood by those skilled in the art with the help of this disclosure.

Generally, the time over which the olefin oligomers can be formed can be any time which can provide the desired monomer conversion and/or desired olefin oligomer distribution. In relation to continuous processes, the time over which the olefin oligomers can be formed as a condition capable of forming an olefin oligomers can be the ratio of the reactor zone volume to the volumetric introduction rate of any of the feeds, (e.g., the monomer, the catalyst (or the catalyst system), and any other components (e.g., promoter, among other components described herein)) charged to or introduced into the reaction zone. It should be noted that in some situations the time can be the average amount of time (e.g., the average residence time) that the particular materials (e.g., the monomer and/or the catalyst system), and any other components (e.g., promoter, among other components described herein), among others) spend within the reaction zone. The minimum time (or minimum average time) can be 1 minute, 2 minutes, 4 minutes, 6 minutes, 8 minutes, or 10 minutes. The maximum time (or average maximum time) can be 90 minutes, 2 hours, 4 hours, 6 hours, 8 hours, or 10 hours. In an embodiment, the time (or average time) which can be utilized as a condition capable of forming the olefin oligomers can range from any minimum time (or average minimum time) which can be utilized as a condition capable of forming the olefin oligomers to any maximum time (or average maximum time) which can be utilized as a condition capable of forming the olefin oligomers described herein. In some embodiments, the time (or average time) which can be utilized as a condition capable of forming the olefin oligomers can range, but is not limited to, from 1 minute to 10 hours; alternatively, from 2 minutes to 8 hours; alternatively, from 4 minutes to 6 hours; alternatively, from 6 minutes to 4 hours; alternatively, from 8 minutes to 2 hours; or alternatively, from 10 minutes to 90 minutes. Other suitable time ranges (or average time ranges) which can be utilized as a condition capable of forming the olefin oligomers are readily apparent from the present disclosure. In an embodiment, an olefin conversion can be at least 30 wt. % percent; alternatively, at least 35 wt. % percent; alternatively, at least 40 wt. % percent; or alternatively, at least 45 wt. % percent.

In an embodiment, the olefin oligomers can be formed in the presence of hydrogen. In the process embodiments disclosed herein, hydrogen can be added to the reaction zone to accelerate the reaction and/or increase catalyst system activity. If desired, hydrogen can also be added to suppress polymer production. When hydrogen is utilized, a hydrogen partial pressure at which the olefin oligomers can be formed can range from 2 psi to 100 psi; alternatively, 5 psi to 75 psi; or alternatively, 10 psi to 50 psi.

In an embodiment, processes for producing the compositions disclosed herein can further comprise removing a reaction zone effluent from the reaction zone. For purposes of the disclosure herein, the term "reaction zone effluent," and its derivatives generally refers to all the material which exits the reaction zone (e.g., olefin monomers, catalyst system or catalyst system components, olefin oligomers, and/or optional reaction zone diluent or solvent). The term "reaction zone effluent" and its derivatives can be qualified to refer to certain portions by use of additional qualifying terms. For example, the reaction zone effluent refers to all material which exits the reaction zone, while the term "reaction zone olefin oligomer effluent" refers to only the olefin oligomers within the reaction zone effluent.

In an embodiment, the reaction zone effluent can comprise olefin oligomers of any olefin monomer, unreacted olefin monomers comprising branched $C_{10}$ olefin monomers, catalyst system and/or catalyst system components, and/or optional reaction zone diluent. In some embodiments, the reaction zone effluent can be treated and subjected to one or more separation processes to recover components from the reaction zone effluent (e.g., unreacted olefin monomers, optional diluent or solvent, olefin oligomers, and/or by-product(s), among others).

In an embodiment, the processes for producing the compositions disclosed herein can further comprise contacting the reaction zone effluent with a catalyst (or catalyst system) deactivating agent to form a deactivated reaction zone effluent. Generally, the reaction zone effluent contacted with the catalyst system deactivating agent can comprise the olefin monomers of the monomer feedstock, the olefin oligomers, the catalyst or catalyst system, and/or the optional reaction zone diluent, among other components. A deactivated reaction zone effluent generally represents the reaction zone effluent which has been contacted with the catalyst system deactivating agent, and can generally comprise olefin monomers of the monomer feedstock, the olefin oligomers, deactivated catalyst or catalyst system, and/or the optional reaction zone solvent, among other components.

Generally, the catalyst (or catalyst system) can be deactivated using any method or material which can deactivate the catalyst (or catalyst system) for converting the monomer to the olefin oligomers. In an embodiment, the deactivation of the catalyst (or catalyst system) can occur in a reaction zone in which the olefin oligomers are formed; or alternatively, a reaction zone effluent can be removed from the reaction zone in which the olefin oligomers are formed and the deactivation of the catalyst (or catalyst system) can occur in a vessel, transfer line, or a reactor (among other choices) different from the reaction zone in which the olefin oligomers are formed. In an embodiment, the catalyst (or catalyst system) can be deactivated by contacting the reaction zone effluent with a catalyst (or catalyst system) deactivating agent comprising a solution comprising water and substantially devoid of a Group 1 or Group 2 metal hydroxide; or alternatively, a catalyst (or catalyst system) deactivating agent comprising an aqueous solution comprising a Group 1 and/or Group 2 metal hydroxide. As utilized herein, substantially devoid of a Group 1 or Group 2 metal hydroxide refers to a solution containing less than 500 ppm (by weight) of a Group 1 or Group 2 metal hydroxide. In an embodiment, the reactor effluent can comprise monomer, catalyst (or catalyst system or catalyst system components), and olefin oligomers; or alternatively, monomer, catalyst (or catalyst system or catalyst system components), olefin oligomers, and organic diluent (if utilized). In an embodiment, the Group 1 metal hydroxide utilized in the aqueous solution comprising Group 1 and/or Group 2 metal hydroxide can comprise, consist essentially of, or consist of, lithium hydroxide, sodium hydroxide, potassium hydroxide, rubidium hydroxide, cesium hydroxide, or any combination thereof. In an embodiment, the Group 2 metal hydroxide utilized in the aqueous solution comprising the Group 1 and/or Group 2 metal hydroxide can comprise, consist essentially of, or consist of, beryllium hydroxide, magnesium hydroxide, calcium hydroxide, strontium hydroxide, or barium hydroxide, or any combination thereof. In some embodiments, after the reaction zone effluent is contacted with the solution comprising water and substantially devoid of a Group 1 or Group 2 metal hydroxide or the aqueous solution comprising the Group 1 and/or Group 2 metal hydroxide, the organic layer/phase comprising the olefin oligomers (or comprising the olefin oligomers and monomer) can be separated from the aqueous layer/phase comprising the Group 1 and/or Group 2 metal hydroxide, to yield a separated organic layer/phase and a separated aqueous layer/phase. In some embodiments, the separated organic layer/phase can be washed with a solution comprising water and substantially devoid of a Group 1 or Group 2 metal hydroxide, and the organic layer/phase can then be separated from the aqueous layer/phase. In some embodiments, the solution comprising water and substantially devoid of a Group 1 or Group 2 metal hydroxide or the aqueous solution comprising a Group 1 and/or Group 2 metal hydroxide can contain one or more additional components which can facilitate the contacting of the aqueous solution and the reaction zone effluent and/or components which can facilitate the separation of the aqueous layer/phase from the organic layer/phase. Generally, the separated organic layer/phase can comprise monomer and olefin oligomers; or alternatively, monomer, olefin oligomers, and organic diluent (if utilized).

In an embodiment, the reaction zone effluent can comprise components present in the reaction mixture, as previously discussed herein. For example, in an olefin monomer oligomerization, the reaction zone effluent can generally include olefin monomers (e.g. monomer feedstock), the olefin oligomers (e.g., olefin oligomers of one or more olefin monomers, the olefin monomers comprising a branched $C_{10}$ olefin monomer), the catalyst system, and/or the optional reaction zone solvent, among other components. A deactivated reaction zone effluent generally represents the reaction zone effluent which has been contacted with the catalyst system deactivating agent, and generally comprises olefin monomers (e.g., monomer feedstock), the olefin oligomers (e.g., olefin oligomers of one or more olefin monomers, the olefin monomers comprising a branched $C_{10}$ olefin monomer), the deactivated catalyst system, and/or the reaction zone solvent, among other components.

In an embodiment, the processes disclosed herein can include a step of separating the olefin oligomers (or a portion of the olefin oligomers) from the monomer feedstock; alternatively, the monomer feedstock and organic diluent (if utilized), to yield a separated olefin oligomer stream. In some embodiments, the catalyst (or catalyst system) can be deactivated prior to separating the olefin oligomers (or a portion of the olefin oligomers) from the monomer feedstock (or the monomer feedstock and organic diluent). In other embodiments, the catalyst (or catalyst system) can be separated from the olefin oligomers (or a portion of the olefin oligomers) during the separation of the olefin oligomers (or a portion of the olefin oligomers) from the monomer feedstock (or the monomer feedstock and organic diluent).

In an embodiment, a process for producing the compositions disclosed herein can further comprise removing at least a portion of the monomer feedstock from the reaction zone effluent or deactivated reaction zone effluent. Any separation process or combination of processes can be used to remove at least a portion of the monomer feedstock from the reaction zone effluent or deactivated reaction zone effluent, including, for example, distillation. In one or more embodiments, the separation process for at least a portion of the monomer feedstock can comprise at least one separation vessel comprising columns, tanks, flash vessels, distillation columns, or combinations thereof. In some embodiments, the recovered monomer feedstock obtained by removing at least a portion of the monomer feedstock from the reaction zone effluent or deactivated reaction zone effluent can be recycled to the reaction zone.

In an embodiment, a process for producing the compositions disclosed herein can further comprise separating the olefin oligomers (or alternatively, one or more fractions comprising all or a portion of the olefin oligomers) from the monomer, the catalyst (catalyst system; deactivated catalyst; or deactivated catalyst system), and the organic diluent (if utilized). In an embodiment, a process for producing the compositions disclosed herein can further comprise isolating one or more fractions comprising all or a portion of the olefin oligomers from the reaction zone effluent and/or deactivated reaction zone effluent. Any separation process or combination of processes can be used to isolate the one or more fractions comprising all or a portion of the olefin oligomers from the reaction zone effluent and/or deactivated reaction zone effluent, including, for example, distillation. In one or more embodiments, the separation process can comprise at least one separation vessel comprising columns, tanks, flash vessels, distillation columns, or combinations thereof. In some embodiments, the separation process to isolate one or more fractions comprising all or a portion of the olefin oligomers can comprise removing at least a portion of the monomer feedstock from the reaction zone effluent and/or deactivated reaction zone effluent, prior to isolating one or more fractions comprising all or a portion of the olefin oligomers from the reaction zone effluent and/or deactivated reaction zone effluent.

In an embodiment, a process for producing the compositions disclosed herein can further comprise hydrogenating at least one of the one or more fractions comprising all or a portion of the olefin oligomers. In an embodiment, any one (or more than one) of the one or more fractions comprising all or a portion of the olefin oligomers can be hydrogenated. Each of the hydrogenated one of the one or more fractions comprising all or a portion of the olefin oligomers can represent a substantially hydrogenated olefin oligomer composition described herein.

Following the separation of the one or more fractions comprising all or a portion of the olefin oligomers, the residual unsaturation in the olefin oligomers can be reduced by hydrogenating at least one of the one or more fractions comprising all or a portion of the olefin oligomers to form the substantially hydrogenated olefin oligomers. The hydrogenation can be accomplished by any means known to those with ordinary skill in the art. In an embodiment, all or a portion of the olefin oligomers can be separated from the monomer feedstock. In some embodiments, the olefin oligomers can be separated (either concurrently with the separation from the monomer feedstock or as a separation distinct from the separation from the monomer feedstock) into one or more fractions comprising, or consisting essentially of, olefin oligomers, as previously described herein. Any one or more of the one or more fractions comprising all or a portion of the olefin oligomers can be separately fed to a hydrogenation unit to hydrogenate unsaturated double bonds and produce hydrogenated olefin oligomers. In some embodiments, the separated one or more fractions comprising all or a portion of the olefin oligomers can be stored prior to hydrogenation. In an embodiment, the processes described herein can further comprise isolating one or more fractions from any of the hydrogenated one or more fractions comprising all or a portion of the olefin oligomers. Each of the isolated one or more fractions of the hydrogenated one or more fractions comprising all or a portion of the olefin oligomers can also represent a composition comprising substantially hydrogenated olefin oligomers.

In an embodiment, any of the one or more fractions comprising all or a portion of the olefin oligomers can be hydrogenated by reaction with hydrogen gas to form substantially hydrogenated olefin oligomers. Generally, the hydrogenation can comprise contacting any of the one or more fractions comprising all or a portion of the olefin oligomers and a hydrogenation catalyst to form substantially hydrogenated olefin oligomers. In an embodiment the hydrogenation can be performed under conditions capable of hydrogenating the olefin oligomers (or forming substantially hydrogenated olefin oligomers). In some embodiments, the one or more fractions comprising all or a portion of the olefin oligomers can be hydrogenated to produce the substantially hydrogenated olefin oligomers having any bromine number or bromine index described herein.

In an embodiment, the hydrogenation catalyst can comprise, or consist essentially of, a supported Group 7, 8, 9, and 10 metals. In some embodiments, the hydrogenation catalyst can be selected from the group consisting of one or more of Ni, Pd, Pt, Co, Rh, Fe, Ru, Os, Cr, Mo, and W, supported on silica, alumina, clay, titania, zirconia, or a mixed metal oxide supports. In other embodiments, the hydrogenation catalyst can be nickel supported on kieselguhr, platinum or palladium supported on alumina, or cobalt-molybdenum supported on alumina; alternatively, nickel supported on kieselguhr; alternatively, platinum or palladium supported on alumina; or alternatively, cobalt-molybdenum supported on alumina. In yet other embodiments, the hydrogenation catalyst can be one or more of the group consisting of nickel supported on kieselguhr, silica, alumina, clay or silica-alumina.

Generally, the hydrogenation can be performed in any type of process and/or reactor which can hydrogenate the olefin oligomers to the desired bromine number or bromine index. In an embodiment, the hydrogenation can be performed in a batch process, a continuous process; or any combination thereof, alternatively a batch process; or alternatively a continuous process. In some embodiments, the hydrogenation can be performed in a slurry reactor, a continuous stirred tank reactor, a fixed bed reactor, or any combination thereof; alternatively, a slurry reactor; alternatively, a continuous stirred tank reactor; or alternatively, a fixed bed reactor. Generally, the substantially hydrogenated olefin oligomers can be filtered to separate the hydrogenation catalyst and/or catalyst fines from the substantially hydrogenated olefin oligomers. Further, the substantially hydrogenated olefin oligomers can be distilled to further purify the substantially hydrogenated olefin oligomers; alternatively, distilled to form two or more fractions comprising, or consisting essentially of substantially hydrogenated olefin oligomers having different nominal viscosities; or alternatively, distilled to further purify the substantially hydrogenated olefin oligomers and form two or more fractions comprising, or consisting essentially of substantially hydrogenated olefin oligomers having different nominal viscosities.

The quantity of hydrogenation catalyst utilized can be dependent upon the identity of the hydrogenation catalyst and the particular hydrogenation process utilized. Generally, the amount of hydrogenation catalyst used can be any amount which can produce substantially hydrogenated olefin oligomers having a desired bromine number (or bromine index). In a non-fixed bed hydrogenation process (e.g., slurry reactors or continuous stirred tank reactors, among others), the amount of hydrogenation catalyst used in the hydrogenation can range from 0.001 wt. % to 20 wt. %, from 0.01 wt. % to 15 wt. %, from 0.1 wt. % to 10 wt. %, or from 1 wt. % to 5 wt. %. In a fixed bed processes, the WHSV (weight hourly space velocity) of the olefin oligomers over the hydrogenation catalyst can range from 0.01 to 10, from 0.05 to 7.5, or from 0.1 to 5. The wt. % of the hydrogenation catalyst is based upon the total weight of the hydrogenation catalyst and the olefin oligomers subjected to hydrogenation.

Generally, the conditions capable of hydrogenating the olefin oligomers (or forming the substantially hydrogenated olefin oligomers) can comprise a hydrogen pressure, a temperature, a contact time, or any combination thereof; alternatively, a hydrogen pressure and a temperature; alternatively, a hydrogen pressure, a temperature, and a contact time; alternatively, a hydrogen pressure; alternatively, a temperature; or alternatively, a contact time. In an embodiment, the temperature of the hydrogenation that can be utilized can range from 25° C. to 350° C., from 50° C. to 300° C., from 60° C. to 250° C., or from 70° C. to 200° C. In an embodiment, the hydrogen pressure that can be utilized can range from 100 kPa to 10 MPa, from 250 kPa to 7 MPa, from 500 kPa to 5 MPa, or from 750 kPa to 2 MPa. In an embodiment, the contact time that can be utilized can range from 1 minute to 100 hours, from 2 minutes to 50 hours, from 5 minutes to 25 hour, or from 10 minute to 10 hours. Additional information on the hydrogenation of olefin oligomers to form substantially hydrogenated olefin oligomers can be found in U.S. Pat. No. 5,573,657; and "Lubricant Base Oil Hydrogen Refining Processes," pages 119 to 152 of Lubricant Base Oil and Wax Processing, by Avilino Sequeira, Jr., Marcel Dekker, Inc., N.Y. (1994).

In an embodiment, processes described herein can further comprise isolating one or more fractions from the hydrogenated one or more fractions comprising all or a portion of the olefin oligomers. After one or more fractions comprising all or a portion of the olefin oligomers has been hydrogenated, one or more fractions of the hydrogenated one or more fraction comprising all or a portion of the olefin oligomers can be isolated from any of the hydrogenated one or more fractions comprising all or a portion of the olefin oligomers. Any of these isolated one or more fractions of the hydrogenated one or more fractions comprising all or a portion of the olefin oligomers can represent substantially hydrogenated olefin oligomers described herein. Any separation process or combination of processes can be used to isolate one or more fractions from the hydrogenated one or more fractions comprising all or a portion of the olefin oligomers, including, for example, distillation. In one or more embodiments, the separation process for isolating one or more fractions from the hydrogenated one or more fractions comprising all or a portion of the olefin oligomers can comprise at least one separation vessel comprising columns, tanks, flash vessels, distillation columns, or combinations thereof.

In an embodiment, the olefin oligomers, any one or more of the at least one of the one or more fractions comprising all or a portion of the olefin oligomers, the hydrogenated olefin oligomers, or any one or more of the at least one of one or more fractions of the hydrogenated one or more fractions comprising all or a portion of the olefin oligomers (or substantially hydrogenated olefin oligomers), can have a 100° C. kinematic viscosity of from 1.5 cSt to 225 cSt; from 1.5 cSt to 12 cSt; from 15 cSt to 40 cSt; or from 40 cSt to 150 cSt. In other embodiments, the olefin oligomers, any one or more of the at least one of the one or more fractions comprising all or a portion of the olefin oligomers, the hydrogenated olefin oligomers, or any one of more of the at least one of one or more fractions of the hydrogenated one or more fractions comprising all or a portion of the olefin oligomers (or substantially hydrogenated olefin oligomers), can have a 100° C. kinematic viscosity of from 1.8 cSt to 2.2 cSt, from 2.3 cSt to 2.7 cSt, from 2.6 cSt to 3.4 cSt, from 3.6 cSt to 4.4 cSt, from 4.6 cSt to 5.4 cSt, from 5.6 cSt to 6.4 cSt, from 6.6 cSt to 7.4 cSt, from 7.6 cSt to 8.4 cSt, from 8.6 cSt to 9.4 cSt, or from 9.6 cSt to 10.4 cSt. As will be appreciated by one of skill in the art, and with the help of this disclosure, these kinematic viscosity value ranges correspond to olefin oligomers and/or substantially hydrogenated olefin oligomers produced using the various catalyst systems disclosed herein. The 100° C. kinematic viscosity of the compositions described herein can be measured using ASTM D445-12.

In an aspect, the substantially hydrogenated olefin oligomers described herein can be further used in a variety of components or products for a diverse range of applications and industries. For example, the substantially hydrogenated olefin oligomers can be utilized as a lubricant base oil (or a component of a lubricant base oil) for lubricant compositions and/or functional fluid compositions. Exemplary lubricant compositions in which the substantially hydrogenated olefin oligomers produced by the processes described herein can be utilized include, but are not limited to, greases, gearbox oils, engine oils, transmission fluids, and/or drilling fluids. Exemplary functional fluid compositions in which the substantially hydrogenated olefin oligomers produced by the processes described herein can be utilized include, but are not limited to, hydraulic fluids, drilling fluids, coolant fluids, and/or dielectric coolant fluids. In an aspect, the substantially hydrogenated olefin oligomers produced by a processes described herein can be utilized as the sole Base Oil for a lubricant composition and/or functional fluid composition. In other aspects, the substantially hydrogenated olefin oligomers produced by a process described herein can be combined with one or more other Base Oils to form a Base Oil for a lubricant composition and/or functional fluid composition. In an embodiment, the substantially hydrogenated olefin oligomers produced by a processes described herein can be blended with a Group I Base Oil, Group II Base Oil, Group III Base Oil, another Group IV Base Oil, a Group V Base Oil, or any combination of thereof to form a lubricant base oil for lubricant compositions and/or functional fluid compositions. As utilized herein, the Base Oil groups are those as designated by The American Petroleum Institute (API). Additional information on the use of substantially hydrogenated olefin oligomers in lubricant compositions and/or functional fluid compositions can be found in "Synthetic Lubricants and High-Performance Functional Fluids," 2nd Ed., L. Rudnick, ed., Marcel Dekker, Inc., N.Y. (1999). Additional information on additives used in product formulation can be found in "Lubricants and Lubrications," T. Mang and W. Dresel, eds., Wiley-VCH GmbH, Weinheim (2001).

Fully formulated lubricants can further include one or more additives. Additives which can be include in a fully formulated lubricant can include but are not limited to viscosity index improvers/viscosity modifiers/viscosity improver, dispersants (metallic and/or non-metallic), detergents (metallic and/or non-metallic), friction modifiers, traction improving additives, demulsifiers, defoamants, antioxidants, anti-wear additives (metallic and non-metallic, phosphorus-containing and non-phosphorus, sulfur-containing and non-sulfur types), extreme-pressure additives (metallic and non-metallic, phosphorus-containing and non-phosphorus, sulfur-containing and non-sulfur types), anti-rust additives, corrosion inhibitors, metal deactivators, anti-seizure agents, pour point depressants, wax modifiers, seal compatibility agents, friction modifiers, lubricity agents, anti-staining agents, chromophores (dyes), and/or haze inhibitors. Additional information on additives used in product formulations can be found in "Fuels and Lubricants Handbook: Technology, Properties, Performance, and Testing" edited by George E. Totten, Steven R. Westbrook, Rajesh J. Shah, ASTM (2003), ISBN 0-8031-2096-6; Chapter 9 Additives and Additive Chemistry, pp. 199-248, "Lubricants and Related Products," Klamann, Verlag Chemie, Deerfield Beach, Fla., ISBN 0-89573-177-0; "Lubricant Additives" by M. W. Ranney, published by Noyes Data Corporation of Parkridge, N.J. (1973); "Lubricants and Lubrications," T. Mang and W. Dresel, eds., Wiley-VCH GmbH, Weinheim (2001); and "Lubricant Additives", C. V. Smallheer and R. K. Smith, published by the Lezius-Hiles Co. of Cleveland, Ohio (1967).

Viscosity index improvers (also known as viscosity modifiers and viscosity improvers) can provide lubricant compositions and/or functional fluid compositions with high and low temperature operability. These additives can impart shear stability at elevated temperatures and acceptable viscosity at low temperatures. Suitable viscosity index improvers can include high molecular weight hydrocarbons, olefin polymers and copolymers, polyesters, and viscosity index improver dispersants that function as both a viscosity index improver and a dispersant. Viscosity index improvers can have molecular weights ranging from about 10,000 Da to about 1,000,000 Da, from about 20,000 Da to about 500,000 Da, or from about 50,000 Da to about 200,000 Da. Viscosity index improvers can include polymers and copolymers of methacrylate, butadiene, olefins, or alkylated styrenes. Exemplary viscosity index improvers include, but are not limited to, polyisobutylene, copolymers of ethylene and propylene, hydrogenated block copolymers of styrene and isoprene, polyacrylates (e.g., polymers and/or copolymers of various chain length acrylates), and polymethacrylates (e.g., polymer and/or copolymers of various chain length alkyl methacrylates. Generally, the viscosity index improver can be used in an amount of from 0.01 wt. % to 6 wt. %, from 0.01 to 5 wt. %, or from 0.01 to 4 wt. % based upon the total weight of the composition.

Dispersants are additives utilized to maintain oxidation products (produced during use of the lubricant composition) in suspension in the lubricant compositions and/or functional fluid compositions to prevent the accumulation of debris that could score bearings, block lubricant pathways, prevent deposit formations, inhibit corrosive wear by neutralizing acidic products (e.g., combustion products), and other types of damage. Dispersants can be ash-containing or ashless in character. Dispersants can include, but are not limited to alkenylsuccinic acid or anhydride derivatives (e.g., succinimides, succinate esters, or succinate ester amides), phenates, Mannich-Base condensates (e.g., the condensation products of alkylphenols, amines and aldehydes), hydrocarbyl substituted amines, sulfonates, sulfurized phenates, salicylates, naphthenates, stearates, carbamates, thiocarbamates, and phosphorus derivatives in metallic and non-metallic versions. Suitable dispersants can contain a polar group attached to a relatively high molecular weight hydrocarbon chain where the polar group contains at least one element of nitrogen, oxygen, or phosphorus. Patents describing dispersants which can be utilized in the lubricant compositions and/or functional fluid compositions include, but are not limited to, U.S. Pat. Nos. 3,036,003; 3,087,936; 3,172,892; 3,200,107; 3,215,707; 3,219,666; 3,254,025; 3,272,746; 3,275,554; 3,322,670; 3,329,658; 3,316,177; 3,438,757; 3,341,542; 3,413,347; 3,438,757; 3,444,170; 3,449,250; 3,454,555; 3,454,607; 3,519,565; 3,541,012; 3,565,804; 3,630,904; 3,632,511; 3,652,616; 3,666,730; 3,687,849; 3,697,574; 3,702,300; 3,703,536; 3,704,308; 3,725,277; 3,725,480; 3,726,882; 3,751,365; 3,755,433; 3,756,953; 3,787,374; 3,798,165; 3,803,039; 3,822,209; 3,948,800; 4,100,082; 4,234,435; 4,426,305; 4,454,059; 4,767,551; and 5,705,458, among others. Generally, dispersants can be used in an amount of about 0.1 wt. % to 20 wt. %, 0.1 wt. % to 15 wt. %, or from 0.1 wt. % to 8 wt. % based upon the total weight of the composition.

Detergents are additives utilized to maintain overall cleanliness by keeping sludge, carbon and deposit precursors suspended in the lubricant compositions and/or functional fluid compositions. Many detergents can be chemically similar to dispersants. Detergents which can be utilized in the lubricant compositions and/or functional fluid compositions can include the alkali or alkaline earth metal of sulfates, sulfonates, phenates, carboxylates, phosphates, carboxylic acids, and salicylates. For example, suitable detergents can include, but are not limited to, the sulfonated alkylaromatic hydrocarbons, alkyl phenols, sulfurized alkyl phenols treated with an alkaline earth metal hydroxide or oxide (e.g., CaO, Ca(OH)$_2$, BaO, Ba(OH)$_2$, MgO, or Mg(OH)$_2$). Sulfonated alkylaromatic compounds can be prepared from sulfonic acids obtained by sulfonation of $C_9$ to $C_{80}$ (or $C_6$ to $C_{60}$) alkyl substituted aromatic hydrocarbons (having one or more than one alkyl groups) where the alkyl groups independently can be $C_3$ to $C_{70}$ alkyl groups and the aromatic portion can be benzene, toluene, xylene, naphthalene, or biphenyl. Alkyl phenol and/or sulfurized alkyl phenols can have one or more $C_4$ to $C_{30}$ alkyl groups. The detergents utilized in the lubricant compositions and/or functional fluid compositions can be neutral (i.e., produced using only enough alkali or alkaline earth compound to neutralize the sulfonated alkylaromatic compound, alkyl phenol, or sulfurized alkyl phenol) or can be overbased (i.e., produced using more alkali or alkaline earth compound than necessary to neutralize the sulfonated alkylaromatic compound, alkyl phenol, or sulfurized alkyl phenol). Generally, detergents can be used in an amount of 0.01 wt. % to 6.0 wt. %, 0.05 wt. % to 5.0 wt. %, or 0.1 to 4 wt. % based upon the total weight of the composition.

Defoamants (or anti-foam agents) are additives utilized to retard the formation of stable foam in the lubricant compositions and/or functional fluid compositions. Defoamants which can be utilized in the lubricant compositions and/or functional fluid compositions can include, but are not limited to, silicone compounds (e.g., polysiloxanes, such as silicon oil or polydimethyl siloxane, among others) and organic polymers. Defoamants can be utilized in conjunction with demulsifiers. Generally, the maximum amount of defoamants can be in an amount of 1 wt. %, 0.5 wt. % or 0.1 wt. % based upon the total weight of the composition.

Antioxidants are additives utilized to retard the oxidative degradation of the base oil(s) in the lubricant compositions and/or functional fluid compositions. Oxidative base oil degradation can produce deposits on metal surfaces, sludge, and/or increase the viscosity of the lubricant composition. Antioxidants which can be utilized in the lubricant compositions and/or functional fluid compositions include, but are not limited to, hindered phenols (ashless); neutral or basic metal salts of hindered phenols; hindered phenolic carboxylic acid (e.g., propionic acid) ester derivatives; bis-hindered phenols; alkylated and non-alkylated aromatic amines; sulfurized alkyl phenols; alkali or alkaline earth metal salts of sulfurized alkyl phenols; copper dihydrocarbyl thio or dithio-phosphates; copper salts of carboxylic acids (natural or synthetic); and copper salts of dithiacarbamates, dithiocarbamates, sulphonates, phenates, acetylacetonates and alkenyl succinic acids or anhydrides (neutral, basic or acidic). Patents describing antioxidants which can be utilized in the lubricant compositions and/or functional fluid compositions include, but are not limited to, U.S. Pat. Nos. 4,798,684 and 5,084,197. Generally, the antioxidants can be used in an amount of from 0.01 wt. % to 5 wt. %, from 0.01 to 2.5 wt. %, or from 0.01 wt. % to 1.5 wt. % based upon the total weight of the composition.

Anti-wear additives and extreme pressure additives are compounds utilized to reduce friction and wear of metal parts of the base oil(s) in the lubricant compositions and/or functional fluid compositions. Anti-wear additives and extreme pressure additives which can be utilized in the lubricant compositions and/or functional fluid compositions include, but are not limited to, metal alkylthiophosphates (e.g., a zinc alkylthiophosphonate having a $C_1$ to $C_{18}$ alkyl group), metal dialkyldithiophosphates (e.g., a zinc alkylthiophosphonate having $C_1$ to $C_{18}$ alkyl groups), sulfurized $C_3$ to $C_{30}$ aliphatic or arylaliphatic hydrocarbon olefins (acyclic or cyclic), polysulfides of thiophosphorus acids, polysulfides of thiophosphorus acid esters, phosphorothioyl disulfides, alkylthiocarbamoyl compounds (e.g., bis(dibutyl)thiocarbamoyl) in combination with a molybdenum compound (e.g., oxymolybdenum diisopropylphosphorodithioate sulfide) and phosphorus ester (e.g., dibutyl hydrogen phosphite, for example), thiocarbamates, thiocarbamate/molybdenum complexes (e.g., moly-sulfur alkyl dithiocarbamate trimer complexes), and/or glycerol ester (e.g., mono-, di-, and tri-oleates, mono-palmitates and mono-myristates). Patents describing anti-wear additives and/or extreme pressure additives which can be utilized in the lubricant compositions and/or functional fluid compositions include, but are not limited to, U.S. Pat. Nos. 2,443,264; 2,471,115; 2,526,497; 2,591,577; 3,770,854; 4,501,678; 4,941,984; 5,034,141; 5,034,142; 5,084,197; and 5,693,598. Generally, the total amount of anti-wear additives and extreme pressure additives used in the lubricant compositions and/or functional fluid compositions can be in an amount of from 0.01 wt. % to 6 wt. %, from 0.01 to 5 wt. %, or from 0.01 wt. % to 4 wt. % based upon the total weight of the composition.

Anti-rust additives are additives that protect lubricated metal surfaces against chemical attack by water or other contaminants. Anti-rust additives can function by 1) wetting the metal surface with a film of oil, 2) absorbing water into a water-in-oil emulsion, and/or 3) adhering to the metal to form a non-reactive surface, among other potential modes of function. Anti-rust additives which can be utilized in the lubricant compositions and/or functional fluid compositions include, but are not limited to, zinc dithiophosphates, metal phenolates, basic metal sulfonates, fatty acids, and amines Generally, the amount of anti-rust additives used in the lubricant compositions and/or functional fluid compositions can be in an amount of from 0.01 wt. % to 5 wt. %, from 0.01 wt. % to 2.5 wt. %, or from 0.01 wt. % to 1.5 wt. % based upon the total weight of the composition.

Corrosion inhibitors are additives that reduce the degradation of metallic parts that are in contact with the lubricant compositions and/or functional fluid compositions. Corrosion inhibitors which can be utilized in the lubricant compositions and/or functional fluid compositions include, but are not limited to, thiadiazoles and triazoles. Patents describing corrosion inhibitors which can be utilized in the lubricant compositions and/or functional fluid compositions include, but are not limited to, U.S. Pat. Nos. 2,719,125; 2,719,126; and 3,087,932. Generally, the amount of corrosion inhibitors used in the lubricant compositions and/or functional fluid compositions can be in an amount of from 0.01 wt. % to 5 wt. %, from 0.01 wt. % to 2.5 wt. %, or from 0.01 wt. % to 1.5 wt. % based upon the total weight of the composition.

Pour point depressants are additives that reduce the minimum temperature at which the lubricant compositions and/or functional fluid compositions will flow or can be poured. Pour point depressants which can be utilized in the lubricant compositions and/or functional fluid compositions include, but are not limited to, polymethacrylates, polyacrylates, polyacrylamides, condensation products of haloparaffin waxes and aromatic compounds, vinyl carboxylate polymers, and terpolymers of dialkylfumarates, vinyl esters of fatty acids and allyl vinyl ethers. Patents describing pour point depressants which can be utilized in the lubricant compositions and/or functional fluid compositions include, but are not limited to, U.S. Pat. Nos. 1,815,022; 2,015,748; 2,191,498; 2,387,501; 2,655,479; 2,666,746; 2,721,877; 2,721,878; and 3,250,715. Generally, the amount of pour point depressant used in the lubricant compositions and/or functional fluid compositions can be in an amount of from 0.01 wt. % to 5 wt. %, from 0.01 wt. % to 2.5 wt. %, or from 0.01 wt. % to 1.5 wt. % based upon the total weight of the composition.

Seal compatibility additives are compounds that swell elastomeric seals and can function by causing a chemical reaction in the fluid or a physical change in the seal elastomer. Seal compatibility additives which can be utilized in the lubricant compositions and/or functional fluid compositions include, but are not limited to, organic phosphates, aromatic esters, aromatic hydrocarbons, esters (e.g., butylbenzyl phthalate), and polybutenyl succinic anhydride. Generally, the amount of seal compatibility additive used in the lubricant composition and/or functional fluid compositions can be in an amount of from 0.01 wt. % to 3 wt. %, from 0.01 wt. % to 2.5 wt. %, or from 0.01 wt. % to 2 wt. % based upon the total weight of the composition.

Various catalyst and/or catalyst system aspects and embodiments can include the use of a promoter. Non-limiting examples of promoters suitable for use in these aspects and embodiments include water, alcohols, carboxylic acids, carboxylic acid esters, carboxylic acid anhydrides, aldehydes, ketones, ethers, organohalides (e.g., alkyl halides), or any combination thereof. In some embodiments, the promoter can be water; alternatively, an alcohol; alternatively, a carboxylic acid; alternatively, a carboxylic acid ester; alternatively, a carboxylic acid anhydride; alternatively, an aldehyde; alternatively, a ketone; alternatively, an ether; or alternatively, an organohalide (e.g., an alkyl halide).

In an embodiment, the alcohol that can be utilized as the promoter in any embodiment or aspect described herein can comprise, consist essentially of, or consist of, a $C_1$ to $C_{20}$ alcohol; alternatively, a $C_1$ to $C_{15}$, alcohol; alternatively, a $C_1$ to $C_{10}$ alcohol; or alternatively, a $C_1$ to $C_6$ alcohol. In some embodiments, the alcohol can comprise, consist essentially of, or consist of, a monool, a polyol, or any combination thereof; a monool, a diol, or any combination thereof; alternatively, a monool; alternatively, a polyol; or alternatively, a diol. In some embodiments, the alcohol can comprise, consist essentially of, or consist of, a linear alcohol, a branched alcohol, or any combination thereof; alternatively, a linear alcohol; or alternatively, a branched alcohol. In some embodiments, the alcohol that can be utilized as the promoter can comprise, consist essentially of, or consist of, methanol, ethanol, a propanol, a butanol, a pentanol, a hexanol, or any combination thereof; alternatively, methanol; alternatively, ethanol; alternatively, 1-propanol; alternatively, 2-propanol; alternatively, 1-butanol; alternatively, 1-pentanol; or alternatively, 1-hexanol.

In an embodiment, the carboxylic acid that can be utilized as the promoter in any embodiment or aspect described herein can comprise, consist essentially of, or consist of, a $C_2$ to $C_{20}$ carboxylic acid; alternatively, a $C_2$ to $C_{15}$ carboxylic acid; alternatively, a $C_3$ to $C_{10}$ carboxylic acid; or alternatively, a $C_3$ to $C_8$ carboxylic acid. In some embodiments, the carboxylic acid can comprise, consist essentially of, or consist of, a mono-carboxylic acid, a poly-carboxylic acid, or any combination thereof; alternatively, a mono-carboxylic acid, a di-carboxylic acid, or any combination thereof; alternatively, a mono-carboxylic acid; alternatively, a poly-carboxylic acid; or alternatively, a di-carboxylic acid. In some embodiments, the carboxylic acid can comprise, consist essentially of, or consist of, a linear carboxylic acid, a branched carboxylic acid, or any combination thereof; alternatively, a linear carboxylic acid; or alternatively a branched carboxylic acid. In an embodiment, the carboxylic acid that can be utilized as a promoter can comprise, consist essentially of, or consist of, acetic acid, propionic acid, a butyric acid, a hexanoic acid, a heptanoic acid, an octanoic acid, a nonanoic acid, a decanoic acid, a succinic acid, or any combination thereof.

In an embodiment, the carboxylic acid ester that can be utilized as the promoter in any embodiment or aspect described herein can comprise, consist essentially of, or consist of, a $C_2$ to $C_{20}$ carboxylic acid ester; alternatively, a $C_2$ to $C_{15}$ carboxylic acid ester; alternatively, a $C_3$ to $C_{10}$ carboxylic acid ester; or alternatively, a $C_3$ to $C_8$ carboxylic acid ester. In some embodiments, the carboxylic acid ester can comprise, consist essentially of, or consist of, a carboxylic acid mono-ester, a carboxylic acid di-ester, or any combination thereof. Generally, the carboxylic acid esters which can be utilized as the promoter can be any carboxylic acid ester which can be formed from any alcohol described herein as a potential promoter and any carboxylic acid described herein as a potential promoter. In an embodiment, the carboxylic acid ester promoter can comprise, consist essentially of, or consist of, a methyl carboxylate, an ethyl carboxylate, a propyl carboxylate, a butyl carboxylate, a pentyl carboxylate, a hexyl carboxylate, or any combination thereof. In some embodiments, the ester which can be utilized as the promoter can be an acetate of any alcohol described herein as a promoter. Thus, in some embodiments, the carboxylic acid ester promoter can comprise, consist essentially of, or consist of, methyl acetate, ethyl acetate, a propyl acetate, a butyl acetate, a pentyl acetate, a hexyl acetate, or any combination thereof.

In an embodiment, the ketone that can be utilized as the promoter in any embodiment or aspect described herein can comprise, consist essentially of, or consist of, a $C_3$ to $C_{20}$ ketone; alternatively, a $C_3$ to $C_{15}$ ketone; alternatively, a $C_3$ to $C_{10}$ ketone; or alternatively, a $C_3$ to $C_8$ ketone. In some embodiments, the ketone can comprise, consist essentially of, or consist of, a monoketone, a polyketone, or any combination thereof; alternatively, a monoketone, a diketone, or any combination thereof; alternatively, a monoketone; alternatively, a polyketone, or alternatively, a diketone. In some embodiments, the ketone can comprise, consist essentially of, or consist of, a linear ketone, a branched ketone, or any combination thereof; alternatively, a linear ketone; or alternatively, a branched ketone. In an embodiment, the ketone promoter can comprise, consist essentially of, or consist of, acetone, 2-butanone, a pentanone, a hexanone, a heptanone, an octanone, or any combination thereof.

In an embodiment, the ether that can be utilized as the promoter in any embodiment or aspect described herein can comprise, consist essentially of, or consist of, a $C_2$ to $C_{20}$ ether; alternatively, a $C_3$ to $C_{15}$ ether; alternatively, a $C_3$ to $C_{10}$ ether; or alternatively, a $C_3$ to $C_8$ ether. In some embodiments, the ether can comprise, consist essentially of, or consist of, a monoether, a polyether, or any combination thereof. In an embodiment, the ether that can be utilized as the promoter can comprise, consist essentially of, or consist of, dimethyl ether, ethylmethyl ether, diethyl ether, ethylene glycol dimethyl ether, ethylene glycol methylethyl ether, ethylene glycol diethyl ether, propanediol dimethyl ether, propanediol methylethyl ether, propanediol diethyl ether, butanediol dimethyl ether, butanediol methylethyl ether, butanediol diethyl ether, diethylene glycol dimethyl ether, diethylene glycol methylethyl ether, diethylene glycol diethyl ether, triethylene glycol dimethyl ether, triethylene glycol methylethyl ether, triethylene glycol diethyl ether, pentaerythritol tetramethyl ether, or any combination thereof.

In an embodiment, the halogenated hydrocarbon that can be utilized as the promoter in any embodiment or aspect described herein can comprise, consist essentially of, or consist of, a $C_1$ to $C_{24}$ halogenated hydrocarbon; alternatively, a $C_1$ to $C_{20}$ halogenated hydrocarbon; alternatively, a $C_1$ to $C_{15}$ halogenated hydrocarbon; or alternatively, a $C_1$ to $C_{10}$ halogenated hydrocarbon. In an embodiment, the halogenated hydrocarbon promoter can be a hydrocarbon chloride, a hydrocarbon bromide, a hydrocarbon iodide, or any combination thereof; alternatively, a hydrocarbon chloride; alternatively, a hydrocarbon bromide; or alternatively, a hydrocarbon iodide. In an embodiment, the halogenated hydrocarbon promoter can comprise at least one carbon atom having only one attached halogen atom. In some embodiments, the halogenated hydrocarbon promoter can be an acyclic halogenated hydrocarbon, a cyclic halogenated hydrocarbon, or any combination thereof; alternatively, an acyclic halogenated hydrocarbon; or alternatively, a cyclic halogenated hydrocarbon. In other embodiments, the halogenated hydrocarbon promoter can comprise, consist essentially of, or consist of, an aliphatic halogenated hydrocarbon, an aromatic halogenated hydrocarbon, or any combination thereof; alternatively, an aliphatic halogenated hydrocarbon; or alternatively, an aromatic halogenated hydrocarbon. In further embodiments, the halogenated hydrocarbon promoter can comprise, consist essentially of, or consist of, a saturated halogenated hydrocarbon, an olefinic halogenated hydrocarbon. In some embodiments, the halogenated hydrocarbon promoter can comprise, consist essentially of, or consist of, a linear halogenated hydrocarbon, a branched halogenated hydrocarbon, or any combination thereof; alternatively, a linear halogenated hydrocarbon; or alternatively a branched halogenated hydrocarbon. In yet further embodiments and independent of whether the halogenated hydrocarbon promoter is saturated or olefinic, or acyclic or cyclic, the halogenated hydrocarbon promoter can comprise, consist essentially of, or consist of, a primary halogenated hydrocarbon, a secondary halogenated hydrocarbon, a tertiary halogenated hydrocarbon, or any combination thereof; alternatively, a primary halogenated hydrocarbon; alternatively, a secondary halogenated hydrocarbon; or alternatively, a tertiary halogenated hydrocarbon.

Various aspects and embodiments described herein may refer to substituted groups or compounds. In an embodiment, each substituent of any aspect or embodiment calling for a substituent can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In an embodiment, each hydrocarbyl substituent or substituent of any aspect or embodiment calling for a group substituent can be a $C_1$ to $C_{10}$ hydrocarbyl group; or alternatively, a $C_1$ to $C_5$ hydrocarbyl group. In an embodiment, each hydrocarboxy group or substituent of any aspect or embodiment calling for a group substituent can be a $C_1$ to $C_{10}$ hydrocarboxy group; or alternatively, a $C_1$ to $C_5$ hydrocarboxy group. In an embodiment, any halide substituent of any aspect or embodiment calling for a substituent can be a fluoride, chloride, bromide, or iodide; alternatively, a fluoride or chloride. In some embodiments, any halide substituent of any aspect or embodiment calling for a substituent can be a fluoride; alternatively, a chloride; alternatively, a bromide; or alternatively, an iodide.

In an embodiment, any hydrocarbyl substituent of any aspect or embodiment calling for a substituent can be an alkyl group, an aryl group, or an aralkyl group; alternatively, an alkyl group; alternatively, an aryl group; or alternatively, an aralkyl group. In an embodiment, any alkyl substituent of any aspect or embodiment calling for a substituent can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an embodiment, any aryl substituent of any aspect or embodiment calling for a substituent can be phenyl group, a tolyl group, a xylyl group, or a 2,4,6-trimethylphenyl group; alternatively, a phenyl group; alternatively, a tolyl group, alternatively, a xylyl group; or alternatively, a 2,4,6-trimethylphenyl group. In an embodiment, any aralkyl substituent of any aspect or embodiment calling for a substituent can be benzyl group or an ethylphenyl group (2-phenyleth-1-yl or 1-phenyleth-1-yl); alternatively, a benzyl group; alternatively, an ethylphenyl group; alternatively a 2-phenyleth-1-yl group; or alternatively, a 1-phenyleth-1-yl group.

In an embodiment, any hydrocarboxy substituent of any aspect or embodiment calling for a substituent can be an alkoxy group, an aryloxy group, or an aralkoxy group; alternatively, an alkoxy group; or alternatively, an aryloxy group, or an aralkoxy group. In an embodiment, any alkoxy substituent of any aspect or embodiment calling for a substituent can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an embodiment, any aryloxy substituent of any aspect or embodiment calling for a substituent can be phenoxy group, a toloxy group, a xyloxy group, or a 2,4,6-trimethylphenoxy group; alternatively, a phenoxy group; alternatively, a toloxy group, alternatively, a xyloxy group; or alternatively, a 2,4,6-trimethylphenoxy group. In an embodiment, any aralkoxy substituent of any aspect or embodiment calling for a substituent can be benzoxy group.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

The examples utilize a mixed olefins stream (e.g., olefin monomers) isolated from a commercial plant employing selective ethylene trimerization to 1-hexene technology. The olefin portion of the mixed olefin stream contained greater than 80 mol % decenes and various quantities of octenes, decenes, dodecenes, tetradecenes, and octadecenes. Table 1 provides a list of the major components (olefinic and non-olefinic) and the quantity of these components within the mixed olefin stream. Table 2 provides a list of the major $C_{10}$ components within the $C_{10}$ portion of the mixed olefin stream and the mole percentage of major $C_{10}$ components within of the $C_{10}$ portion of the mixed olefin stream.

TABLE 1

Carbon Number Component Analysis Of Mixed Olefin Stream Used in the Examples.

| Material | Wt. % |
|---|---|
| Cyclohexane | 2.23 |
| $C_8$ | 1.31 |
| $C_{10}$ | 83.91 |
| $C_{12}$ | 1.7 |

TABLE 1-continued

Carbon Number Component Analysis Of Mixed Olefin Stream Used in the Examples.

| Material | Wt. % |
|---|---|
| $C_{14}$ | 7.21 |
| $C_{18}$ | 0.23 |
| Ethylbenzene | 1.65 |
| Octanol | 1.44 |
| Total | 99.68 |

TABLE 2

Composition of $C_{10}$ Olefins Portion Of Mixed The Olefin Stream Used in the Examples

| Component | (Mol %) |
|---|---|
| 1-Decene | 4.86 |
| 2-Butyl-1-hexene | 11.82 |
| 3-Propyl-1-heptene | 17.35 |
| 4-Ethyl-1-octene | 15.61 |
| 5-Methyl-1-nonene | 38.15 |
| 4/5-Decenes | 10.86 |
| Other Decenes | 1.35 |

Example 1

Figure 1B:
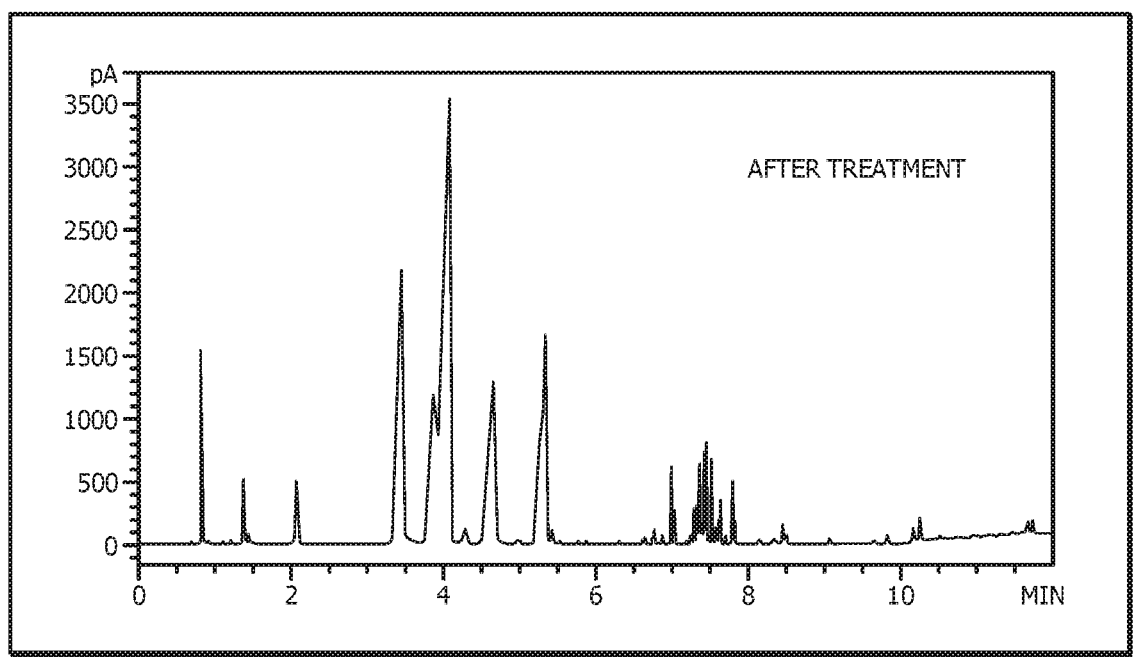

The mixed olefin stream was contacted with silica gel (high purity, 60 Å, 70-230 mesh obtained from Sigma Aldrich) and stirred overnight to remove polar compounds. The removal of polar compounds was monitored/observed visually as the mixed olefin stream was a slight yellow color and became colorless after stirring with silica, while the silica gel turned yellow. The silica gel was removed via filtration to provide treated mixed olefins. The treated mixed olefins were then stored over molecular sieves. The mixed olefin stream and the treated mixed olefins were analyzed on an Agilent 6890 gas chromatograph equipped with an Agilent 50 m×0.2 mm×0.5 μm (95/5% methyl/phenyl-polysiloxane) HP-5 column and a flame ionization detector. FIG. 1 provides a gas chromatographic analysis trace of the mixed olefin stream (1A) and the treated mixed olefin stream (1B). These gas chromatographic traces clearly show that the silica gel removed at least a component in the mixed olefin stream that had an elution time of about 5.8 minutes. Without wishing to be limited by theory, it is believed that silica gel removed at least the octanol from the mixed decene stream.

Example 2

In a nitrogen drybox, 5 g of $AlBr_3$ was pulverized using a mortar and pestle. The pulverized $AlBr_3$ was loaded into a scintillation vial containing a magnetic stir bar, a polytetrafluoroethylene (PTFE) cap, and placed on a stir plate. To the scintillation vial, isomerized decenes were slowly added over a period of 15 minutes with stirring. The addition of the isomerized decenes to the $AlBr_3$ was monitored and controlled to avoid an increase in the temperature of the solution during the isomerized decenes addition. The $AlBr_3$/isomerized decenes catalyst solution was then removed from the drybox and set aside for later use in a mixed decenes oligomerization.

Figure 2A:
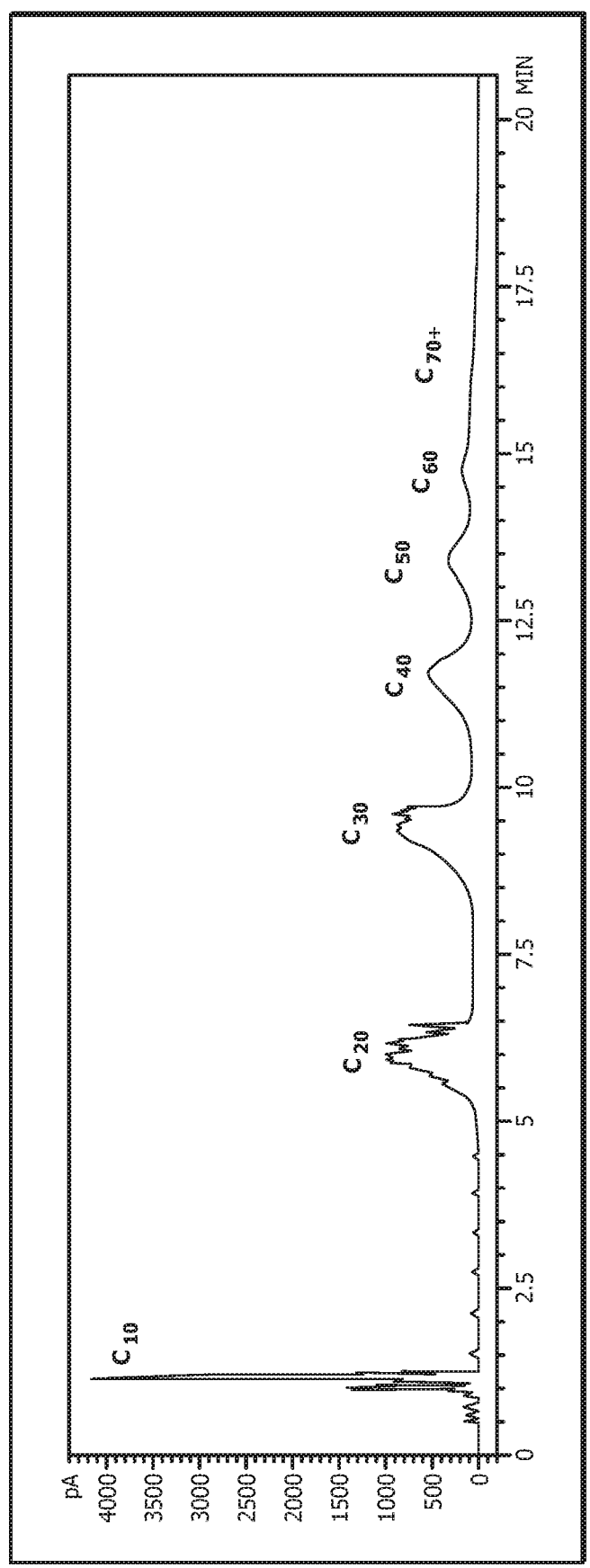
FIGS. 2A and 2B provide a comparison of GC traces for a standard 1-decene based olefin oligomers (2A) versus olefin oligomers obtained from a mixture of olefin monomers using an aluminum chloride catalyst system (2B).

In a separatory funnel, 467 g of the treated mixed olefins and 20 g of deionized water were combined and shaken together. The layers were allowed to separate and the treated mixed olefins were then removed from the separatory funnel. The treated mixed olefins (now saturated with water) were then added to a 3-neck round bottom flask equipped with septa, a magnetic stir bar, an $N_2$ purge line, and a heating mantle controlled by a rheostat controlled by a thermocouple in contact with the reaction solution, which was heated to 100° C. with stirring. To the stirring 100° C. solution were added, by syringe, 6 mL of the $AlBr_3$/isomerized decenes catalyst solution. Within 20 sec, the solution temperature rose to 120° C. and the solution turned from a clear and colorless to a clear pale yellow. After 20 minutes, another 6 mL of the $AlBr_3$/isomerized decenes catalyst solution were added to the round bottom flask, followed by another 6 mL of $AlBr_3$/isomerized decenes catalyst solution following another 30 minutes of reaction time. During the addition $AlBr_3$/isomerized decenes catalyst solution, the reaction temperature was controlled by use of an ice bath and by heating as appropriate to maintain the 100° C. reaction temperature. Over a 3 hour reaction time, the reaction turned to a bright yellow color. After 3 h, the round bottom flask contents were cooled to room temperature and allowed to stir overnight. The next day, the solution was quenched by adding basic water (pH>7), with stirring and then filtered through a 0.2 μm filter. A sample of the reaction solution was then analyzed on an Agilent 6890 gas chromatograph equipped with an Agilent 5 meter×0.53 mm×0.15 μm (100% polysiloxane) SimDist column and a flame ionization detector. FIG. 2 provides an annotated gas chromatographic analysis trace of the final reaction solution (2B) and a comparative annotated gas chromatographic trace of a final reaction solution from forming decene oligomers produced using a $BF_3$/n-butanol catalyst system (2A).

Figure 2B:
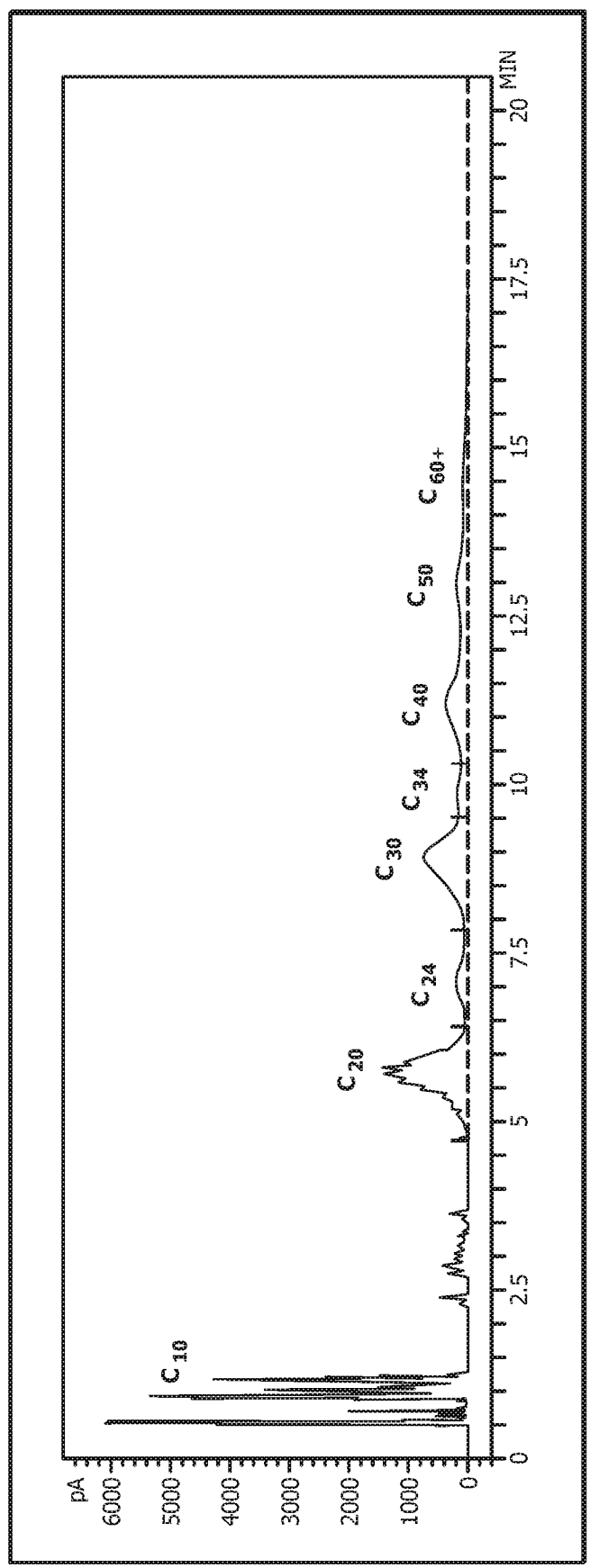

Review of the gas chromatographic traces in FIG. 2 shows that the treated mixed olefins represent a viable feedstock to produce olefin oligomers including dimers, trimers, tetramers, pentamers and hexamers that is comparable to 1-decene as a monomer feedstock. The gas chromatographic trace in FIG. 2B further shows that tetradecenes in the mixed olefins are reactive and do not represent an unreactive component by the presence of $C_{24}$ and $C_{34}$ fractions within the olefin oligomers. While not readily observable in the gas chromatographic trace and without wishing to be limited by theory, it is believed that the olefin oligomers produced using the treated mixed olefin stream contains a nearly statistical distribution of olefins oligomers from the olefins in the treated mixed decene stream. It is further believed, and without wishing to be limited by theory, that the presence of these non-homo-1-decene oligomers could lead to enhanced viscosity index properties and/or reduced volatility for lubricants produced from all or a portion of these hydrogenated olefin oligomers.

The resulting mixture was then distilled to separate monomer/dimer and leave a trimer plus bottoms fraction. During a typical distillation, the pot temperature was ~209° C. and the maximum overhead temperature observed was around 176° C.

Example 3

In a nitrogen filled glove box, a 250 mL round bottom flask equipped with septa and a magnetic stir bar was charged with 100 mL of the mixed olefin stream. The flask was then placed on a hot plate and warmed to the 80° C. Once the flask had reached the desired starting temperature, 0.1 mL (11.8 mg) of isobutyl chloride was added via syringe to the round bottom flask. Ionic liquid, 1 mL, was added to the round bottom flask, with stirring, over a period of 5 minutes. Upon the addition of the ionic liquid, the contents of the round bottom flask rapidly increased in temperature by 50° C. The reaction was allowed to continue for 60 minutes after the addition of the ionic liquid was complete. Over the reaction time period, the reaction solution changed from colorless to a light orange and was sampled at 30 minutes and 60 minutes. At the end of the 60 minutes reaction time, the reaction was then quenched by titration with n-BuOH, with stirring, until the solution lost color and a white precipitate formed. A sample of the reaction solution was then analyzed by on Agilent 6890 gas chromatograph equipped with an Agilent 5 meter×0.53 mm×0.15 μm (100% polysiloxane) SimDist column and a flame ionization detector.

Example 4

In a nitrogen filled glove box, a 250 mL round bottom flask equipped with septa and a magnetic stir bar was charged with 100 mL of the treated mixed olefins. The flask was then placed on a hot plate and warmed to the 80° C. Once the flask had reached the desired starting temperature, 0.1 mL (11.8 mg) of isobutyl chloride was added via syringe to the round bottom flask. Ionic liquid, 1 mL, was added to the round bottom flask, with stirring, over a period of 5 minutes. Upon the addition of the ionic liquid, the contents of the round bottom flask rapidly increased in temperature to 50° C. The reaction was allowed to continue for 60 minutes after the addition of the ionic liquid was complete. Over the reaction time period, the reaction solution changed from colorless to a light orange and was sampled at 30 minutes and 60 minutes. At the end of the 60 minutes reaction time, the reaction was then quenched by titration with n-BuOH, with stirring, until the solution lost color and a white precipitate formed. A sample of the reaction solution was then analyzed on Agilent 6890 gas chromatograph equipped with an Agilent 5 meter×0.53 mm×0.15 μm (100% polysiloxane) SimDist column and a flame ionization detector.

Figure 3A:
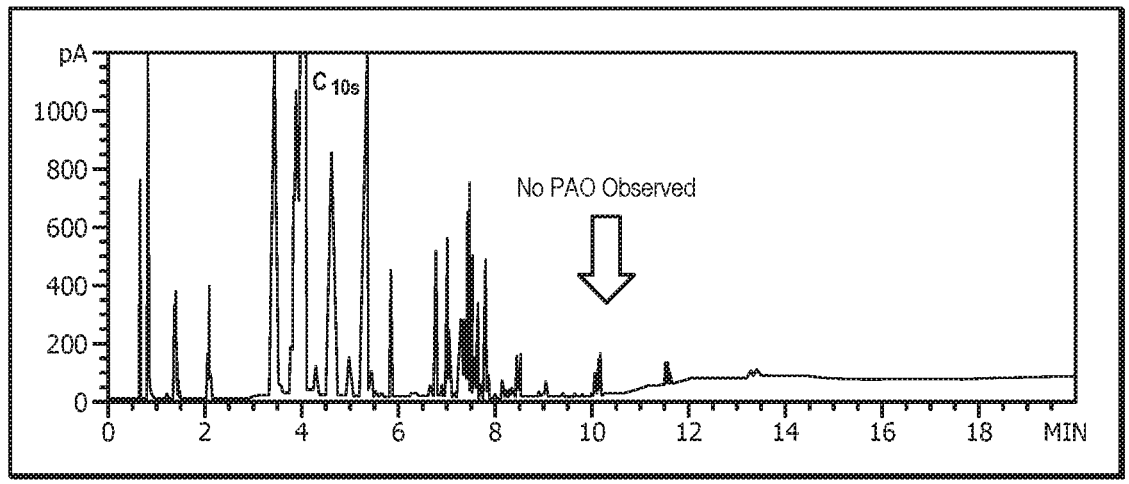
FIGS. 3A and 3B provide a comparison of GC traces for reactor effluent for olefin oligomers produced from an untreated mixed olefin stream (3A) and a treated mixed olefin stream (3B) using an ionic liquids catalyst system.
Figure 3B:
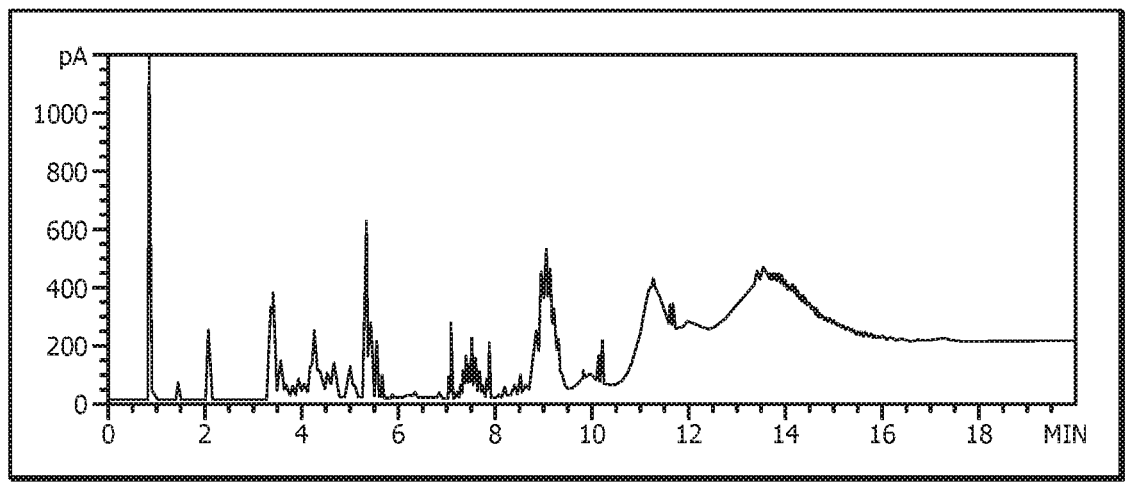

FIG. 3 provides the gas chromatographic analysis trace of the catalyst system quenched reaction solutions for Example 3 and Example 4. The gas chromatographic analysis trace in FIG. 3A shows that the use of the untreated mixed olefin stream did not produce olefin oligomers. The gas chromatographic analysis trace in FIG. 3B shows that olefin oligomers including dimers, trimers, and tetramers were produced in the ionic liquid catalyzed oligomerization of the treated mixed olefins.

Example 5

Filtrol® 24x was obtained from BASF and dried in an oven at 100° C. for at least 24 hours prior to use.

Figure 4:
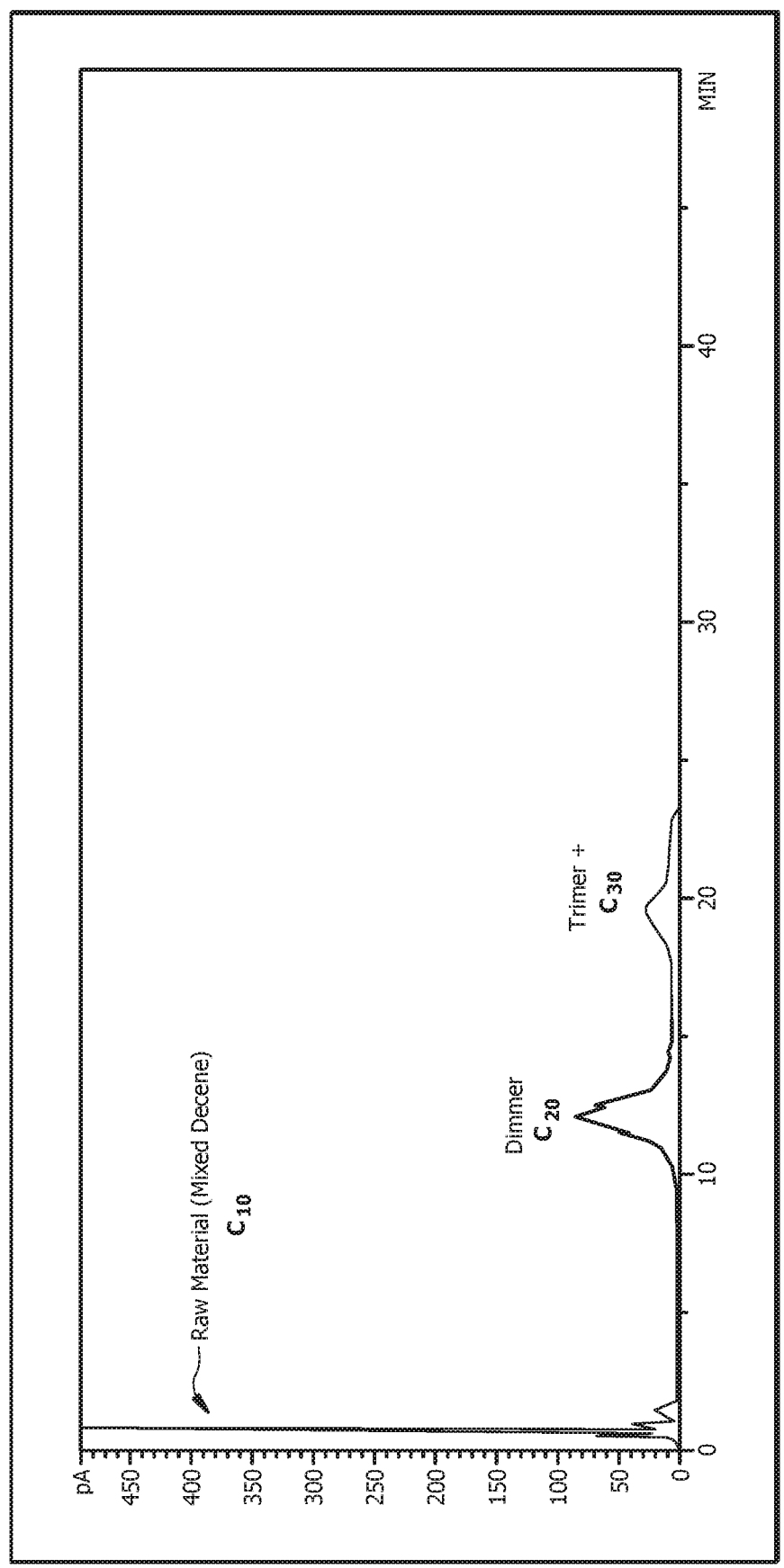
FIG. 4 provides a GC trace for a reactor effluent for olefin oligomers produced using an acid washed clay catalyst.

To a 3-neck 500 mL round bottom flask equipped with a magnetic stir bar, reflux condenser, nitrogen purge line, septa, and a heating mantle controlled by a rheostat controlled by a thermocouple in contact with the reaction solution was added 150 g of mixed decenes and 15 g of the previously dried Filtrol® 24x. The contents of the round bottom flask were heated at 150° C. for 6 hours, with stirring under a nitrogen atmosphere. After the 6 hour reaction period, the contents of the round bottom flask were allowed to cool to room temperature under a nitrogen atmosphere. A filtered sample of the reaction solution was then analyzed on a gas chromatograph equipped with a 2 meter×0.25 mm×1 μm DB-1 column and a flame ionization detector. FIG. 4 provides a gas chromatographic analysis trace of the reaction solution and shows that it contained 49% starting material (mixed decenes), 35% dimer, and 16% trimer and higher order oligomers.

Example 5 demonstrates that impurities present in mixed olefin streams isolated from selective ethylene oligomerizations process do not impede the reaction of the mixed olefins in the mixed olefin stream from a selective ethylene oligomerization plant using some catalysts or catalyst systems. However, Examples 3 and 4 demonstrate that impurities present in mixed olefin streams isolated from selective ethylene oligomerizations process can include impurities which may be detrimental to some catalysts or catalyst systems utilized to oligomerize the mixed decenes stream form an ethylene oligomerization plant. While silica gel was utilized to remove polar impurities in the mixed olefin stream for the present examples, one having ordinary skill will recognize that any desiccant/adsorbent material that interacts with polar compounds can represent effective material for treatment of a mixed olefin stream. Non-limiting examples of material which can be utilized to treat a particular mixed olefin stream can include silica gel, alumina (acidic, neutral or basic), activated carbon, molecular sieves (e.g. 13×, among others), or any combination thereof. One having ordinary skill will further recognize which olefin oligomerization catalyst systems may benefit from the pretreatment of the mixed olefin stream from a selective ethylene oligomerization plant with a desiccant/absorbent.

Example 6

Treated mixed olefins, and mixtures of the treated mixed olefins with 1-decene would be oligomerized using a catalyst system comprising $BF_3$ and n-butanol. Four mixtures of treated mixed olefins with 1-decene would be oligomerized 1) 80 mass % treated mixed olefin with 20 mass % 1-decene, 2) 60 mass % treated mixed olefin with 40 mass % 1-decene, 3) 40 mass % treated mixed olefin with 60 mass % 1-decene, and 4) 20 mass % treated mixed olefin with 80 mass % 1-decene. Each oligomerization run would use a one liter 316 stainless steel autoclave reactor equipped with a packless stirrer, an external electrical heater and an internal cooling coil for temperature control, dip tube, gas inlet and vent valves, and a pressure relief rupture disc.

The autoclave would be cleaned, dried, purged with nitrogen, sealed, and tested for leaks. The monomer feedstock (1000 g) and n-butanol (0.25 wt. % based on feed) would be charged to the reactor. The reactor contents would then be heated under a nitrogen blanket to 75° C. When the autoclave reactor temperature would reach the 75° C. equilibrium temperature, the reactor would be evacuated to remove the nitrogen and boron trifluoride gas would then be sparged slowly, with agitation and cooling water circulating through the reactor cooling coil to maintain a 75° C. reaction temperature, into the autoclave reactor to achieve an autoclave reactor pressure of 20 psig. The reaction would be continued for 2 hours by adding boron trifluoride as needed to maintain a reactor pressure of 20 psig and maintaining the reaction temperature at 75° C., using the external electrical heater and an internal cooling coil for temperature control as needed. The reaction would be terminated after two hours by venting off boron trifluoride gas and purging the autoclave reactor with nitrogen gas to replace all boron trifluoride.

The autoclave reactor contents would then be removed from the autoclave and washed one time with a 4 wt. % aqueous sodium hydroxide solution and then followed by three water washes to ensure complete neutralization or the autoclave contents. A sample of each washed reactor contents would be analyzed on a gas chromatograph equipped with a SimDist column and a flame ionization detector. The gas chromatographic analysis of the oligomer product samples would show that in each case the treated mixed olefins would react, either with themselves or with the 1-decene, to form olefin oligomers.

The remaining autoclave contents would be dried and distilled to remove low molecular weight components (components having less than 20 carbon atoms). The remaining $C_{20+}$ material would then be hydrogenated using standard hydrogenation technology. The hydrogenated product would then be filtered and analyzed for carbon number distribution, pour point, 100° C. kinematic viscosity, 40° C. kinematic viscosity, −40° C. kinematic viscosity, and viscosity index. These analyses would show that each product, or one or more portion of the each product, would have properties which would be acceptable for use in one or more lubricant applications.

Additional Disclosure

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

Embodiment A1

A composition comprising olefin oligomers of one or more olefin monomers, the olefin monomers comprising a branched $C_{10}$ olefin monomer comprising i) 3-propyl-1-heptene, ii) 4-ethyl-1-octene, iii) 5-methyl-1-nonene, or iv) any combination thereof.

Embodiment A2

A composition comprising substantially hydrogenated olefin oligomers, wherein the olefin oligomers are oligomers of one or more olefin monomers, the olefin monomers comprising a branched $C_{10}$ olefin monomer comprising i) 3-propyl-1-heptene, ii) 4-ethyl-1-octene, iii) 5-methyl-1-nonene, or iv) any combination thereof.

Embodiment A3

The composition of embodiment A1 or A2, wherein the branched $C_{10}$ olefin monomer further comprises 2-butyl-1-hexene.

Embodiment A4

The composition of embodiment A1 or A2, wherein the branched $C_{10}$ olefin monomer comprises i) 3-propyl-1-heptene, ii) 4-ethyl-1-octene, iii) 5-methyl-1-nonene, and iv) 2-butyl-1-hexene.

Embodiment A5

The composition of embodiment A4, wherein the branched $C_{10}$ olefin monomer comprises i) at least 10 mol % 3-propyl-1-heptene, ii) at least 7 mol % 4-ethyl-1-octene, iii) at least 24 mol % 5-methyl-1-nonene, and iv) at least 3 mol % 2-butyl-1-hexene.

Embodiment A6

The composition of embodiment A4, wherein the branched $C_{10}$ olefin monomer comprises i) from 10 mol % to 32 mol % 3-propyl-1-heptene, ii) from 7 mol % to 25 mol % 4-ethyl-1-octene, iii) from 24 mol % to 52 mol % 5-methyl-1-nonene, and iv) from 3 mol % to 20 mol % 2-butyl-1-hexene.

Embodiment A7

The composition of any one of embodiments A4 to A6, wherein the branched $C_{10}$ olefin monomer has a molar ratio of 5-methyl-1-nonene to 3-propyl-1-heptene of at least 1.2:1.

Embodiment A8

The composition of any one of embodiments A4 to A7, wherein the branched $C_{10}$ olefin monomer has a molar ratio of 5-methyl-1-nonene to 4-ethyl-1-octene of at least 1.6:1.

Embodiment A9

The composition of any one of embodiment A1 or A8, wherein the olefin monomers further comprise a linear internal $C_{10}$ olefin monomer selected from 4-decene, 5-decene, or any combination thereof.

Embodiment A10

The composition of embodiment A9, wherein the molar ratio of linear internal $C_{10}$ olefin monomer to branched $C_{10}$ olefin monomer ranges from 0.10:1 to 0.16:1.

Embodiment A11

The composition of any one of embodiments A1 to A10, wherein the olefin monomers further comprise linear internal $C_{14}$ olefin monomers, branched $C_{14}$ olefin monomers, or any combination thereof.

Embodiment A12

The composition of embodiment A11, wherein the molar ratio of linear internal $C_{14}$ olefin monomers and branched $C_{14}$ olefin monomers to branched $C_{10}$ olefin monomers ranges from 0.05:1 to 0.12:1.

Embodiment A13

The composition of any one of embodiments A1 to A12, wherein the olefin monomers comprise at least 20 mol %, at least 30 mol %, at least 40 mol %, at least 50 mol %, at least 60 mol %, at least 65 mol %, at least 70 mol %, at least 75 mol %, at least 80 mol %, or at least 85 mol % of the branched $C_{10}$ olefin monomer.

Embodiment A14

The composition of any one of embodiments A1 to A13, wherein the olefin monomer further comprise at least one $C_6$ to $C_{18}$ linear olefin monomer.

Embodiment A15

The composition of embodiment A14, wherein the $C_6$ to $C_{18}$ linear olefin monomer comprises 1-octene, 1-decene, 1-dodecene, or any combination thereof.

Embodiment A16

The composition of embodiment A13 or A14, wherein the olefin monomers comprise a maximum of 75 mol %, 70 mol %, 65 mol %, 60 mol %, 50 mol %, 40 mol %, 30 mol %, 25 mol %, 20 mol %, 15 mol %, 10 mol %, or 5 mol % of the $C_6$ to $C_{18}$ linear olefin monomer.

Embodiment A17

The composition of any one of embodiments A1 to A16, wherein the oligomers of the one or more olefin monomers have a 100° C. kinematic viscosity of from 1.5 cSt to 225 cSt, from 1.5 cSt to 12 cSt, from 15 cSt to 40 cSt, or from 40 cSt to 150 cSt.

Embodiment A18

The composition of any one of embodiments A1 to A16, wherein the oligomers of the one or more olefin monomers have a 100° C. kinematic viscosity of from 1.8 cSt to 2.2 cSt, from 2.3 cSt to 2.7 cSt, from 2.6 cSt to 3.4 cSt, from 3.6 cSt to 4.4 cSt, from 4.6 cSt to 5.4 cSt, from 5.6 cSt to 6.4 cSt, from 6.6 cSt to 7.4 cSt, from 7.6 cSt to 8.4 cSt, from 8.6 cSt to 9.4 cSt, or from 9.6 cSt to 10.4 cSt.

Embodiment P1

A process comprising a) contacting 1) a catalyst system and 2) a monomer feedstock comprising a branched $C_{10}$ olefin monomer comprising i) 3-propyl-1-heptene, ii) 4-ethyl-1-octene, iii) 5-methyl-1-nonene, or iv) any combination thereof in a reaction zone; and b) forming olefin oligomers.

Embodiment P2

The process of embodiment P1, wherein the branched $C_{10}$ olefin monomer further comprises 2-butyl-1-hexene.

Embodiment P3

The process of embodiment P1 or P2, wherein the branched $C_{10}$ olefin monomer comprises i) 3-propyl-1-heptene, ii) 4-ethyl-1-octene, iii) 5-methyl-1-nonene, and iv) 2-butyl-1-hexene.

Embodiment P4

The process of embodiment P3, wherein the branched $C_{10}$ olefin monomer comprises i) at least 10 mol % 3-propyl-1-heptene, ii) at least 7 mol % 4-ethyl-1-octene, iii) at least 24 mol % 5-methyl-1-nonene, and iv) at least 3 mol % 2-butyl-1-hexene.

Embodiment P5

The process of embodiment P3, wherein the branched $C_{10}$ olefin monomer comprises i) from 10 mol % to 32 mol % 3-propyl-1-heptene, ii) from 7 mol % to 25 mol % 4-ethyl-1-octene, iii) from 24 mol % to 52 mol % 5-methyl-1-nonene, and iv) from 3 mol % to 20 mol % 2-butyl-1-hexene.

Embodiment P6

The process of any one of embodiments P3 to P5, wherein the branched $C_{10}$ olefin monomer has a molar ratio of 5-methyl-1-nonene to 3-propyl-1-heptene of at least 1.2:1.

Embodiment P7

The process of any one of embodiments P3 to P5, wherein the branched $C_{10}$ olefin monomer has a molar ratio of 5-methyl-1-nonene to 4-ethyl-1-octene of at least 1.6:1.

Embodiment P8

The process of any one of embodiment P1 or P7, wherein the monomer feedstock comprises a linear internal $C_{10}$ olefin monomer selected from 4-decene, 5-decene, or any combination thereof.

Embodiment P9

The process of embodiment P8, wherein the molar ratio of linear internal $C_{10}$ olefin monomer to branched $C_{10}$ olefin monomer ranges from 0.10:1 to 0.16:1.

Embodiment P10

The process of any one of embodiments P1 to P9, wherein the monomer feedstock comprises linear internal $C_{14}$ olefin monomers, branched $C_{14}$ olefin monomers, or any combination thereof.

Embodiment P11

The process of embodiment P10, wherein the molar ratio of linear internal $C_{14}$ olefin monomers and branched $C_{14}$ olefin monomers to branched $C_{10}$ olefin monomer ranges from 0.05:1 to 0.12:1.

Embodiment P12

The process of any one of embodiments P1 to P11, wherein the monomer feedstock comprises at least 20 mol %, at least 30 mol %, at least 40 mol %, at least 50 mol %, at least 60 mol %, at least 65 mol %, at least 70 mol %, at least 75 mol %, at least 80 mol %, or at least 85 mol % of the branched $C_{10}$ olefin monomer.

Embodiment P13

The process of any one of embodiments P1 to P12, wherein the monomer feedstock comprises at least one $C_6$ to $C_{18}$ linear olefin monomer.

Embodiment P14

The process of embodiment P13, wherein the $C_6$ to $C_{18}$ linear olefin monomer comprises 1-octene, 1-decene, 1-dodecene, or any combination thereof.

Embodiment P15

The process of embodiment P12 or P13, wherein the monomer feedstock comprises a maximum of 75 mol %, 70 mol %, 65 mol %, 60 mol %, 50 mol %, 40 mol %, 30 mol %, 25 mol %, 20 mol %, 15 mol %, 10 mol %, or 5 mol % of the $C_6$ to $C_{18}$ linear olefin monomer.

Embodiment P16

The process of any one of embodiments P1 to P15, wherein the catalyst system comprises a Lewis acid.

Embodiment P17

The process of any one of embodiments P1 to P15, wherein the catalyst system comprises a boron trihalide, an aluminum halide compound, a titanium halide, an iron halide compound, a gallium halide, a tin halide, or any combination thereof.

Embodiment P18

The process of any one of embodiments P1 to P15, wherein the catalyst system is selected from the group consisting of (a) a catalyst system comprising $BF_3$, (b) a catalyst system comprising an alkylaluminum halide, an aluminum trihalide, or any combination thereof, (c) a supported metal oxide, (d) a catalyst system comprising an acidic ionic liquid, (e) a catalyst system comprising a metallocene, (f) a catalyst system comprising a clay, an acidic clay, or an acid washed clay, and (g) an acidic ion exchange resin.

Embodiment P19

The process of any one of embodiments P1 to P15, wherein the catalyst system comprises (a) an alkylaluminum halide, an aluminum trihalide, or any combination thereof; and (b) a promoter selected from the group consisting of water, alcohols, carboxylic acids, carboxylic acid esters, carboxylic acid anhydrides, aldehydes, ketones, ethers, organohalides (e.g., alkyl halides), and combinations thereof.

Embodiment P20

The process of any one of embodiments P1 to P15, wherein the catalyst system comprises (a) $BF_3$ and (b) a promoter selected from the group consisting of water, alcohols, carboxylic acids, carboxylic acid esters, carboxylic acid anhydrides, aldehydes, ketones, ethers, organohalides (e.g., alkyl halides), and combinations thereof.

Embodiment P21

The process of any one of embodiments P1 to P15, wherein the catalyst system comprises a supported metal oxide.

Embodiment P22

The process of embodiment P15, wherein the catalyst system comprises a chromium oxide on silica.

Embodiment P23

The process of any one of embodiments P1 to P15, wherein the catalyst system comprises an acidic ionic liquid.

Embodiment P24

The process of embodiment P23, wherein the acidic ionic liquid is selected from the group consisting of trialkylammonium haloaluminate ionic liquid, tetraalkylammonium haloaluminate ionic liquid, hydrogen pyridinium haloaluminate ionic liquid, N-alkylpryidinium haloaluminate ionic liquid, N,N'-dialkylimidizolium haloaluminate ionic liquid, or any combination thereof.

Embodiment P25

The process of any one of embodiments P1 to P15, wherein the catalyst system comprises (a) a metallocene and an aluminoxane, (b) a metallocene, a non-coordinating anion, and an alkylaluminum compound, or (c) a metallocene, a chemically-treated solid oxide, and an alkylaluminum compound.

Embodiment P26

The process of any one of embodiments P1 to P25, wherein the reaction zone comprises a continuous stirred tank reactor (CSTR), a plug flow reactor, a fixed bed reactor, or any combination thereof.

Embodiment P27

The process of any one of embodiments P1 to P26, further comprising removing a reaction zone effluent from the reaction zone and optionally contacting the reaction zone effluent with a catalyst system deactivating agent to form a deactivated reaction zone effluent.

Embodiment P28

The process of any one of embodiments P1 to P27, further comprising removing at least a portion of the monomer feedstock from the reaction zone effluent or deactivated reaction zone effluent.

Embodiment P29

The process of any one of embodiments P1 to P28, further comprising isolating one or more fractions comprising all or a portion of the olefin oligomers from the reaction zone effluent or deactivated reaction zone effluent.

Embodiment P30

The process of embodiment P29, further comprising hydrogenating at least one of the one or more fractions comprising all or a portion of the olefin oligomers.

Embodiment P31

The process of embodiment P30, further comprising isolating one or more fractions from the hydrogenated one or more fractions comprising all or a portion of the olefin oligomers.

Embodiment P32

The process of any one of embodiments P29 to P31, wherein the olefin oligomers, the at least one of the one or more fractions comprising all or a portion of the olefin oligomers, or the at least one of one or more fractions of the hydrogenated one or more fractions comprising all or a portion of the olefin oligomers has a 100° C. kinematic viscosity of from 1.5 cSt to 225 cSt; from 1.5 cSt to 12 cSt; from 15 cSt to 40 cSt; or from 40 cSt to 150 cSt.

Embodiment P33

The process of any one of embodiments P29 to P31, wherein the olefin oligomers, the at least one of the one or more fractions comprising all or a portion of the olefin oligomers, or the at least one of one or more fractions of the hydrogenated one or more fractions comprising all or a portion of the olefin oligomers has a 100° C. kinematic viscosity of from 1.8 cSt to 2.2 cSt, from 2.3 cSt to 2.7 cSt, from 2.6 cSt to 3.4 cSt, from 3.6 cSt to 4.4 cSt, from 4.6 cSt to 5.4 cSt, from 5.6 cSt to 6.4 cSt, from 6.6 cSt to 7.4 cSt, from 7.6 cSt to 8.4 cSt, from 8.6 cSt to 9.4 cSt, or from 9.6 cSt to 10.4 cSt.

A first aspect, which is a composition comprising oligomers of one or more olefin monomers, the olefin monomers comprising a branched $C_{10}$ olefin monomer comprising i) 3-propyl-1-heptene, ii) 4-ethyl-1-octene, iii) 5-methyl-1-nonene, or iv) any combination thereof.

A second aspect, which is the composition of the first aspect, wherein the branched $C_{10}$ olefin monomer further comprises 2-butyl-1-hexene.

A third aspect, which is the composition of any one of the first and the second aspects, wherein the branched $C_{10}$ olefin monomer comprises i) at least 10 mol % 3-propyl-1-heptene, ii) at least 7 mol % 4-ethyl-1-octene, iii) at least 24 mol % 5-methyl-1-nonene, and iv) at least 3 mol % 2-butyl-1-hexene.

A fourth aspect, which is the composition of any one of the first through the third aspects, wherein the olefin monomers further comprise a linear internal $C_{10}$ olefin monomer selected from 4-decene, 5-decene, or any combination thereof.

A fifth aspect, which is the composition of any one of the first through the fourth aspects, wherein the olefin monomers further comprise linear internal $C_{14}$ olefin monomers, branched $C_{14}$ olefin monomers, or any combination thereof.

A sixth aspect, which is the composition of any one of the first through the fifth aspects, wherein the olefin monomers further comprise at least one $C_6$ to $C_{18}$ normal alpha olefin monomer.

A seventh aspect, which is the composition of the sixth aspect, wherein the $C_6$ to $C_{18}$ normal alpha olefin monomer comprises 1-octene, 1-decene, 1-dodecene, or any combination thereof.

An eighth aspect, which is the composition of any one of the sixth through the seventh aspects, wherein the olefin monomers comprise less than or equal to 75 mol % of the $C_6$ to $C_{18}$ normal alpha olefin monomer.

A ninth aspect, which is the composition of any one of the first through the eighth aspects, wherein the olefin monomers comprise 1) at least 80 mol % branched $C_{10}$ olefin monomer, the branched $C_{10}$ olefin monomer comprising i) from 10 mol % to 32 mol % 3-propyl-1-heptene, ii) from 7 mol % to 25 mol % 4-ethyl-1-octene, iii) from 24 mol % to 52 mol % 5-methyl-1-nonene, and iv) from 3 mol % to 20 mol % 2-butyl-1-hexene; and 2) less than 10 mole % $C_6$ to $C_{18}$ normal alpha olefin monomer.

A tenth aspect, which is a composition comprising substantially hydrogenated olefin oligomers, wherein the olefin oligomers are oligomers of one or more olefin monomers, the olefin monomers comprising a branched $C_{10}$ olefin monomer comprising i) 3-propyl-1-heptene, ii) 4-ethyl-1-octene, iii) 5-methyl-1-nonene, or iv) any combination thereof.

An eleventh aspect, which is the composition of the tenth aspect, wherein the branched $C_{10}$ olefin monomer further comprises 2-butyl-1-hexene.

A twelfth aspect, which is the composition of any one of the tenth and the eleventh aspects, wherein the branched $C_{10}$ olefin monomer comprises i) at least 10 mol % 3-propyl-1-heptene, ii) at least 7 mol % 4-ethyl-1-octene, iii) at least 24 mol % 5-methyl-1-nonene, and iv) at least 3 mol % 2-butyl-1-hexene.

A thirteenth aspect, which is the composition of any one of the tenth through the twelfth aspects, wherein the olefin monomers further comprise a linear internal $C_{10}$ olefin monomer selected from 4-decene, 5-decene, or any combination thereof.

A fourteenth aspect, which is the composition of any one of the tenth through the thirteenth aspects, wherein the olefin monomer further comprise linear internal $C_{14}$ olefin monomers, branched $C_{14}$ olefin monomers, or any combination thereof.

A fifteenth aspect, which is the composition of any one of the tenth through the fourteenth aspects, wherein the olefin monomers further comprise at least one $C_6$ to $C_{18}$ normal alpha olefin monomer.

A sixteenth aspect, which is the composition of the fifteenth aspect, wherein the $C_6$ to $C_{18}$ normal alpha olefin monomer comprises 1-octene, 1-decene, 1-dodecene, or any combination thereof.

A seventeenth aspect, which is the composition of any one of the fifteenth through the sixteenth aspects, wherein the olefin monomers comprise less than or equal to 75 mol % of the $C_6$ to $C_{18}$ normal alpha olefin monomer.

An eighteenth aspect, which is the composition of any one of the tenth through the seventeenth aspects, wherein the olefin monomers comprise 1) at least 80 mol % branched $C_{10}$ olefin monomer, the branched $C_{10}$ olefin monomer comprising i) from 10 mol % to 32 mol % 3-propyl-1-heptene, ii) from 7 mol % to 25 mol % 4-ethyl-1-octene, iii) from 24 mol % to 52 mol % 5-methyl-1-nonene, and iv) from 3 mol % to 20 mol % 2-butyl-1-hexene; and 2) less than 10 mol % normal alpha olefin monomer.

A nineteenth aspect, which is a process comprising a) contacting 1) a catalyst system and 2) a monomer feedstock comprising a branched $C_{10}$ olefin monomer comprising i) 3-propyl-1-heptene, ii) 4-ethyl-1-octene, iii) 5-methyl-1-nonene, or iv) any combination thereof in a reaction zone; and b) forming olefin oligomers.

A twentieth aspect, which is the process of the nineteenth aspect, wherein the branched $C_{10}$ olefin monomer further comprises 2-butyl-1-hexene.

A twenty-first aspect, which is the process of any one of the nineteenth and the twentieth aspects, wherein the monomer feedstock further comprise a linear internal $C_{10}$ olefin monomer selected from 4-decene, 5-decene, or any combination thereof.

A twenty-second aspect, which is the process of any one of the nineteenth through the twenty-first aspects, wherein the monomer feedstock further comprises linear internal $C_{14}$ olefin monomers, branched $C_{14}$ olefin monomers, or any combination thereof.

A twenty-third aspect, which is the process of any one of the nineteenth through the twenty-second aspects, wherein the monomer feedstock further comprise at least one $C_6$ to $C_{18}$ normal alpha olefin monomer.

A twenty-fourth aspect, which is the process of the twenty-third aspect, wherein the $C_6$ to $C_{18}$ normal alpha olefin monomer comprises 1-octene, 1-decene, 1-dodecene, or any combination thereof.

A twenty-fifth aspect, which is the process of any one of the twenty-third through the twenty-fourth aspects, wherein the monomer feedstock comprises less than or equal to 75 mol % of the $C_6$ to $C_{18}$ normal alpha olefin monomer.

A twenty-sixth aspect, which is process of any one of the nineteenth through the twenty-fifth aspects, wherein the monomer feedstock comprises 1) at least 80 mol % branched $C_{10}$ olefin monomer, the branched $C_{10}$ olefin monomer comprising i) from 10 mol % to 32 mol % 3-propyl-1-heptene, ii) from 7 mol % to 25 mol % 4-ethyl-1-octene, iii) from 24 mol % to 52 mol % 5-methyl-1-nonene, and iv) from 3 mol % to 20 mol % 2-butyl-1-hexene; and 2) less than 10 mol % normal alpha olefin monomer.

A twenty-seventh aspect, which is the process of any one of the nineteenth through the twenty-sixth aspects, wherein the catalyst system comprises a Lewis acid.

A twenty-eighth aspect, which is the process of any one of the nineteenth through the twenty-sixth aspects, wherein the catalyst system is selected from the group consisting of (a) a catalyst system comprising $BF_3$, (b) a catalyst system comprising an alkylaluminum halide, an aluminum trihalide, or any combination thereof, (c) a supported metal oxide, (d) a catalyst system comprising an acidic ionic liquid, (e) a catalyst system comprising a metallocene, (f) a catalyst system comprising a clay, an acidic clay, or an acid washed clay, and (g) an acidic ion exchange resin.

A twenty-ninth aspect, which is the process of any one of the nineteenth through the twenty-sixth aspects, wherein the catalyst system comprises (a) an alkylaluminum halide, an aluminum trihalide, or any combination thereof; and (b) a promoter selected from the group consisting of water, alcohols, carboxylic acids, carboxylic acid esters, carboxylic acid anhydrides, aldehydes, ketones, ethers, organohalides, and combinations thereof.

A thirtieth aspect, which is the process of any one of the nineteenth through the twenty-sixth aspects, wherein the catalyst system comprises (a) $BF_3$ and (b) a promoter selected from the group consisting of water, alcohols, carboxylic acids, carboxylic acid esters, carboxylic acid anhydrides, aldehydes, ketones, ethers, organohalides, and combinations thereof.

A thirty-first aspect, which is the process of any one of the nineteenth through the twenty-sixth aspects, wherein the catalyst system comprises a supported metal oxide.

A thirty-second aspect, which is the process of the thirty-first aspect, wherein the catalyst system comprises a chromium oxide on silica.

A thirty-third aspect, which is the process of any one of the nineteenth through the twenty-sixth aspects, wherein the catalyst system comprises an acidic ionic liquid.

A thirty-fourth aspect, which is the process of the thirty-third aspect, wherein the acidic ionic liquid is selected from the group consisting of trialkylammonium haloaluminate ionic liquid, tetraalkylammonium haloaluminate ionic liquid, hydrogen pyridinium haloaluminate ionic liquid, N-alkylpryidinium haloaluminate ionic liquid, N,N'-dialkylimidizolium haloaluminate ionic liquid, or any combination thereof.

A thirty-fifth aspect, which is the process of any one of the nineteenth through the twenty-sixth aspects, wherein the catalyst system comprises (a) a metallocene and an aluminoxane, (b) a metallocene, a non-coordinating anion, and an alkylaluminum compound, or (c) a metallocene, a chemically-treated solid oxide, and an alkylaluminum compound.

A thirty-sixth aspect, which is the process of any one of the nineteenth through the thirty-fifth aspects, wherein the reaction zone comprises a continuous stirred tank reactor (CSTR), a plug flow reactor, a fixed bed reactor, or any combination thereof.

A thirty-seventh aspect, which is the process of any one of the nineteenth through the thirty-sixth aspects, further comprising removing a reaction zone effluent from the reaction zone and optionally contacting the reaction zone effluent with a catalyst system deactivating agent to form a deactivated reaction zone effluent.

A thirty-eighth aspect, which is the process of the thirty-seventh aspect, further comprising removing at least a portion of the monomer feedstock from the reaction zone effluent or deactivated reaction zone effluent.

A thirty-ninth aspect, which is the process of any one of the nineteenth through the thirty-eighth aspects, further comprising isolating one or more fractions comprising all or a portion of the olefin oligomers from the reaction zone effluent or deactivated reaction zone effluent.

A fortieth aspect, which is the process of the thirty-ninth aspect, further comprising hydrogenating at least one of the one or more fractions comprising all or a portion of the olefin oligomers.

A forty-first aspect, which is the process of the fortieth aspect, further comprising isolating one or more fractions from the hydrogenated one or more fractions comprising all or a portion of the olefin oligomers.

A forty-second aspect, which is the process of the forty-first aspect, wherein the at least one of the one or more fractions of the hydrogenated one or more fractions comprising all or a portion of the olefin oligomers has a 100° C. kinematic viscosity of from 1.5 cSt to 225 cSt; from 1.5 cSt to 12 cSt; from 15 cSt to 40 cSt; or from 40 cSt to 150 cSt.

While aspects and embodiments of the disclosure have been shown and described, modifications thereof can be made without departing from the spirit and teachings of the invention. The aspects, embodiments and examples described herein are exemplary only, and are not intended to be limiting. Many variations and modifications of the invention disclosed herein are possible and are within the scope of the invention.

At least one embodiment and/or aspect is disclosed and variations, combinations, and/or modifications of the embodiment(s), aspect(s), and/or feature(s) of the embodiment(s) and/or aspect(s) made by a person having ordinary skill in the art are within the scope of the disclosure. Alternative embodiments and/or aspects that result from combining, integrating, and/or omitting features of the embodiment(s) and/or aspects are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent . . . 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A process comprising a) contacting 1) a catalyst system and 2) a monomer feedstock comprising branched $C_{10}$ olefin monomers comprising i) 3-propyl-1-heptene, ii) 4-ethyl-1-octene, and iii) 5-methyl-1-nonene; and b) forming olefin oligomers; wherein the olefin oligomers have a 100° C. kinematic viscosity of from 1.5 cSt to 12 cSt; or from 15 cSt to 40 cSt, wherein the catalyst system is selected from the group consisting of (a) a catalyst system comprising $BF_3$, (b) a catalyst system consisting essentially of (i) an alkylaluminum halide, an aluminum trihalide, or any combination thereof and (ii) a promoter selected from the group consisting of water, an alcohol, a carboxylic acid, an ester, a ketone, an ether, a halogenated hydrocarbon, and any combination thereof, (c) a supported metal oxide consisting essentially of chromium oxide supported on an inert support where the inert support comprises silica, alumina, titania, silica alumina, magnesia, or combinations thereof, (d) a catalyst system comprising an acidic ionic liquid, (e) a catalyst system comprising a metallocene, (f) a catalyst system comprising a clay, an acidic clay, or an acid washed clay, and (g) an acidic ion exchange resin.

2. The process of claim 1, wherein the monomer feedstock further comprise 1) a linear internal $C_{10}$ olefin monomer selected from 4-decene, 5-decene, or any combination thereof and/or 2) linear internal $C_{14}$ olefin monomers, branched $C_{14}$ olefin monomers, or any combination thereof.

3. The process of claim 1, wherein the branched $C_{10}$ olefin monomer comprises i) at least 10 mol % 3-propyl-1-heptene, ii) at least 7 mol % 4-ethyl-1-octene, iii) at least 24 mol % 5-methyl-1-nonene, and iv) at least 3 mol % 2-butyl-1-hexene.

4. The process of claim 1, wherein the monomer feedstock further comprise less than or equal to 75 mol % of at least one $C_6$ to $C_{18}$ normal alpha olefin monomer.

5. The process of claim 4, wherein the $C_6$ to $C_{18}$ normal alpha olefin monomer comprises 1-octene, 1-decene, 1-dodecene, or any combination thereof.

6. The process of claim 5, further comprising:
removing a reaction zone effluent from the reaction zone and optionally contacting the reaction zone effluent with a catalyst system deactivating agent to form a deactivated reaction zone effluent, and
removing at least a portion of the monomer feedstock from the reaction zone effluent or deactivated reaction zone effluent.

7. The process of claim 6, further comprising:
isolating one or more fractions comprising all or a portion of the olefin oligomers from the reaction zone effluent or deactivated reaction zone effluent, and
hydrogenating at least one of the one or more fractions comprising all or a portion of the olefin oligomers.

8. The process of claim 1, wherein the monomer feedstock comprises 1) at least 80 mol % branched $C_{10}$ olefin monomer, the branched $C_{10}$ olefin monomer comprising i) from 10 mol % to 32 mol % 3-propyl-1-heptene, ii) from 7 mol % to 25 mol % 4-ethyl-1-octene, iii) from 24 mol % to 52 mol % 5-methyl-1-nonene, and iv) from 3 mol % to 20 mol % 2-butyl-1-hexene; and 2) less than 10 mol % normal alpha olefin monomer.

9. The process of claim 8, further comprising:
removing a reaction zone effluent from the reaction zone and optionally contacting the reaction zone effluent with a catalyst system deactivating agent to form a deactivated reaction zone effluent, and
removing at least a portion of the monomer feedstock from the reaction zone effluent or deactivated reaction zone effluent.

10. The process of claim 9, further comprising:
isolating one or more fractions comprising all or a portion of the olefin oligomers from the reaction zone effluent or deactivated reaction zone effluent, and
hydrogenating at least one of the one or more fractions comprising all or a portion of the olefin oligomers.

11. The process of claim 1, further comprising removing a reaction zone effluent from the reaction zone and optionally contacting the reaction zone effluent with a catalyst system deactivating agent to form a deactivated reaction zone effluent.

12. The process of claim 11, further comprising removing at least a portion of the monomer feedstock from the reaction zone effluent or deactivated reaction zone effluent.

13. The process of claim 11, further comprising isolating one or more fractions comprising all or a portion of the olefin oligomers from the reaction zone effluent or deactivated reaction zone effluent.

14. The process of claim 13, further comprising hydrogenating at least one of the one or more fractions comprising all or a portion of the olefin oligomers.

15. The process of claim 14, further comprising isolating one or more fractions from the hydrogenated one or more fractions comprising all or a portion of the olefin oligomers.

16. The process of claim 15, wherein the at least one of the one or more fractions of the hydrogenated one or more fractions comprising all or a portion of the olefin oligomers has a 100° C. kinematic viscosity of from 1.5 cSt to 12 cSt; or from 15 cSt to 40 cSt.

* * * * *